United States Patent
Neal, II et al.

(10) Patent No.: US 11,254,926 B2
(45) Date of Patent: Feb. 22, 2022

(54) DEVICES AND METHODS FOR HIGH FREQUENCY ELECTROPORATION

(71) Applicant: Virginia Tech Intellectual Properties, Inc., Blacksburg, VA (US)

(72) Inventors: Robert E. Neal, II, Richmond, VA (US); Paulo A. Garcia, Cambridge, MA (US); Rafael V. Davalos, Blacksburg, VA (US); John H. Rossmeisl, Blacksburg, VA (US); John L. Robertson, Floyd, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 16/404,392

(22) Filed: May 6, 2019

(65) Prior Publication Data
US 2019/0256839 A1    Aug. 22, 2019

Related U.S. Application Data

(60) Continuation of application No. 14/808,679, filed on Jul. 24, 2015, which is a division of application No.
(Continued)

(51) Int. Cl.
C12N 13/00 (2006.01)
A61B 34/10 (2016.01)
(Continued)

(52) U.S. Cl.
CPC .............. *C12N 13/00* (2013.01); *A61B 18/12* (2013.01); *A61B 34/10* (2016.02);
(Continued)

(58) Field of Classification Search
CPC ........ A61B 2018/00613; A61N 1/0412; C12N 13/00
See application file for complete search history.

(56) References Cited

U.S. PATENT DOCUMENTS

| 1,653,819 A | 12/1927 | Northcott |
| 3,730,238 A | 5/1973 | Butler |

(Continued)

FOREIGN PATENT DOCUMENTS

| AU | 7656800 A | 4/2001 |
| AU | 2002315095 A1 | 12/2002 |

(Continued)

OTHER PUBLICATIONS

Co-Pending U.S. Appl. No. 16/177,745, Applicant-initiated interview summary dated Dec. 16, 2019, 3 pages.
(Continued)

*Primary Examiner* — Linda C Dvorak
*Assistant Examiner* — Ryan T Clark
(74) *Attorney, Agent, or Firm* — New River Valley IP Law, P.C.; Michele L. Mayberry

(57) ABSTRACT

The present invention provides systems, methods, and devices for electroporation-based therapies (EBTs). Embodiments provide patient-specific treatment protocols derived by the numerical modeling of 3D reconstructions of target tissue from images taken of the tissue, and optionally accounting for one or more of physical constraints or dynamic tissue properties. The present invention further relates to systems, methods, and devices for delivering bipolar electric pulses for irreversible electroporation exhibiting reduced or no damage to tissue typically associated with an EBT-induced excessive charge delivered to the tissue.

20 Claims, 48 Drawing Sheets

Related U.S. Application Data

12/906,923, filed on Oct. 18, 2010, now Pat. No. 9,198,733, which is a continuation-in-part of application No. 12/757,901, filed on Apr. 9, 2010, now Pat. No. 8,926,606, said application No. 12/906,923 is a continuation-in-part of application No. 12/609,779, filed on Oct. 30, 2009, now Pat. No. 8,465,484, and a continuation-in-part of application No. 12/491,151, filed on Jun. 24, 2009, now Pat. No. 8,992,517, which is a continuation-in-part of application No. 12/432,295, filed on Apr. 29, 2009, now Pat. No. 9,598,691, application No. 16/404,392, which is a continuation-in-part of application No. 13/332,133, filed on Dec. 20, 2011, now Pat. No. 10,448,989, which is a continuation-in-part of application No. 12/757,901, filed on Apr. 9, 2010, now Pat. No. 8,926,606.

(60) Provisional application No. 61/252,445, filed on Oct. 16, 2009, provisional application No. 61/167,997, filed on Apr. 9, 2009, provisional application No. 61/285,618, filed on Dec. 11, 2009, provisional application No. 61/075,216, filed on Jun. 24, 2008, provisional application No. 61/171,564, filed on Apr. 22, 2009, provisional application No. 61/125,840, filed on Apr. 29, 2008, provisional application No. 61/424,872, filed on Dec. 20, 2010.

(51) Int. Cl.
| | | |
|---|---|---|
| A61B 18/12 | (2006.01) | |
| A61B 18/00 | (2006.01) | |
| A61N 1/04 | (2006.01) | |
| G16H 50/50 | (2018.01) | |

(52) U.S. Cl.
CPC ............... *A61B 2018/00613* (2013.01); *A61B 2034/104* (2016.02); *A61B 2034/105* (2016.02); *A61N 1/0412* (2013.01); *G16H 50/50* (2018.01)

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,903,707 A | 2/1990 | Knute et al. |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| 1,329,496 A | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| 1,351,661 A | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Vu Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |

(56) References Cited

U.S. PATENT DOCUMENTS

| | | | |
|---|---|---|---|
| 5,546,940 | A | 8/1996 | Panescu et al. |
| 5,562,720 | A | 10/1996 | Stern et al. |
| 5,575,811 | A | 11/1996 | Reid et al. |
| 1,376,652 | A | 12/1996 | Hunt et al. |
| 5,582,588 | A | 12/1996 | Sakurai et al. |
| 5,586,982 | A | 12/1996 | Abela |
| 5,588,424 | A | 12/1996 | Insler et al. |
| 5,588,960 | A | 12/1996 | Edwards et al. |
| 5,599,294 | A | 2/1997 | Edwards et al. |
| 5,599,311 | A | 2/1997 | Raulerson |
| 5,616,126 | A | 4/1997 | Malekmehr et al. |
| 5,620,479 | A | 4/1997 | Diederich |
| 5,626,146 | A | 5/1997 | Barber et al. |
| 1,380,272 | A | 6/1997 | Partika et al. |
| 5,634,899 | A | 6/1997 | Shapland et al. |
| 5,643,197 | A | 7/1997 | Brucker et al. |
| 5,645,855 | A | 7/1997 | Lorenz |
| 5,672,173 | A | 9/1997 | Gough et al. |
| 5,674,267 | A | 10/1997 | Mir et al. |
| 5,683,384 | A | 11/1997 | Gough et al. |
| 5,687,723 | A | 11/1997 | Avitall |
| 5,690,620 | A | 11/1997 | Knott |
| 5,697,905 | A | 12/1997 | d'Ambrosio |
| 5,700,252 | A | 12/1997 | Klingenstein |
| 5,702,359 | A | 12/1997 | Hofmann et al. |
| 5,718,246 | A | 2/1998 | Vona |
| 5,720,921 | A | 2/1998 | Meserol |
| 5,735,847 | A | 4/1998 | Gough et al. |
| 5,752,939 | A | 5/1998 | Makoto |
| 5,778,894 | A | 7/1998 | Dorogi et al. |
| 5,782,882 | A | 7/1998 | Lerman et al. |
| 5,800,378 | A | 9/1998 | Edwards et al. |
| 5,800,484 | A | 9/1998 | Gough et al. |
| 5,807,272 | A | 9/1998 | Kun et al. |
| 5,807,306 | A | 9/1998 | Shapland et al. |
| 5,807,395 | A | 9/1998 | Mulier et al. |
| 5,810,742 | A | 9/1998 | Peariman |
| 5,810,762 | A | 9/1998 | Hofmann |
| 5,830,184 | A | 11/1998 | Basta |
| 5,836,897 | A | 11/1998 | Sakurai et al. |
| 5,836,905 | A | 11/1998 | Lemelson et al. |
| 5,843,026 | A | 12/1998 | Edwards et al. |
| 5,843,182 | A | 12/1998 | Goldstein |
| 5,865,787 | A | 2/1999 | Shapland et al. |
| 5,868,708 | A | 2/1999 | Hart et al. |
| 5,873,849 | A | 2/1999 | Bernard |
| 5,904,648 | A | 5/1999 | Arndt et al. |
| 5,919,142 | A | 7/1999 | Boone et al. |
| 5,919,191 | A | 7/1999 | Lennox et al. |
| 5,921,982 | A | 7/1999 | Lesh et al. |
| 5,944,710 | A | 8/1999 | Dev et al. |
| 5,947,284 | A | 9/1999 | Foster |
| 5,947,889 | A | 9/1999 | Hehrlein |
| 5,951,546 | A | 9/1999 | Lorentzen |
| 5,954,745 | A | 9/1999 | Gertler et al. |
| 5,957,919 | A | 9/1999 | Laufer |
| 5,957,963 | A | 9/1999 | Dobak |
| 5,968,006 | A | 10/1999 | Hofmann |
| 5,983,131 | A | 11/1999 | Weaver et al. |
| 5,984,896 | A | 11/1999 | Boyd |
| 5,991,697 | A | 11/1999 | Nelson et al. |
| 5,999,847 | A | 12/1999 | Elstrom |
| 6,004,339 | A | 12/1999 | Wijay |
| 6,009,347 | A | 12/1999 | Hofmann |
| 6,009,877 | A | 1/2000 | Edwards |
| 6,010,613 | A | 1/2000 | Walters et al. |
| 6,016,452 | A | 1/2000 | Kasevich |
| 6,029,090 | A | 2/2000 | Herbst |
| 6,041,252 | A | 3/2000 | Walker et al. |
| 6,043,066 | A * | 3/2000 | Mangano ............... C12M 35/02 435/173.1 |
| 6,050,994 | A | 4/2000 | Sherman |
| 6,055,453 | A | 4/2000 | Hofmann et al. |
| 6,059,780 | A | 5/2000 | Gough et al. |
| 6,066,134 | A | 5/2000 | Eggers et al. |
| 6,068,121 | A | 5/2000 | McGlinch |
| 6,068,650 | A | 5/2000 | Hofmann et al. |
| 6,071,281 | A | 6/2000 | Burnside et al. |
| 6,074,374 | A | 6/2000 | Fulton |
| 6,074,389 | A | 6/2000 | Levine et al. |
| 6,085,115 | A | 7/2000 | Weaver et al. |
| 6,090,016 | A | 7/2000 | Kuo |
| 6,090,105 | A | 7/2000 | Zepeda et al. |
| 6,090,106 | A | 7/2000 | Goble et al. |
| 1,430,015 | A | 8/2000 | Himbert et al. |
| 6,096,035 | A | 8/2000 | Sodhi et al. |
| 6,102,885 | A | 8/2000 | Bass |
| 6,106,521 | A | 8/2000 | Blewett et al. |
| 6,109,270 | A | 8/2000 | Mah et al. |
| 6,110,192 | A | 8/2000 | Ravenscroft et al. |
| 6,113,593 | A | 9/2000 | Tu et al. |
| 6,116,330 | A | 9/2000 | Salyer |
| 6,120,493 | A | 9/2000 | Hofmann |
| 6,122,599 | A | 9/2000 | Mehta |
| 6,123,701 | A | 9/2000 | Nezhat |
| 6,132,397 | A | 10/2000 | Davis et al. |
| 6,132,419 | A | 10/2000 | Hofmann |
| 6,134,460 | A | 10/2000 | Chance |
| 6,139,545 | A | 10/2000 | Utley et al. |
| 6,150,148 | A | 11/2000 | Nanda et al. |
| 6,159,163 | A | 12/2000 | Strauss et al. |
| 6,178,354 | B1 | 1/2001 | Gibson |
| 1,437,941 | A1 | 2/2001 | Frattini |
| 6,193,715 | B1 | 2/2001 | Wrublewski et al. |
| 6,198,970 | B1 | 3/2001 | Freed et al. |
| 6,200,314 | B1 | 3/2001 | Sherman |
| 6,208,893 | B1 | 3/2001 | Hofmann |
| 6,210,402 | B1 | 4/2001 | Olsen et al. |
| 6,212,433 | B1 | 4/2001 | Behl |
| 6,216,034 | B1 | 4/2001 | Hofmann et al. |
| 6,219,577 | B1 | 4/2001 | Brown, III et al. |
| 1,442,697 | A1 | 5/2001 | Hajianpour |
| 6,233,490 | B1 | 5/2001 | Kasevich |
| 6,235,023 | B1 | 5/2001 | Lee et al. |
| 1,443,360 | A1 | 6/2001 | Haberland |
| 6,241,702 | B1 | 6/2001 | Lundquist et al. |
| 6,241,725 | B1 | 6/2001 | Cosman |
| 1,445,198 | A1 | 7/2001 | Frattini |
| 6,258,100 | B1 | 7/2001 | Alferness et al. |
| 6,261,831 | B1 | 7/2001 | Agee |
| 6,277,114 | B1 | 8/2001 | Bullivant et al. |
| 6,278,895 | B1 | 8/2001 | Bernard |
| 6,280,441 | B1 | 8/2001 | Ryan |
| 6,283,988 | B1 | 9/2001 | Laufer et al. |
| 6,283,989 | B1 | 9/2001 | Laufer et al. |
| 6,284,140 | B1 | 9/2001 | Sommermeyer et al. |
| 6,287,293 | B1 | 9/2001 | Jones et al. |
| 6,287,304 | B1 | 9/2001 | Eggers et al. |
| 6,296,636 | B1 | 10/2001 | Cheng et al. |
| 6,298,726 | B1 | 10/2001 | Adachi et al. |
| 6,299,633 | B1 | 10/2001 | Laufer |
| 6,300,108 | B1 | 10/2001 | Rubinsky et al. |
| 1,450,391 | A1 | 11/2001 | Hunt et al. |
| 6,312,428 | B1 | 11/2001 | Eggers et al. |
| 6,326,177 | B1 | 12/2001 | Schoenbach et al. |
| 6,327,505 | B1 | 12/2001 | Medhkour et al. |
| 6,328,689 | B1 | 12/2001 | Gonzalez et al. |
| 6,347,247 | B1 | 2/2002 | Dev et al. |
| 6,349,233 | B1 | 2/2002 | Adams |
| 6,351,674 | B2 | 2/2002 | Silverstone |
| 6,375,634 | B1 | 4/2002 | Carroll |
| 6,387,671 | B1 | 5/2002 | Rubinsky et al. |
| 6,398,779 | B1 | 6/2002 | Buysse et al. |
| 6,403,348 | B1 | 6/2002 | Rubinsky et al. |
| 6,405,732 | B1 | 6/2002 | Edwards et al. |
| 6,411,852 | B1 | 6/2002 | Danek et al. |
| 6,419,674 | B1 | 7/2002 | Bowser et al. |
| 6,428,802 | B1 | 8/2002 | Atala |
| 6,443,952 | B1 | 9/2002 | Mulier et al. |
| 6,463,331 | B1 | 10/2002 | Edwards |
| 6,470,211 | B1 | 10/2002 | Ideker et al. |
| 6,482,221 | B1 | 11/2002 | Hebert et al. |
| 6,482,619 | B1 | 11/2002 | Rubinsky et al. |
| 6,485,487 | B1 | 11/2002 | Sherman |

(56) References Cited

U.S. PATENT DOCUMENTS

| | | | |
|---|---|---|---|
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,733,516 B2 | 5/2004 | Simons et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 * | 3/2005 | Dev ............... A61N 1/325 607/2 |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 * | 5/2011 | Demarais ............ A61N 1/0514 604/21 |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |

(56) References Cited

U.S. PATENT DOCUMENTS

| | | |
|---|---|---|
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,506,564 B2 | 8/2013 | Long et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 | 8/2016 | Callas et al. |
| 9,598,691 B2 | 3/2017 | Davalos |
| 9,764,145 B2 | 9/2017 | Callas et al. |
| 9,867,652 B2 | 1/2018 | Sano et al. |
| 9,943,599 B2 | 4/2018 | Gehl et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 10,448,989 B2 | 10/2019 | Arena et al. |
| 10,470,822 B2 | 11/2019 | Garcia et al. |
| 10,471,254 B2 | 11/2019 | Sano et al. |
| 10,537,379 B2 | 1/2020 | Sano et al. |
| 10,694,972 B2 | 6/2020 | Davalos et al. |
| 10,702,326 B2 | 7/2020 | Neal et al. |
| 10,828,085 B2 | 11/2020 | Davalos et al. |
| 10,828,086 B2 | 11/2020 | Davalos et al. |
| 10,959,772 B2 | 3/2021 | Davalos et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0104318 A1 | 8/2002 | Jaafar et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Edward |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Mala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0153960 A1 | 8/2003 | Chornenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193042 A1 | 9/2004 | Scampini et al. |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0004507 A1 | 1/2005 | Schroeppel et al. |
| 2005/0010209 A1 | 1/2005 | Lee et al. |
| 2005/0010259 A1 | 1/2005 | Gerber |
| 2005/0013870 A1 | 1/2005 | Freyman et al. |

(56) References Cited

U.S. PATENT DOCUMENTS

| | | |
|---|---|---|
| 2005/0020965 A1 | 1/2005 | Rioux et al. |
| 2005/0043726 A1 | 2/2005 | McHale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129760 A1 | 6/2007 | Demarais et al. |
| 2007/0151848 A1 | 7/2007 | Novak et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bomzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0065062 A1 | 3/2008 | Leung et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326366 A1 | 12/2009 | Krieg |
| 2009/0326436 A1 | 12/2009 | Rubinsky et al. |
| 2009/0326570 A1 | 12/2009 | Brown |

(56) References Cited

U.S. PATENT DOCUMENTS

| | | |
|---|---|---|
| 2010/0004623 A1 | 1/2010 | Hamilton, Jr. et al. |
| 2010/0006441 A1 | 1/2010 | Renaud et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1* | 10/2010 | Davalos ............... A61N 1/0412 600/411 |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0092973 A1 | 4/2011 | Nuccitelli et al. |
| 2011/0106221 A1* | 5/2011 | Neal, II ................. A61B 18/12 607/74 |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0166499 A1 | 7/2011 | Demarais et al. |
| 2011/0176037 A1 | 7/2011 | Benkley, III |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0030239 A1 | 1/2013 | Weyh et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Li et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0017218 A1 | 1/2014 | Scott et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0152504 A1 | 6/2015 | Lin |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320478 A1 | 11/2015 | Cosman, Jr. et al. |
| 2015/0320488 A1 | 11/2015 | Moshe et al. |
| 2015/0320999 A1 | 11/2015 | Nuccitelli et al. |
| 2015/0327944 A1 | 11/2015 | Robert et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338758 A9 | 11/2016 | Davalos et al. |
| 2016/0338761 A1 | 11/2016 | Chornenky et al. |
| 2016/0354142 A1 | 12/2016 | Pearson et al. |
| 2016/0367310 A1 | 12/2016 | Onik et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0360326 A1 | 12/2017 | Davalos et al. |
| 2018/0071014 A1 | 3/2018 | Neal et al. |
| 2018/0125565 A1 | 5/2018 | Sano et al. |
| 2018/0161086 A1 | 6/2018 | Davalos et al. |
| 2019/0029749 A1 | 1/2019 | Garcia |
| 2019/0046255 A1 | 2/2019 | Davalos et al. |
| 2019/0069945 A1 | 3/2019 | Davalos et al. |
| 2019/0076528 A1 | 3/2019 | Soden et al. |
| 2019/0083169 A1 | 3/2019 | Single et al. |
| 2019/0133671 A1 | 5/2019 | Davalos et al. |
| 2019/0175248 A1 | 6/2019 | Neal, II |
| 2019/0175260 A1 | 6/2019 | Davalos |
| 2019/0223938 A1 | 7/2019 | Arena et al. |
| 2019/0232048 A1 | 8/2019 | Latouche et al. |
| 2019/0233809 A1 | 8/2019 | Neal et al. |
| 2019/0256839 A1 | 8/2019 | Neal et al. |
| 2019/0282294 A1 | 9/2019 | Davalos et al. |
| 2019/0328445 A1 | 10/2019 | Sano et al. |
| 2019/0351224 A1 | 11/2019 | Sano et al. |
| 2019/0376055 A1 | 12/2019 | Davalos et al. |
| 2020/0046432 A1 | 2/2020 | Garcia et al. |
| 2020/0046967 A1 | 2/2020 | Ivey et al. |
| 2020/0093541 A9 | 3/2020 | Neal et al. |
| 2020/0197073 A1 | 6/2020 | Sano et al. |
| 2020/0260987 A1 | 8/2020 | Davalos et al. |
| 2020/0323576 A1 | 10/2020 | Neal et al. |
| 2020/0405373 A1 | 12/2020 | O'Brien et al. |

(56) References Cited

U.S. PATENT DOCUMENTS

| | | | |
|---|---|---|---|
| 2021/0022795 A1 | 1/2021 | Davalos et al. | |
| 2021/0023362 A1 | 1/2021 | Lorenzo et al. | |
| 2021/0052882 A1 | 2/2021 | Wasson et al. | |
| 2021/0113265 A1 | 4/2021 | D'Agostino et al. | |
| 2021/0137410 A1 | 5/2021 | O'Brien et al. | |
| 2021/0186600 A1 | 6/2021 | Davalos et al. | |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| DE | 863111tr | 1/1953 |
| DE | 4000893tr | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2280741 A1 | 2/2011 |
| EP | 2381829 A1 | 11/2011 |
| EP | 2413833 A1 | 2/2012 |
| EP | 2488251 A2 | 8/2012 |
| EP | 2642937 A2 | 10/2013 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| EP | 3143124 A1 | 3/2017 |
| EP | 3852868 A1 | 7/2021 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| JP | 2014501574 A | 1/2014 |
| JP | 3594901 B2 | 10/2019 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012071526 A2 | 5/2012 |
| WO | 2012088149 A | 6/2012 |
| WO | 2015175570 A1 | 11/2015 |
| WO | 2016100325 A1 | 6/2016 |

(56) References Cited

FOREIGN PATENT DOCUMENTS

WO 2016164930 A1 10/2016
WO 20200061192 A1 3/2020

OTHER PUBLICATIONS

Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Zhang, Y., et al., MR imaging to assess immediate response to irreversible electroporation for targeted ablation of liver tissues: preclinical feasibility studies in a rodent model. Radiology, 2010. 256(2): p. 424-32.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp 894-899.
Precision Office Tuna System, When Patient Satisfaction is Your Goal, VidaMed 2001.
Pucihar et al., "Numerical determination of transmembrane voltage induced on irregularly shaped cells." Annals of Biomedical Engineering, vol. 34, pp. 642-652 (2006).
Rajagopal, V. and S.G. Rockson, Coronary restenosis: a review of mechanisms and management, The American Journal of Medicine, 2003, 115(7): p. 547-553.
Reberšek, M. and D. Miklavčič, "Advantages and Disadvantages of Different Concepts of Electroporation Pulse Generation," AUTOMATIKA 52(2011) 1, 12-19.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
Salford, L.G., et al., "A new brain tumour therapy combining bleomycin with in vivo electropermeabilization", Biochem. Biophys Res Commun., 194(2): 938-943 (1993).

Salmanzadeh et al., "Investigating dielectric properties of different stages of syngeneic murine ovarian cancer cells" Biomicrofluidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sano et al., "Contactless Dielectrophoretic Spectroscopy: Examination of the Dielectric Properties of Cells Found in Blood " Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Dancer Cells from Dilute Whole Blood Samples." Biosensors & Bioelectronics, 8 pages (2011).
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Saur et al., "CXCR4 expression increases liver and lung metastasis in a mouse model of pancreatic cancer." Gastroenterology, vol. 129, pp. 1237-1250 (2005).
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Sel, D. et al. Sequential finite element model of tissue electropermeabilization. IEEE Transactions on Biomedical Engineering 52, 816-827, doi:10 1109/tbme.2005.845212 (2005).
Sei, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Sharma, A. , et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al., Percutaneous ethanol injection therapy for hepatocellular carcinoma: results in 146 patients. AJR, 1993, 160: p. 1023-8.
Szot et al., "3D in vitro bioengineered tumors based on collagen I hydrogels." Biomaterials vol. 32, pp. 7905-7912 (2011).
Talele, S., et al., "Modelling single cell electroporation with bipolar pulse parameters and dynamic pore radii". Jounal of Electrostatics, 68(3): p. 261-274 (2010).
Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.

(56) References Cited

OTHER PUBLICATIONS

Thompson, et al., To determine whether the temperature of 2% lignocaine gel affects the initial discomfort which may be associated with its instillation into the male urethra, BJU International (1999), 84, 1035-1037.
Thomson, K. R., et al., "Investigation of the Safety of Irreversible Electroporation in Humans" J. Vascular Int. Radiol. 22 (5), 611-621 (2011).
TUNA—Suggested Local Anesthesia Guidelines, no date available.
Verbridge et al., "Oxygen-Controlled Three-Dimensional Cultures to Analyze Tumor Angiogenesis." Tissue Engineering, Part A vol. 16, pp. 2133-2141 (2010).
Vernier, P.T., et al., "Nanoelectropulse-driven membrane perturbation and small molecule permeabilization", Bmc Cell Biology, 7 (2006).
Vidamed, Inc., Transurethral Needle Ablation (TUNA): Highlights from Worldwide Clinical Studies, Vidamed's Office TUNA System, 2001.
Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.
Weaver et al., "A brief overview of electroporation pulse strength-duration space: A region where additional intracellular effects are expected." Bioelectrochemistry vol. 87, pp. 236-243 (2012).
Weaver, Electroporation: A General Phenomenon for Manipulating Cells and Tissues, Journal of Cellular Biochemistry, 51: 426-435, 1993.
Weaver, et al.. Theory of Electroporation: A Review, Bioelectrochemistry and Bioenergetics, vol. 41, pp. 136-160, 1996.
Weaver, J. C., Electroporation of biological membranes from multicellular to nano scales, IEEE Trns. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011).
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/S00270-014-0905-2.
Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavčič, et al.. The Importance of Electric Field Distribution for Effective in Vivo Electroporation of Tissues, Biophysical Journal, vol. 74, May 1998, pp. 2152-2158.
Miller, L., et al.. Cancer cells ablation with irreversible electroporation, Technology in Cancer Research and Treatment 4 (2005) 699-706.
Mir et al., "Mechanisms of Electrochemotherapy" Advanced Drug Delivery Reviews 35:107-118 (1999).
Mir, et al.. Effective Treatment of Cutaneous and Subcutaneous Malignant Tumours by Electrochemotherapy, British Journal of Cancer, vol. 77, No. 12, pp. 2336-2342, 1998.
Mir, et al.. Electrochemotherapy Potentiation of Antitumour Effect of Bleomycin by Local Electric Pulses, European Journal of Cancer, vol. 27, No. 1, pp. 68-72, 1991.
Mir, et al.. Electrochemotherapy, a Novel Antitumor Treatment: First Clinical Trial, C.R. Acad. Sci. Paris, Ser. Ill, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al.. Electric Pulse-Mediated Gene Delivery to Various Animal Tissues, in Advances in Genetics, Academic Press, 2005, p. 83-114.
Mir, Therapeutic Perspectives of In Vivo Cell Electropermeabilization, Bioelectrochemistry, vol. 53, pp. 1-10, 2000.
Mulhall et al., "Cancer, pre-cancer and normal oral cells distinguished by dielectrophoresis." Analytical and Bioanalytical Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Naslund, Michael J., Transurethral Needle Ablation of the Prostate, Urology, vol. 50, No. 2, Aug. 1997.
Neal II et al., "A Case Report on the Successful Treatment of a Large Soft-Tissue Sarcoma with Irreversible Electroporation," Journal of Clinical Oncology, 29, pp. 1-6, 2011.
Neal II, R. E , et al., "Experimental characterization and numerical modeling of tissue electrical conductivity during pulsed electric fields for irreversible electroporation treatment planning," IEEE Trans Biomed Eng., vol. 59:4, pp. 1076-1085. Epub 2012 Jan. 6, 2012.
Neal II, R. E., et al., "Successful Treatment of a Large Soft Tissue Sarcoma with Irreversible Electroporation", Journal of Clinical Oncology, 29:13, e372-e377 (2011).
Neal II, R.E., et al., "Treatment of breast cancer through the application of irreversible electroporation using a novel minimally invasive single needle electrode." Breast Cancer Research and Treatment, 2010 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
Neumann, et al.. Gene Transfer into Mouse Lyoma Cells by Electroporation in High Electric Fields, J. Embo., vol. 1, No 7, pp. 841-845, 1982.
Neumann, et al., Permeability Changes Induced by Electric Impulses in Vesicular Membranes, J. Membrane Biol., vol. 10, pp. 279-290, 1972.
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Okino, et al., Effects of High-Voltage Electrical Impulse and an Anticancer Drug on In Vivo Growing Tumors, Japanese Journal of Cancer Research, vol. 78, pp. 1319-1321,1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.

(56) References Cited

OTHER PUBLICATIONS

Onik, G. and B. Rubinsky, eds. "Irreversible Electroporation: First Patient Experience Focal Therapy of Prostate Dancer. Irreversible Electroporation", ed B. Rubinsky 2010, Springer Berlin Heidelberg, pp. 235-247.

Onik, G., P. Mikus, and B. Rubinsky, "Irreversible electroporation: implications for prostate ablation." Technol Cancer Res Treat, 2007. 6(4): p. 295-300.

Organ, L.W., Electrophysiological principles of radiofrequency lesion making, Apply. Neurophysiol., 1976. 39: p. 69-76.

Ott, H. C. et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.

Paszek et al., "Tensional homeostasis and the malignant phenotype." Cancer Cell, vol. 8, pp. 241-254 (2005).

Pavselj, N et al. The course of tissue permeabilization studied on a mathematical model of a subcutaneous tumor in small animals. IEEE Trans Biomed Eng 52, 1373-1381 (2005).

PCT International Preliminary Report on Patentability of Corresponding International Application No. PCT/2011/062067, dated May 28, 2013.

PCT International Preliminary Report on Patentability of Corresponding International Application No. PCT/2011/066239, dated Jun. 25, 2013.

PCT International Search Report (dated Aug. 2, 2011), Written Opinion (dated Aug. 2, 2011), and International Preliminary Report an Patentability (dated Apr. 17, 2012) of PCT/US10/53077.

PCT International Search Report (dated Aug. 22, 2012), and Written Opinion (dated Aug. 22, 2012) of PCT/US11/66239.

PCT International Search Report (dated Aug. 26, 2005), Written Opinion (dated Aug. 26, 2005), and International Preliminary Report on Patentability (dated Jun. 26, 2006) of PCT/US2004/043477.

PCT International Search Report (dated Jan. 19, 2010), Written Opinion (dated Jan. 19, 2010), and International Preliminary Repor an Patentability (dated Jan. 4, 2010) of PCT/US09/62806, 15 pgs.

PCT International Search Report (dated Jul. 15, 2010), Written Opinion (dated Jul. 15, 2010), and International Preliminary Report an Patentability (dated Oct. 11, 2011) from PCT/US2010/030629.

PCT International Search Report (dated Jul. 9, 2009), Written Opinion (dated Jul. 9, 2009), and International Preliminary Report or Patentability (dated Nov. 2, 2010) of PCT/US2009/042100.

PCT International Search Report and Written Opinion (dated Jul. 25, 2012) of PCT/US2011/062067.

PCT International Search Report, 4 pgs, (dated Jul. 30, 2010), Written Opinion, 7 pgs, (dated Jul. 30, 2010), and International Preliminary Report on Patentability, 8 pgs, (dated Oct. 4, 2011) from PCT/US2010/029243.

PCT IPRP for PCT/US15/30429 (WO2015175570), dated Nov. 15, 2016.

Phillips, M., Maor, E. & Rubinsky, B. Non-Thermal Irreversible Electroporation for Tissue Decellularization. J. Biomech. Eng, doi: 10.1115/1.4001882 (2010).

Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.

Polak et al., "On the Electroporation Thresholds of Lipid Bilayers: Molecular Dynamics Simulation Investigations." The Journal of Membrane Biology, vol. 246, pp. 843-850 (2013).

Agerholm-Larsen, B., et al., "Preclinical Validation of Electrochemotherapy as an Effective Treatment for Brain Tumors", Cancer Research 71: 3753-3762 (2011).

Alberts et al., "Molecular Biology of the Cell," 3rd edition, Garland Science, New York, 1994, 1 page.

Al-Sakere, B. et al., 2007, "Tumor ablation with irreversible electroporation." PLoS ONE 2.

Amasha, et al., Quantitative Assessment of Impedance Tomography for Temperature Measurements in Microwave Hyperthermia, Clin. Phys. Physiol. Meas., 1998, Suppl. A, 49-53.

Andreason, Electroporation as a Technique for the Transfer of Macromolecules into Mammalian Cell Lines, J. Tiss. Cult. Meth., 15:56-62, 1993.

Appelbaum, L., et al., "US Findings after Irreversible Electroporation Ablation: Radiologic-Pathologic Correlation" Radiology 262(1), 117-125 (2012).

Arena et al. "High-Frequency Irreversible Electroporation (H-FIRE) for Non-thermal Ablation without Muscle Contraction." Biomed. Eng. Online, vol. 10, 20 pages (2011).

Arena, C.B., et al., "A three-dimensional in vitro tumor platform for modeling therapeutic irreversible electroporation." Biophysical Journal, 2012.103(9): p. 2033-2042.

Arena, Christopher B., et al., "Towards the development of latent heat storage electrodes for electroporation-based therapies", Applied Physics Letters, 101, 083902 (2012).

Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.

Asami et al., "Dielectric properties of mouse lymphocytes and erythrocytes." Biochimica et Biophysica Acta (BBA)-Molecular Cell Research, 1010(1989) pp. 49-55.

Bagla, S. and Papadouris, D., "Percutaneous Irreversible Electroporation of Surgically Unresectable Pancreatic Dancer: A Case Report" J. Vascular Int. Radiol. 23(1), 142-145 (2012).

Baker, et al., Calcium-Dependent Exocytosis in Bovine Adrenal Medullary Cells with Leaky Plasma Membranes, Nature, vol. 276, pp. 620-622, 1978.

Ball, C., K.R. Thomson, and H. Kavnoudias, "Irreversible electroporation: a new challenge in "out of-operating theater" anesthesia." Anesth Analg, 2010.110(5): p. 1305-9.

Bancroft, et al., Design of a Flow Perfusion Bioreactor System for Bone Tissue-Engineering Applications, Tissue Engineering, vol. 9, No. 3, 2003, p. 549-554.

Baptista et al., "The Use of Whole Organ Decellularization for the Generation of a Vascularized Liver Organoid," Heptatology, vol. 53, No. 2, pp. 604-617 (2011).

Barber, Electrical Impedance Tomography Applied Potential Tomography, Advances in Biomedical Engineering, Beneken and Thevenin, eds , IOS Press, pp. 165-173, 1993.

Beebe, S.J., et al., "Diverse effects of nanosecond pulsed electric fields on cells and tissues", DNA and Cell Biology, 22(12): 785-796 (2003).

Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.

Ben-David, E., et al., "Characterization of Irreversible Electroporation Ablation in In Vivo Procine Liver" Am. J. Roentgenol. 198(1), W62-W68 (2012).

Blad, et al., Impedance Spectra of Tumour Tissue in Comparison with Normal Tissue; a Possible Clinical Application for Electrical Impedance Tomography, Physiol. Meas. 17 (1996) A105-A115.

Bolland, F., et al., "Development and characterisation of a full-thickness acellular porcine bladder matrix for tissue engineering". Biomaterials, Elsevier Science Publishers, Barking, GB, vol. 28, No. 6, Nov. 28, 2006, pp. 1061-1070.

Boone, K., Barber, D. & Brown, B. Review—Imaging with electricity: report of the European Concerted Action on Impedance Tomography. J. Med. Eng. Technol. 21, 201-232 (1997).

Bower et al., "Irreversible electroporation of the pancreas: definitive local therapy without systemic effects." Journal of surgical oncology, 2011. 104(1): p. 22-28.

BPH Management Strategies: Improving Patient Satisfaction, Urology Times, May 2001, vol. 29, Supplement 1.

Brown, et al., Blood Flow Imaging Using Electrical Impedance Tomography, Clin. Phys. Physiol. Meas., 1992, vol. 13, Suppl. A, 175-179.

Brown, S.G., Phototherapy of tumors. World J. Surgery, 1983. 7: p. 700-9.

(56) References Cited

OTHER PUBLICATIONS

Cannon et al., "Safety and early efficacy of irreversible electroporation for hepatic tumors in proximity to vital structures " Journal of Surgical Oncology, 6 pages (2012).
Carpenter A.E et al., "CellProfiler: image analysis software for identifying and quantifying cell phenotypes." Genome Biol. 2006; 7(10): R100. Published online Oct. 31, 2006, 11 pages.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal ol the International Hepato Pancreato Biliary Association, 2010.12(5): p. 348-351.
Chen et al., "Classification of cell types using a microfluidic device for mechanical and electrical measurement on single cells" Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W.,et al, "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, IEEE Transactions on Biomedical Engineering, vol. 41, No. 8, Aug. 1994.
Co-Pending U.S. Appl. No. 10/571,162, filed Oct. 18, 2006 (published as 2007/0043345 on Feb. 22, 2007).
Co-Pending U.S. Appl. No. 12/432,295, filed Apr. 29, 2009.
Co-Pending Application No. 12/609,1/9, filed Oct. 30, 2009.
Co-Pending U.S. Appl. No. 12/751,826, filed Mar. 31, 2010 (published as 2010/0250209 on Sep. 30, 2010).
Co-Pending U.S. Appl. No. 12/751,854, filed Mar. 31, 2010 (published as 2010/0249771 on Sep. 30, 2010).
Co-Pending U.S. Appl. No. 12/757,901, filed Apr. 9, 2010.
Co-Pending U.S. Appl. No. 12/757,901, Issued as U.S. Pat. No. 8,926,606 on Jan. 6, 2015, 42 pages.
Co-Pending U.S. Appl. No. 12/906,923, filed Oct. 18, 2010.
Co-Pending U.S. Appl. No. 14/558,631, filed Dec. 2, 2014.
Co-Pending U.S. Appl. No. 14/686,380, filed Apr. 14, 2015 and Published as US 2015/0289923 on Oct. 15, 2015.
Co-Pending U.S. Appl. No. 14/808,679, Restriction Requirement dated Mar. 19, 2018, 7 pages.
Co-Pending U.S. Appl. No. 14/808,679, filed Jul. 24, 2015 and Published as U.S. Publication No. 2015/0327944 on Nov. 19, 2015.
Heller, et al., Clinical Applications of Electrochemotherapy, Advanced Drug Delivery Reviews, vol. 35, pp. 119-129, 1999.
Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", Plos One, Aug. 2012, 7:8, e42817.
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. iii114.
Ho, et al.. Electroporation of Cell Membranes: A Review, Critical Reviews in Biotechnology, 16(4): 349-362, 1996.
Holder, et al.. Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical Bl, pp. 512-519, 1999.
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta-General Subjects, vol. 1800, pp. 1210-1219 (2010).
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
Ivanuša, et al., MRI Macromolecular Contrast Agents as Indicators of Changed Tumor Blood Flow, Radiol. Oncol. 2001; 35(2): 139-47.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra,"Bioimpedance monitoring for physicians: an overview." Biomedical Applications Group, 35 pages (2002).
Jarm et al., "Antivascular effects of electrochemotherapy: implications in treatment of bleeding metastases." Expert Rev Anticancer Ther. vol. 10, pp. 729-746 (2010).
Jaroszeski, et al.. In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Jossinet et al., Electrical Impedance Endo-Tomography: Imaging Tissue From Inside, IEEE Transactions on Medical Imaging, vol. 21, No. 6, Jun. 2002, pp. 560-565.
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)-Biomembranes, 471 (1977) pp. 227-242.
Kinosita et al., "Electroporation of cell membrane visualized under a pulsed-laser fluorescence microscope." Biophysical Journal, vol. 53, pp. 1015-1019 (1988).
Kinosita, et al.. Hemolysis of Human Erythrocytes by a Transient Electric Field, Proc. Natl. Acad. Sci. USA, vol. 74, No. 5, pp. 1923-1927, 1977.
Kirson et al., "Alternating electric fields arrest cell proliferation in animal tumor models and human brain tumors." Proceedings of the National Academy of Sciences vol. 104, p. 10152-10157 (2007).
Kotnik and Miklavcic, "Theoretical evaluation of voltage inducement on internal membranes of biological cells exposed to electric fields." Biophysical Journal, vol. 90(2), pp. 480-491 (2006).
Kotnik et al., "Sensitivity of transmembrane voltage induced by applied electric fields—A theoretical analysis", Bioelectrochemistry and Bioenergetics, vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta-Biomembranes, 1614(2): p. 193-200 (2003).

(56) References Cited

OTHER PUBLICATIONS

Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).

Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).

Laufer et al., "Electrical impedance characterization of normal and cancerous human hepatic tissue." Physiological Measurement, vol. 31, pp. 995-1009 (2010).

Lebar et al., "Inter-pulse interval between rectangular voltage pulses affects electroporation threshold of artificial lipid bilayers." IEEE Transactions on NanoBioscience, vol. 1 (2002) pp. 116-120.

Lee, E. W. et al. Advanced Hepatic Ablation Technique for Creating Complete Cell Death : Irreversible Electroporation. Radiology 255, 426-433, doi:10.1148/radiol. 10090337 (2010).

Lee, E.W., et al., "Imaging guided percutaneous irreversible electroporation: ultrasound and immunohistological correlation", Technol Cancer Res Treat 6: 287-294 (2007).

Li, W., et al., "The Effects of Irreversible Electroporation (IRE) on Nerves" PloS One, Apr. 2011, 6(4), e18831.

Liu, et al.. Measurement of Pharyngeal Transit Time by Electrical Impedance Tomography, Clin. Phys. Physiol. Meas., 1992, vol. 13, Suppl. A, pp. 197-200.

Long, G., et al., "Targeted Tissue Ablation With Nanosecond Pulses", Ieee Transactions on Biomedical Engineering, 58(8) (2011).

Lundqvist, et al., Altering the Biochemical State of Individual Cultured Cells and Organelles with Ultramicroelectrodes, Proc. Natl. Acad. Sci. USA, vol. 95, p. 10356-10360, Sep. 1998.

Lurquin, Gene Transfer by Electroporation, Molecular Biotechnology, vol. 7, 1997.

Lynn, et al., A New Method for the Generation and Use of Focused Ultrasound in Experimental Biology, The Journal of General Physiology, vol. 26, 179-193, 1942.

Maček Lebar and Miklavčič, "Cell electropermeabilization to small molecules in vitro: control by pulse parameters." Radiology and Oncology, vol. 35(3), pp. 193-202 (2001).

Mahmood, F., et al., "Diffusion-Weighted MRI for Verification of Electroporation-Based Treatments", Journal of Membrane Biology 240: 131-138 (2011).

Mahnic-Kalamiza, S., et al., "Educational application for visualization and analysis of electric field strength in multiple electrode electroporation," BMC Med Educ, vol. 12, p. 102, 2012.

Malpica et al., "Grading ovarian serous carcinoma using a two-tier system." The American Journal of Surgical Pathology, vol. 28, pp. 496-504 (2004).

Maor et al., The Effect of Irreversible Electroporation on Blood Vessels, Tech. in Cancer Res. and Treatment, vol. 6, No. 4, Aug. 2007, pp. 307-312.

Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.

Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.

Marszalek et al., "Schwan equation and transmembrane potential induced by alternating electric field." Biophysical Journal, vol. 58, pp. 1053-1058 (1990).

Martin, n.R.C.G., et al., "Irreversible electroporation therapy in the management of locally advanced pancreatic adenocarcinoma." Journal of the American College of Surgeons, 2012. 215(3): p. 361-369.

Dean, Nonviral Gene Transfer to Skeletal, Smooth, and Cardiac Muscle in Living Animals, Am J. Physiol Cell Physiol 289: 233-245, 2005.

Demirbas, M. F., "Thermal Energy Storage and Phase Change Materials: An Overview" Energy Sources Part B 1(1), 35-95 (2006).

Dev, et al., Medical Applications of Electroporation, IEEE Transactions of Plasma Science, vol. 28, No. 1, pp. 206-223, Feb. 2000.

Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.

Duraiswami, et al., Boundary Element Techniques for Efficient 2-D and 3-D Electrical Impedance Tomography, Chemical Engineering Science, vol. 52, No. 13, pp. 2185-2196, 1997.

Duraiswami, et al., Efficient 2D and 3D Electrical Impedance Tomography Using Dual Reciprocity Boundary Element Techniques, Engineering Analysis with Boundary Elements 22, (1998) 13-31.

Duraiswami, et al., Solution of Electrical Impedance Tomography Equations Using Boundary Element Methods, Boundary Element Technology XII, 1997, pp. 226-237.

Edd, J., et al., In-Vivo Results of a New Focal Tissue Ablation Technique: Irreversible Electroporaton, IEEE Trans. Biomed. Eng. 53 (2006) p. 1409-1415.

Edd, J.F, et al., 2007, "Mathematical modeling of irreversible electroporation for treatment planning.", Technology in Cancer Research and Treatment, 6:275-286.

Ellis TL, Garcia PA, Rossmeisl JH, Jr., Henao-Guerrero N, Robertson J, et al., "Nonthermal irreversible electroporation tor intracranial surgical applications. Laboratory investigation", J Neurosurg 114: 681-688 (2011).

Eppich et al., "Pulsed electric fields for selection of hematopoietic cells and depletion of tumor cell contaminants." Nature Biotechnology 18, pp. 882-887 (2000).

Erez, et al.. Controlled Destruction and Temperature Distributions in Biological Tissues Subjected to Monoactive Electrocoagulation, Transactions of the ASME: Journal of Mechanical Design, vol. 102, Feb. 1980.

Ermolina et al., "Study of normal and malignant white blood cells by time domain dielectric spectroscopy." IEEE Transactions on Dielectrics and Electrical Insulation, 8 (2001) pp. 253-261.

Esser, A.T., et al., "Towards solid tumor treatment by irreversible electroporation: intrinsic redistribution of fields and currents in tissue" Technol Cancer Res Treat, 6(4): p. 261-74 (2007).

Esser, A.T., et al., "Towards Solid Tumor Treatment by Nanosecond Pulsed Electric Fields". Technology in Cancer Research & Treatment, 8(4): p. 289-306 (2009).

Extended European Search Report. dated May 11, 2012. PCT/U.S. Pat. No. 2009042100 from EP 09739678.2.

Faroja, M., et al., "Irreversible Electroporation Ablation: Is the entire Damage Nonthermal?", Radiology, 266(2), 462-470 (2013).

Fischbach et al., "Engineering tumors with 3D scaffolds." Nat Meth 4, pp. 855-860 (2007).

Flanagan et al., "Unique dielectric properties distinguish stem cells and their differentiated progeny." Stem Cells, vol. 26, pp. 656-665 (2008).

Fong et al., "Modeling Ewing sarcoma tumors in vitro with 3D scaffolds." Proceedings of the National Academy of Sciences vol. 110, pp. 6500-6505 (2013).

Foster RS, "High-intensity focused ultrasound in the treatment of prostatic disease", European Urology, 1993, vol. 23 Suppl 1, pp. 29-33.

Foster, R.S., et al., Production of Prostatic Lesions in Canines Using Transrectally Administered High-Intensity Focused Ultrasound. Eur. Urol, 1993; 23: 330-336.

Fox, et al., Sampling Conductivity Images via MCMC, Mathematics Department, Auckland University, New Zealand, May 1997.

Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).

Garcia et al., "Irreversible electroporation (IRE) to treat brain cancer." ASME Summer Bioengineering Conference, Marco Island, FL, Jun. 25-29, 2008.

Garcia P.A., et al., "7.0-T Magnetic Resonance Imaging Characterization of Acute Blood-Brain-Barrier Disruption Achieved with Intracranial Irreversible Electroporation", Plos One, Nov. 2012, 7:11, e50482.

Garcia P.A., et al., "Pilot study of irreversible electroporation for intracranial surgery", Conf Proc IEEE Eng Med Biol Soc, 2009:6513-6516, 2009.

(56) References Cited

OTHER PUBLICATIONS

Garcia PA, Rossmeisl JH, Jr., Neal RE, 2nd, Ellis TL, Davalos RV, "A Parametric Study Delineating Irreversible Electroporation from Thermal Damage Based on a Minimally Invasive Intracranial Procedure", Biomed Eng Online 10: 34 (2011).
Garcia, p. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Garcia, P. et al. Intracranial nonthermal irreversible electroporation: in vivo analysis. J Membr Biol 236, 127-136 (2010).
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).
Gauger, et al., A Study of Dielectric Membrane Breakdown in the Fucus Egg, J. Membrane Biol., vol. 48, No. 3, pp. 249-264, 1979.
Gehl, et al., In Vivo Electroporation of Skeletal Muscle: Threshold, Efficacy and Relation to Electric Field Distribution, Biochimica et Biphysica Acta 1428, 1999, pp. 233-240.
Gençer, et al., Electrical Impedance Tomography: Induced-Current Imaging Achieved with a Multiple Coil System, IEEE Transactions on Biomedical Engineering, vol. 43, No. 2, Feb. 1996.
Gilbert, et al., Novel Electrode Designs for Electrochemotherapy, Biochimica et Biophysica Acta 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa et al., "Dielectric spectroscopy of single human erythrocytes at physiological ionic strength: dispersion of the cytoplasm." Biophysical Journal, vol. 71, pp. 495-506 (1996).
Glidewell, et al., The Use of Magnetic Resonance Imaging Data and the Inclusion of Anisotropic Regions in Electrical Impedance Tomography, Biomed, Sci. Instrum. 1993; 29: 251-7.
Golberg, A. and Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar T.R., et al., "Microdosimetry for conventional and supra-electroporation in cells with organelles". Biochem Biophys Res Commun, 341(4): p. 1266-76 (2006).
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions on Biomedical Engineering, vol. 42, No. 9, Sep. 1995.
Gumerov, et al., The Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Helczynska et al., "Hypoxia promotes a dedifferentiated phenotype in ductal breast carcinoma in situ." Cancer Research, vol. 63, pp. 1441-1444 (2003).
Co-Pending application No. PCT/US19/51731 filed Sep. 18, 2019.
Co-Pending application No. PCT/US19/51731 Invitation to Pay Additional Search Fees dated Oct. 28, 2019, 2 pgs.
Co-Pending Application No. PCT/US2010/029243, filed Mar. 30, 2010, published as WO 2010/117806 on Oct. 14, 2010.
Co-Pending Application No. PCT/US2015/030429, Published on Nov. 19, 2015 as WO 2015/175570.
Co-Pending U.S. Appl. No. 12/491,151, filed Jun. 24, 2009.
Co-Pending U.S. Appl. No. 13/332,133, Advisory Action dated Apr. 6, 2016, 3 pages.
Co-Pending U.S. Appl. No. 13/332,13, Amendment with RCE after Board Decision, dated Mar. 29, 2019, 16 pages.
Co-Pending U.S. Appl. No. 13/332,13, Appeal Brief and Appendices filed Aug. 15, 2017, 26 pages.
Co-Pending U.S. Appl. No. 13/332,133, Board Decision dated Jan. 29, 2019, 13 pages.
Co-Pending U.S. Appl. No. 13/332,133, Examiner's Answer to Appeal Brief dated Oct. 5, 2017, 16 pages.
Co-Pending U.S. Appl. No. 13/332,133, File History through Aug. 1, 2017, 160 pages.
Co-Pending U.S. Appl. No. 13/332,133, Final Office Action dated Dec. 26, 2014, 7 pages.
Co-Pending U.S. Appl. No. 13/332,133, Final Office Action dated Mar. 15, 2017, 17 pages.
Co-Pending U.S. Appl. No. 13/332,133, Final Office Action dated Mar. 30, 2016, 15 pages.
Co-Pending U.S. Appl. No. 13/332,133, Interview Summary dated Jan. 22, 2016, 4 pages.
Co-Pending U.S. Appl. No. 13/332,133, Non-Final Office Action dated Nov. 22, 2016, 8 pages.
Co-Pending U.S. Appl. No. 13/332,133, Non-Final Office Action dated Oct. 16, 2015, 9 pages.
Co-Pending U.S. Appl. No. 13/332,133, Non-Final Office Action dated Sep. 4, 2014, 13 pages.
Co-Pending U.S. Appl. No. 13/332,133, Notice of Allowance, dated May 31, 2019, 5 pages.
Co-Pending U.S. Appl. No. 13/332,133, Office Actions and Responses through Mar. 2018, 221 pages.
Co-Pending U.S. Appl. No. 13/332,133, Response to Final Office Action filed Jun. 29, 2016, 9 pages.
Co-Pending U.S. Appl. No. 13/332,133, Response to Final Office Action filed Mar. 26, 2015, 11 pages.
Co-Pending U.S. Appl. No. 13/332,133, Response to Non-Final Office Action filed Dec. 4, 2014, 9 pages.
Co-Pending U.S. Appl. No. 13/332,133, Response to Non-Final Office Action filed Feb. 16, 2016, 12 pages.
Co-Pending U.S. Appl. No. 13/332,133, Response to Nov. 22, 2016 Non-Final Office Action filed Feb. 21, 2017, 14 pages.
Co-Pending U.S. Appl. No. 13/332,133, filed Dec. 20, 2011.
Co-Pending U.S. Appl. No. 13/550,307, filed Jul. 16, 2012.
Co-Pending U.S. Appl. No. 13/919,640, filed Jun. 17, 2013.
Co-Pending U.S. Appl. No. 13/958,152, filed Aug. 2, 2013.
Co-Pending U.S. Appl. No. 13/989,175, filed May 23, 2013.
Co-Pending U.S. Appl. No. 14/012,832, filed Aug. 28, 2013.
Co-Pending U.S. Appl. No. 14/017,210, filed Sep. 3, 2013.
Co-Pending U.S. Appl. No. 14/627,046, filed Feb. 20, 2015.
Co-Pending U.S. Appl. No. 14/686,380, filed Apr. 14, 2015.
Co-Pending U.S. Appl. No. 14/940,863, filed Nov. 13, 2015 and Published as US 2016/0066977 on Mar. 10, 2016.
Co-Pending U.S. Appl. No. 15/011,752, filed Feb. 1, 2016.
Co-pending U.S. Appl. No. 16/152,743, filed Oct. 5, 2018.
Corovic, S., et al., "Analytical and numerical quantification and comparison of the local electric field in the tissue for different electrode configurations," Biomed Eng Online, 6, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.

(56) References Cited

OTHER PUBLICATIONS

Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 (2008).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos, et al., Theoretical Analysis of the Thermal Effects During In Vivo Tissue Electroporation, Bioelectrochemistry, vol. 61, pp. 99-107,2003.
Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, R.V., et al., "Electrical impedance tomography for imaging tissue electroporation," IEEE Transactions on Biomedical Engineering, 51, 761-767, 2004.
Davalos, Real-Time Imaging for Molecular Medicine through Electrical Impedance Tomography of Electroporation, Dissertation for Ph D. in Engineering-Mechanical Engineering, Graduate Division of University of California, Berkeley, 2002.
De Vuyst, E., et al., "In situ bipolar Electroporation for localized cell loading with reporter dyes and investigating gap functional coupling", Biophysical Journal, 94(2): p. 469-479 (2008).
Co-pending U.S. Appl. No. 15/186,653, filed Jun. 20, 2016.
Co-pending U.S. Appl. No. 15/186,653, Notice of Allowance dated Aug. 1, 2018, 7 pages.
Co-pending U.S. Appl. No. 15/186,653, Notice of Allowance dated Mar. 20, 2019, 14 pages.
Co-pending U.S. Appl. No. 15/186,653, Preliminary Amendment filed Jun. 21, 2016, 5 pages.
Co-pending U.S. Appl. No. 15/310,114, Corrected notice of allowance dated Aug. 6, 2019, 9 pages.
Co-pending U.S. Appl. No. 15/310,114, filed Nov. 10, 2016.
Co-pending U.S. Appl. No. 15/310,114, NFOA dated Mar. 6, 2019, 13 pages.
Co-pending U.S. Appl. No. 15/310,114, Non-Final Office Action dated Mar. 6, 2019 Non-Final Office Action filed Jun. 4, 2019, 153 pages.
Co-pending U.S. Appl. No. 15/310,114, Response to Mar. 6, 2019 Non-Final Office Action filed Jun. 4, 2019, 8 pages.
Co-pending U.S. Appl. No. 15/310,114, Preliminary Amendment filed Nov. 10, 2016, 9 pages.
Co-pending U.S. Appl. No. 15/423,986, filed Feb. 3, 2017.
Co-pending U.S. Appl. No. 15/424,335, filed Feb. 3, 2017.
Co-pending U.S. Appl. No. 15/843,888, filed Dec. 15, 2017.
Co-pending U.S. Appl. No. 15/843,888, Final Office-Action dated Apr. 5, 2019, 14 pgs.
Co-pending U.S. Appl. No. 15/881,414, filed Jan. 26, 2018.
Co-pending U.S. Appl. No. 16/177,745, filed Nov. 1, 2018.
Co-pending U.S. Appl. No. 16/177,745, Non-final office action dated Aug. 20, 2019, 10 pages.
Co-pending U.S. Appl. No. 16/177,745, Preliminary Amendment dated Dec. 19, 2018, 7 pages.
Co-pending U.S. Appl. No. 16/177,745, Response to Aug. 20, 2019 Non-final office action dated Nov. 20, 2019, 10 pages.
Co-pending U.S. Appl. No. 16/232,962, filed Dec. 26, 2018.
Co-pending U.S. Appl. No. 16/232,962 Non-Final office action dated Aug. 20, 2019, 9 pages.
Co-pending U.S. Appl. No. 16/232,962 Response to Aug. 20, 2019 Non-final office action dated Nov. 20, 2019, 10 pages.
Co-pending U.S. Appl. No. 16/275,429, filed Feb. 14, 2019, which published as 2019/0175260 on Jun. 13, 2019.
Co-pending U.S. Appl. No. 16/275,429 Preliminary Amendment Filed Mar. 28, 2019, 6 pages.
Co-pending U.S. Appl. No. 16/280,511, filed Feb. 20, 2019.
Co-pending U.S. Appl. No. 16/372,520 Preliminary Amendment filed Apr. 9, 2019, 7 pages.
Co-pending U.S. Appl. No. 16/372,520, filed Apr. 2, 2019, which published as 20190223938 on Jul. 25, 2019.
Co-pending U.S. Appl. No. 16/375,878, filed Apr. 5, 2019, which published on Aug. 1, 2019 as US 2019-0233809 A1.
Co-pending U.S. Appl. No. 16/375,878, Preliminary Amendment, filed Apr. 9, 2019, 9 pages.
Co-pending U.S. Appl. No. 16/443,351 filed Jun. 17, 2019 (published as 20190328445 on Oct. 31, 2019).
Co-pending U.S. Appl. No. 16/520,901, filed Jul. 24, 2019.
Co-pending U.S. Appl. No. 16/520,901, Preliminary Amendment filed Aug. 14, 2019.
Co-pending U.S. Appl. No. 16/535,451 filed Aug. 8, 2019.
Co-pending U.S. Appl. No. 16/535,451 Preliminary Amendment filed Aug. 8, 2019, 3 pages.
Co-pending U.S. Appl. No. 16/535,451 Second Preliminary Amendment filed Oct. 9, 2019, 15 pages.
Co-pending U.S. Appl. No. 16/535,451 Third Preliminary Amendment filed Nov. 5, 2019, 4 pages.
Co-pending U.S. Appl. No. 16/655,845 filed Oct. 17, 2019.
Co-pending Application No. JP 2019-133057 filed Jul. 18, 2019,155 pgs.
Co-pending Application No. JP 2019-133057 Filing receipt for application filed Jul. 18, 2019, 2 pg.
Co-pending Application No. PCT/US04/43477, filed Dec. 21, 2004.
Co-pending Application No. PCT/US09/42100, filed Apr. 29, 2009.
Co-pending Application No. PCT/US09/62806, filed Oct. 30, 2009.
Co-pending Application No. PCT/US10/30629, filed Apr. 9, 2010.
Co-pending Application No. PCT/US10/53077, filed Oct. 18, 2010.
Co-pending Application No. PCT/US11/62067, filed Nov. 23, 2011.
Co-pending Application No. PCT/US11/66239, filed Dec. 20, 2011.
Co-pending Application No. PCT/US15/30429, filed May 12, 2015.
Co-pending Application No. PCT/US15/30429, International Search Report and Written Opinion dated Oct. 16, 2015, 19 pages.
Co-pending U.S. Appl. No. 16/177,745, Response to Jan. 9, 2020 Final office action, dated Jun. 1, 2020, 11 pages.
Co-pending U.S. Appl. No. 16/210,771, Non-Final Office Action dated Sep. 3, 2020, 9 pages.
Co-pending U.S. Appl. No. 16/232,962 Applicant initiated interview summary dated Dec. 16, 2019, 3 pages.
Co-pending U.S. Appl. No. 16/232,962 Final office action dated Jan. 9, 2020, 7 pages.
Co-pending U.S. Appl. No. 16/232,962 Notice of Allowance dated Jun. 30, 2020, 7 pages.
Co-pending U.S. Appl. No. 16/232,962 Response to Jan. 9, 2020 Final office action dated Jun. 1, 2020, 8 pages.
Co-pending U.S. Appl. No. 16/375,878, Second Preliminary Amendment, filed Feb. 5, 2020, 3 pages.
Co-pending U.S. Appl. No. 16/443,351, Preliminary amendment filed Feb. 3, 2020.
Co-pending U.S. Appl. No. 16/520,901, Second Preliminary Amendment filed Feb. 4, 2020.
Co-pending application No. PCT/US19/51731 International Search Report and Written Opinion dated Feb. 20, 2020, 19 pgs.
Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.
Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).
De Senneville, B. D. et al., "MR thermometry for monitoring tumor ablation," European radiology, vol. 17, No. 9, pp. 2401-2410, 2007.

(56) References Cited

OTHER PUBLICATIONS

Frandsen, S. K., H. Gissel, P. Hojman, T. Tramm, J. Eriksen, and J. GehL Direct therapeutic applications of calcium electroporation to effectively induce tumor necrosis. Cancer Res 72:1336-41, 2012.

Garcia-Sánchez, T., A. Azan, I. Leray, J. Rosell-Ferrer, R. Bragos, and L. M. Mir, "Interpulse multifrequency electrical impedance measurements during electroporation of adherent differentiated myotubes," Bioelectrochemistry, vol. 105, pp. 123-135, 2015.

Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.

Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.

Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.

Hu, Q., et al., "Simulations of transient membrane behavior in cells subjected to a high-intensity ultrashort electric pulse". Physical Review E, 71(3) (2005).

Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.

Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).

Jordan, D.W., et al., "Effect of pulsed, high-power radiofrequency radiation on electroporation of mammalian cells". Ieee Transactions on Plasma Science, 32(4): p. 1573-1578 (2004).

Katsuki, S., et al., "Biological effects of narrow band pulsed electric fields", Ieee Transactions on Dielectrics and Electrical Insulation,. 14(3): p. 663-668 (2007).

Kolb, J.F., et al., "Nanosecond pulsed electric field generators for the study of subcellular effects", Bioelectromagnetics, 27(3): p. 172-187 (2006).

Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.

Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.

Lee, R. C., D. J. Canaday, and S. M. Hammer. Transient and stable ionic permeabilization of isolated skeletal muscle cells after electrical shock. J. Burn Care Rehabil. 14:528- 540, 1993.

Martinsen, O. G. and Grimnes, S., Bioimpedance and bioelectricity basics. Academic press, 2011.

Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.

Min, M., U. Pliquett, T. Nacke, A. Barthel, P. Annus, and R. Land, "Broadband excitation for short-time impedance spectroscopy," Physiological measurement, vol. 29, No. 6, p. S185, 2008.

Neal II, R. E. et al. In Vitro and Numerical Support for Combinatorial Irreversible Electroporation and Electrochemotherapy Glioma Treatment. Annals of Biomedical Engineering, Oct. 29, 2013, 13 pages.

O'Brien, T. J et al., "Effects of internal electrode cooling on irreversible electroporation using a perfused organ model," Int. J. Hyperth., vol. 35, No. 1, pp. 44-55, 2018.

Pakhomova, O. N., Gregory, B., Semenov I., and Pakhomov, A. G., BBA—Biomembr., 2014, 1838, 2547-2554.

Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).

Ringel-Scaia, V. M et al.. High-frequency irreversible electroporation is an effective tumor ablation strategy that induces immunologic cell death and promotes systemic anti-tumor immunity. EBioMedicine, 2019,44, 112-125.

Rossmeisl, John H. et al. Safety and feasibility of the NanoKnife system for irreversible electroporation ablative treatment of canine spontaneous intracranial gliomas J. Neurosurgery 123.4 (2015): 1008-1025.

Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.

Sanchez, B., G. Vandersteen, R. Bragos, and J. Schoukens, "Optimal multisine excitation design for broadband electrical impedance spec-troscopy," Measurement Science and Technology, vol. 22, No. 11, p. 115601, 2011.

Shao, Qi et al. Engineering T cell response to cancer antigens by choice of focal therapeutic conditions, International Journal of Hyperthermia, 2019, DOI: 10.1080/02656736.2018.1539253.

Talele, S. and P. Gaynor, "Non-linear time domain model of electropermeabilization: Effect of extracellular conductivity and applied electric field parameters", Journal of Electrostatics,66(5-6): p. 328-334 (2008).

Talele, S. and P. Gaynor, "Non-linear time domain model of electropermeabilization: Response of a single cell to an arbitrary applied electric field", Journal of Electrostatics, 65(12): p. 775-784 (2007).

Teissie, J. and T.Y. Tsong, "Electric-Field Induced Transient Pores in Phospholipid-Bilayer Vesicles". Biochemistry, 20(6): p. 1548-1554(1981).

Tibbitt et al., "Hydrogels as Extracellular Matrix Mimics for 3D Cell Culture", Jul. 2009, Biotechnol Bioeng, 103 (4),655-663.

Van Den Bos, W. et al., "MRI and contrast-enhanced ultrasound imaging for evaluation of focal irreversible electroporation treatment: results from a phase i-ii study in patients undergoing ire followed by radical prostatectomy," European radiology, vol. 26, No. 7, pp. 2252-2260, 2016.

Voyer, D., A. Silve, L. M. Mir, R. Scorretti, and C. Poignard, "Dynamical modeling of tissue electroporation," Bioelectrochemistry, vol. 119, pp. 98-110, 2018.

Zhao, Y., S. Bhonsle, S. Dong, Y. Lv, H. Liu, A. Safaai-Jazi, R. V. Davalos, and C. Yao, "Characterization of conductivity changes during high-frequency irreversible electroporation for treatment planning," IEEE Transactions on Biomedical Engineering, vol. 65, No. 8, pp. 1810-1819, 2017.

Co-Pending U.S. Appl. No. 14/808,679, Response to Non-Final Office Action dated Jun. 12, 2020, filed Sep. 14, 2020, 9 pages.

Co-pending U.S. Appl. No. 16/152,743, Non-Final Office Action dated Sep. 25, 2020, 10 pages.

Co-pending U.S. Appl. No. 16/210,771, Response to Restriction Requirement, filed Jul. 8, 2020, 7 pages.

Co-pending U.S. Appl. No. 16/210,771, Restriction Requirement, dated Jun. 9, 2020, 7 pages.

(Davalos, Rafael V. et al.) Co-pending U.S. Appl. No. 15/536,333, filed Jun. 15, 2017, and published as U.S. Publication No. 2017/0360326 on Dec. 21, 2017, Specification, Claims, Figures.

(Davalos, Rafael V. et al.) Co-pending U.S. Appl. No. 16/352,759, filed Mar. 13, 2019, Specification, Claims, Figures.

(Davalos, Rafael V. et al.) Co-pending U.S. Appl. No. 16/865,031, filed May 1, 2020, Specification, Claims, Figures.

(Latouche, Eduardo et al.) Co-pending U.S. Appl. No. 16/210,771, filed Dec. 5, 2018, and which published as US Patent Publication No. 2019/0232048 on Aug. 1, 2019, Specification, Claims, Figures.

(Lorenzo, Melvin F. et al.) Co-pending U.S. Appl. No. 16/938,778, filed Jul. 24, 2020, Specification, Claims, Figures.

(Neal, Robert E. et al.) Co-pending U.S. Appl. No. 16/865,772, filed May 4, 2020, Specification, Claims, Figures.

(O'Brien, Timothy J. et al.) Co-Pending U.S. Appl. No. 16/915,760), filed Jun. 29, 2020, Specification, Claims, Figures.

(56) References Cited

OTHER PUBLICATIONS (Sano, Michael B. et al.) Co-Pending U.S. Appl. No. 16/747,219, filed Jan. 20, 2020, Specification, Claims, Figures.
(Wasson, Elisa M. et al.) Co-pending U.S. Appl. No. 17/000,049, filed Aug. 21, 2020, Specification, Claims, Figures.
Abiror, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).
Beebe, S.J., et al.,, "Nanosecond, high-intensity pulsed electric fields induce apoptosis in human cells", FASEB J, (9): p. 1493-5 (2003).
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.
Belehradek, J., et al., "Electropermeabilization of Cells in Tissues Assessed by the Qualitative and Quantitative Electroloading of Bleomycin", Biochimica Et Biophysica Acta-Biomembranes, 1190(1): p. 155-163 (1994).
Ben-David, E. et al., "Irreversible Electroporation: Treatment Effect is Susceptible to Local Environment and Tissue Properties," Radiology, vol. 269, No. 3, 2013, 738-747.
Benz, R., et al. "Reversible electrical breakdown of lipid bilayer membranes: a charge-pulse relaxation study". J Membr Biol, 48(2): p. 181-204 (1979).
Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S., M. F. Lorenzo, A. Safaai-Jazi, and R. V. Davalos, "Characterization of nonlinearity and dispersion in tissue impedance during high-frequency electroporation," IEEE Transactions on Biomedical Engineering, vol. 65, No. 10, pp. 2190-2201, 2018.
Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, p. 2674 2684, 2015.
Bondarenko, A. and G. Ragoisha, Eis spectrum analyser (the program is available online at http://www.abc.chemistry.bsu.by/vi/analyser/.
Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.
Bulvik, B. E. et al. "Irreversible Electroporation versus Radiofrequency Ablation☐: A Comparison of Local and Systemic Effects in a Small Animal Model," Radiology, vol. 280, No. 2, 2016, 413-424.
Castellvi, Q., B. Mercadal, and A. Ivorra, "Assessment of electroporation by electrical impedance methods," in Handbook of electroporation. Springer-Verlag, 2016, pp. 671-690.
Co-Pending U.S. Appl. No. 13/550,307 Interview Request and Summary, dated Dec. 13, 19, 2019, 4 pages.
Co-pending U.S. Appl. No. 13/550,307Non-final office action dated Aug. 22, 2019, 19 pages.
Co-pending U.S. Appl. No. 13/550,307 Notice of Allowance dated Apr. 28, 2020, 10 pages.
Co-pending U.S. Appl. No. 13/550,307 Response to Aug. 22, 2019 Non-final office action dated Dec. 23, 2019, 10 pages.
Co-pending U.S. Appl. No. 13/958,152, Non-Final Office Action dated Dec. 31, 2019, 15 pages.
Co-pending U.S. Appl. No. 14/686,380, Non-Final Office Action dated Feb. 13, 2020, 11 pages.
Co-pending U.S. Appl. No. 14/686,380, Non-Final Office Action, dated May 1, 2019, 18 pgs.
Co-pending U.S. Appl. No. 14/808,679, Interview Summary, dated Apr. 26, 2019, 3 pages.
Co-pending U.S. Appl. No. 14/808,679, Preliminary Amendment dated Jul. 24, 2015, 6 pages.
Co-pending U.S. Appl. No. 14/808,679, 3rd Renewed Petition, Dec. 9, 2019 and Petition Decision Dec. 18, 2019, 11 pages.
Co-pending U.S. Appl. No. 14/808,679, Non-Final Office Action dated Jun. 12, 2020,10 pages.
Co-pending U.S. Appl. No. 14/808,679, Petition Decision, Dec. 3, 2019, 5 pages.
Co-Pending U.S. Appl. No. 14/808,679, Petition Supplement, Sep. 25, 2019, 10 pages.
Co-Pending U.S. Appl. No. 14/808,679, Petition, May 8, 2019, 2 pages.
Co-Pending U.S. Appl. No. 14/808,679, Supplemental Response, May 8, 2019, 16 pages.
Co-Pending U.S. Appl. No. 15/310,114, Notice of Allowance, dated Aug. 19, 2019, 3 pages.
Co-Pending U.S. Appl. No. 15/310,114, Notice of Allowance, dated Jun. 21, 2019, 6 pages.
Co-Pending U.S. Appl. No. 15/310,114, Preliminary Amendment, dated Nov. 10, 2016, 9 pages.
Co-Pending U.S. Appl. No. 15/424,335, Notice of Allowance, dated Feb. 21, 2019, 7 pgs.
Co-Pending U.S. Appl. No. 15/536,333, Notice of allowance dated Apr. 13, 2020, 9 pages.
Co-Pending U.S. Appl. No. 15/536,333, Office Actions and Responses dated through Jan. 2, 2020, 69 pages.
Co-Pending U.S. Appl. No. 15/843,888, Non-Final Office Action dated Sep. 14, 2018, 17 pages.
Co-Pending U.S. Appl. No. 15/843,888, Notice of allowance, dated Sep. 3, 2019, 8 pgs.
Co-Pending U.S. Appl. No. 15/843,888, Preliminary Amendment dated Jan. 16, 2018, 20 pages.
Co-Pending U.S. Appl. No. 15/843,888, Response to Apr. 5, 2019 Final Office Action, filed Jul. 3, 2019, 7 pages.
Co-Pending U.S. Appl. No. 15/843,888, Response to Sep. 14, 2018 Non-Final Office Action, filed Dec. 14, 2018, 8 pages.
Co-Pending U.S. Appl. No. 16/177,745, Final office action dated Jan. 9, 2020, 8 pages.
Co-Pending U.S. Appl. No. 16/177,745, Notice of Allowance dated Jun. 30, 2020, 7 pages.
U.S. Appl. No. 14/017,210 (U.S. Pat. No. 10,245,098), file history through Jan. 2019, 294 pages.
U.S. Appl. No. 14/558,631 (U.S. Pat. No. 10,117,707), file history through Jul. 2018, 58 pages.
U.S. Appl. No. 14/627,046 (U.S. Pat. No. 10,245,105), file history through Feb. 2019, 77 pages.
U.S. Appl. No. 14/940,863 (U.S. Pat. No. 10,238,447), file history through Oct. 2019, 23 pages.
U.S. Appl. No. 15/011,752 (U.S. Pat. No. 10,470,822), file history through Jul. 2019, 54 pages.
U.S. Appl. No. 15/186,653 (U.S. Pat. No. 10,292,755), file history through Mar. 2019, 21 pages.
U.S. Appl. No. 15/310,114 (U.S. Pat. No. 10,471,254), file history through Aug. 2019, 44 pages.
U.S. Appl. No. 15/423,986 (U.S. Pat. No. 10,286,108), file history through Jan. 2019, 124 pages.
U.S. Appl. No. 15/424,335 (U.S. Pat. No. 10,272,178), file history through Feb. 2019, 57 pages.
U.S. Appl. No. 15/536,333 (U.S. Pat. No. 10,694,972), file history through Apr. 2020, 78 pages.
U.S. Appl. No. 15/843,888 (U.S. Pat. No. 10,537,379), file history through Sep. 2019, 33 pages.
U.S. Appl. No. 15/881,414 (U.S. Pat. No. 10,154,874), file history through Nov. 2018, 43 pages.
U.S. Appl. No. 16/177,745 (U.S. Pat. No. 10,828,085), file history through Jun. 2020, 57 pages.
U.S. Appl. No. 16/232,962 (U.S. Pat. No. 10,828,086), file history through Jun. 2020, 44 pages.
Pending U.S. Appl. No. 16/655,845, Preliminary Amendment filed Oct. 16, 2020, 6 pages.
Pending U.S. Appl. No. 16/747,219, Preliminary Amendment filed Jan. 20, 2020, 5 pages.
Pending U.S. Appl. No. 16/747,219, Preliminary Amendment filed Jan. 4, 2021, 5 pages.
Pending U.S. Appl. No. 16/865,031, Preliminary Amendment filed May 1, 2020, 7 pages.

(56) References Cited

OTHER PUBLICATIONS

Pending U.S. Appl. No. 16/865,772, Preliminary Amendment filed May 4, 2020, 6 pages.
Pending U.S. Appl. No. 16/915,760, Preliminary Amendment filed Jul. 6, 2020, 5 pages.
Pending Application No. AU 2009243079, First Examination Report, dateed Jan. 24, 2014, 4 pages.
Pending Application No. AU 2009243079, Voluntary Amendment filed Dec. 6, 2010, 35 pages.
Pending Application No. AU 2015259303, First Examination Report dated Oct. 26, 2020, 6 pages.
Pending Application No. CA 2,722,296 Examination Report dated Apr. 2, 2015, 6 pages.
Pending Application No. CN 201580025135.6 English translation of Apr. 29, 2020 Office action, 7 pages.
Pending Application No. CN 201580025135.6 English translation of Sep. 25, 2019 Office action.
Pending Application No. CN 201580025135.6 Preliminary Amendment filed with application Nov. 14, 2016.
Pending Application No. CN 201580025135.6 Response to Sep. 25, 2019 Office action, filed Feb. 10, 2020, English language version and original document.
Pending Application No. CN 201580025135.6, First Office Action, dated Sep. 25, 2019 (Chinese and English Versions, each 6 pages).
Pending Application No. CN 201580025135.6, Response to First Office Action, dated Feb. 7, 2020, (Chinese Vrsion, 13 pages, and English Version, 10 pages).
Pending Application No. CN 201580025135.6, Second Office Action, dated Apr. 29, 2020 (Chinese Version, 4 pages, and English Version, 7 pages).
Pending Application No. EP 09739678.2, Communication pursuant to Rule 94.3, dated Apr. 16, 2014, 3 pages.
Pending Application No. EP 09739678.2, Office Action dated Apr. 16, 2014, 3 pages.
Pending Application No. EP 09739678.2, Response to Extended European Search Report and Communication pursuant to Rules 70(2) and 70a(2) EPC, dated Dec. 10, 2012.
Pending Application No. EP 10824248.8, Extended Search Report (dated Jan. 20, 2014), 6 pages.
Pending Application No. EP 10824248.8, Invitation Pursuant to rule 62a(1) EPC (Sep. 25, 2013), 2 pages.
Pending Application No. EP 10824248.8, Communication Pursuant to Rule 7 0(2) dated Feb. 6, 2014, 1 page.
Pending Application No. EP 10824248.8, Response to Invitation Pursuant to rule 62a(1) EPC (Sep. 25, 2013), Response filed Nov. 18, 2013.
Pending Application No. EP 11842994.3, Communication Pursuant to Rules 70(2) and 70a(2) EPC dated Apr. 28, 2014,1 page.
Pending Application No. EP 11842994.3, Extended European Search Report dated Apr. 9, 2014, 34 pages.
Pending Application No. EP 15793361.5, Claim amendment filed Jul. 18, 2018, 13 pages.
Pending Application No. EP 15793361.5, European Search Report dated Dec. 4, 2017, 9 pages.
Pending Application No. JP 2013-541050, Voluntary Amendment filed Oct. 29, 2013, 4 pages (with English Version of the Claims, 2 pages).
Pending Application No. JP 2016-567747 Amendment filed Jul. 18, 2019, 7 pgs.
Pending Application No. JP 2016-567747 English translation of amended claims filed Jul. 18, 2019, 6 pgs.
Pending Application No. JP 2016-567747, First Office Action (Translation) dated Feb. 21, 2019, 5 pages.
Pending Application No. JP 2016-567747, First Office Action dated Feb. 21, 2019, 4 pages.
Pending Application No. JP 2016-567747, Decision to Grant with English Version of allowed claims, 9 pages.
Pending Application No. JP 2019-133057, amended claims (English language version) filed Aug. 14, 2019, 5 pages.
Pending Application No. JP 2019-133057, Office Action dated Sep. 14, 2020, 5 pages and English translation, 6 pages).
Qiao et al. Electrical properties of breast cancer cells from impedance measurement of cell suspensions, 2010, Journal of Physics, 224, 1-4 (2010).
SAI Infusion Technologies, "Rabbit Ear Vein Catheters", https://www.sai-infusion.com/products/rabbit-ear-catheters, Aug. 10, 2017 webpage printout, 5 pages.
Thomson et al., "Investigation of the safety of irreversible electroporation in humans," J Vasc Interv Radiol, 22, pp. 611-621, 2011.
U.S. Appl. No. 12/491,151 (U.S. Pat. No. 8,992,517), file history through Feb. 2015, 113 pages.
U.S. Appl. No. 12/609,779 (U.S. Pat. No. 8,465,484), file history through May 2013, 100 pages.
U.S. Appl. No. 12/757,901 (U.S. Pat. No. 8,926,606), file history through Jan. 2015, 165 pages.
U.S. Appl. No. 12/906,923 (U.S. Pat. No. 9,198,733), file history through Nov. 2015, 55 pages.
U.S. Appl. No. 13/332,133 (U.S. Pat. No. 10,448,989), file history through Sep. 2019, 226 pages.
U.S. Appl. No. 13/550,307 (U.S. Pat. No. 10,702,326), file history through May 2020, 224 pages.
U.S. Appl. No. 13/919,640 (U.S. Pat. No. 8,814,860), file history through Jul. 2014, 41 pages.
U.S. Appl. No. 13/958,152, file history through Dec. 2019, 391 pages.
U.S. Appl. No. 13/989,175 (U.S. Pat. No. 9,867,652), file history through Dec. 2017, 200 pages.
U.S. Appl. No. 14/012,832 (U.S. Pat. No. 9,283,051), file history through Nov. 2015, 17 pages.
(Davalos, Rafael V. et al.) Co-pending U.S. Appl. No. 17/069,359, filed Oct. 13, 2020, Specification, Claims, Drawings.
(Davalos, Rafael V. et al.) Co-pending U.S. Appl. No. 17/172,731, filed Feb. 10, 2021, Specification, Claims, Figures.
(Davalos, Rafael V. et al.) Co-Pending Application No. AU 2009243079, filed Apr. 29, 2009 (see PCT/US2009/042100 for documents as filed), Specification, Claims, Figures.
(Davalos, Rafael V. et al.) Co-Pending International Application No. PCT/US15/65792, filed Dec. 15, 2015, Specification, Claims, Drawings.
(Davalos, Rafael V.) Co-Pending Application No. CA 2,722,296, filed Apr. 29, 2009, Amended Claims (7 pages), Specification, Figures (See PCT/US2009/042100 for Specification and figures as filed).
(Davalos, Rafael V.) Co-Pending Application No. EP 09739678.2 filed Apr. 29, 2009, Amended Claims (3 pages), Specification and Figures (See PCT/US2009/042100).
(Neal, Robert et al.) Co-Pending Application No. EP 10824248.8, filed May 9, 2012, Amended Claims 3 pages), Specification and Figures (See PCT/US10/53077).
(O'Brien, Timothy J. et al.) Co-Pending U.S. Appl. No. 17/152,379, filed Jan. 19, 2021, Specification, Claims, Figures.
(Sano, Michael B. et al.) Co-Pending Application No. AU 2015259303, filed Oct. 24, 2016, Specification, Figures, Claims.
(Sano, Michael B. et al.) Co-Pending Application No. CN 201580025135.6, filed Nov. 14, 2016, Specification, Claims, Figures (Chinese language and english language versions).
(Sano, Michael B. et al.) Co-Pending Application No. CN 202011281572.3, filed Nov. 16, 2020, Specification, Claims, Figures (Chinese version, 129 pages (see also WO 2015/175570), English Version of claims, 2 pages).
(Sano, Michael B. et al.) Co-Pending Application No. EP 11842994.3, filed Jun. 24, 2013, Amended Claims (18 pages), Specification and Figures (See PCT/US11/62067).
(Sano, Michael B. et al.) Co-Pending Application No. EP 15793361.5, filed Dec. 12, 2016, Specification, Claims, Figures.
(Sano, Michael B. et al.) Co-pending application No. HK 17112121.8, filed Nov. 20, 2017 and published as Publication No. HK1238288 on Apr. 27, 2018, Specification, Claims, Figures (See PCT/US15/30429 for English Version of documents as filed).
(Sano, Michael B. et al.) Co-Pending Application No. JP 2013-541050, filed May 22, 2013, Claims, Specification, and Figures (See PCT/US11/62067 for English Version).

(56) References Cited

OTHER PUBLICATIONS (Sano, Michael B. et al.) Co-Pending Application No. JP 2016-567747, filed Nov. 10, 2016, Specification, Claims, Figures (see PCT/US15/30429 for English Version of documents as filed).
(Sano, Michael B. et al.) Co-pending Application No. JP 2019-133057 filed Jul. 18, 2019, 155 pgs, Specification, Claims, Figures (See PCT/US15/30429 for English Version of documents as filed).
PCT Application No. PCT/US15/65792, International Search Report (dated Feb. 9, 2016), Written Opinion (dated Feb. 9, 2016), and International Preliminary Report on Patentability (dated Jun. 20, 2017), 15 pages.
Pending U.S. Appl. No. 14/686,380, Final Office Action dated May 9, 2018, 14 pages.
Pending U.S. Appl. No. 14/686,380, Final Office Action dated Oct. 6, 2020, 14 pages.
Pending U.S. Appl. No. 14/686,380, Non-Final Office Action dated May 1, 2019, 18 pages.
Pending U.S. Appl. No. 14/686,380, Non-Final Office Action dated Nov. 22, 2017, 11 pages.
Pending U.S. Appl. No. 14/686,380, Response dated Feb. 13, 2020 Non-Final Office Action, filed Jul. 1, 2020, 8 pages.
Pending U.S. Appl. No. 14/686,380, Response dated Jul. 19, 2017 Restriction Requirement, dated Sep. 15, 2017, 2 pages.
Pending U.S. Appl. No. 14/686,380, Response to May 9, 2018 Final Office Action with RCE, dated Aug. 30, 2018, 14 pages.
Pending U.S. Appl. No. 14/686,380, Response to Non-Final Office Action Filed Aug. 1, 2019, 11 pages.
Pending U.S. Appl. No. 14/686,380, Response dated Nov. 22, 2017 Non-Final Office Action dated Mar. 28, 2018, 11 pages.
Pending U.S. Appl. No. 14/686,380, Response dated Oct. 6, 2020 Final Office Action with RCE, dated Jan. 6, 2020, 11 pages.
Pending U.S. Appl. No. 14/686,380, Response dated Sep. 3, 2019 Final Office Action, filed Jan. 3, 2020, 10pages.
Pending U.S. Appl. No. 14/686,380, Restriction Requirement dated Jul. 19, 2017, 7 pages.
Pending U.S. Appl. No. 14/808,679, Final Office Action dated Dec. 28, 2020, 11 pages.
Pending U.S. Appl. No. 14/808,679, Final Office Action dated Jan. 11, 2019, 12 pages.
Pending U.S. Appl. No. 14/808,679, Non-Final Office Action dated Sep. 10, 2018, 12 pages.
Pending U.S. Appl. No. 14/808,679, Petition Decision, dated Oct. 1, 2019, 5 pages.
Pending U.S. Appl. No. 14/808,679, Petition Decision, dated Oct. 23, 2019, 6 pages.
Pending U.S. Appl. No. 14/808,679, Petition for Priority and Supplemental Response, filed May 8, 2019, 25 pages.
Pending U.S. Appl. No. 14/808,679, Preliminary Amendment, filed Jul. 27, 2015, 9 pages.
Pending U.S. Appl. No. 14/808,679, RCE filed Apr. 11, 2019, 8 pages.
Pending U.S. Appl. No. 14/808,679, Renewed Petition, filed Oct. 9, 2019, 1 pages.
Pending U.S. Appl. No. 14/808,679, Response dated Mar. 19, 2018 Restriction Requirement dated May 21, 2018, 2 pages.
Pending U.S. Appl. No. 16/152,743 Preliminary Amendment filed Oct. 5, 2018, 7 pages.
Pending U.S. Appl. No. 16/152,743, Petition for Delayed Claim for Priority dated Dec. 28, 2020, 2 pages.
Pending U.S. Appl. No. 16/152,743, Response to Sep. 25, 2020 Non-Final Office Action dated Dec. 28, 2020, 9 pages.
Pending U.S. Appl. No. 16/152,743, Second Preliminary Amendment filed May 2, 2019, 6 pages.
Pending U.S. Appl. No. 16/210,771, Preliminary Amendment filed Dec. 5, 2018, 8 pages.
Pending U.S. Appl. No. 16/210,771, Response to Sep. 3, 2020 Non-Final Office Action filed Jan. 4, 2021, 11 pages.
Pending U.S. Appl. No. 16/210,771, Second Preliminary Amendment filed Oct. 14, 2019, 7 pages.
Pending U.S. Appl. No. 16/275,429 Notice of Allowance dated Nov. 10, 2020, 9 pages.
Pending U.S. Appl. No. 16/280,511, Non-final Office Action dated Dec. 4, 2020, 10 pgs.
Pending U.S. Appl. No. 16/280,511, Preliminary Amendment filed Nov. 2, 2020, 6 pages.
(Davalos, Rafael et al.) Co-Pending Application No. PCT/US21/51551, filed Sep. 22, 2021, Specification, Claims, Figures.
Pending U.S. Appl. No. 14/686,380, Amendment after Notice of Appeal, dated Oct. 12, 2021, 6 pages.
Pending U.S. Appl. No. 16/152,743, Response to Jul. 15, 2021 Final Office Action, filed Oct. 13, 2021, 6 pages.
Pending U.S. Appl. No. 16/210,771, Non-Final Office Action dated Oct. 7, 2021, 10 pages.
Pending U.S. Appl. No. 16/352,759, Response to Non-Final Office Action dated Sep. 27, 2021, 6 pages.
Pending U.S. Appl. No. 16/520,901, Non-Final Office Action, dated Oct. 13, 2021, 9 pages.
Pending Application No. AU 2015259303, Response to First Examination Report dated Sep. 20, 2021, 126 pages.
Pending Application No. JP 2019-133057, Office Action dated Sep. 1, 2021, 3 pages (and English translation, 4 pages).
(Davalos, Rafael V. et al.) Co-pending U.S. Appl. No. 17/277,662, filed Mar. 18, 2021, Specification, Claims, Figures.
(Davalos, Rafael V. et al.) Co-pending Application No. 19861489.3 filed Apr. 16, 2021, Specification, figures (See PCT/US19/51731), and claims (3 pages).
(Neal, Robert et al.) Co-pending U.S. Appl. No. 17/338,960, filed Jun. 4, 2021, Specification, Claims, Figures.
Alinezhadbalalami, N. et al., "Generation of Tumor-activated T cells Using Electroporation", Bioelectrochemistry 142 (2021) 107886, Jul. 13, 2021, 11 pages.
PCT Application No. PCT/US19/51731, International Preliminary Reporton Patentability dated Mar. 23, 2021, 13 pages.
Pending U.S. Appl. No. 14/686,380, Applicant Initiated Interview Summary dated Feb. 9, 2021, 3 pages.
Pending U.S. Appl. No. 14/686,380, Applicant Initiated Interview Summary dated Mar. 8, 2021, 2 pages.
Pending U.S. Appl. No. 14/686,380, Final Office Action dated Sep. 3, 2019, 28 pages.
Pending U.S. Appl. No. 14/686,380, Non-Final Office Action dated May 7, 2021, 17 pages.
Pending U.S. Appl. No. 14/808,679, Appeal Brief, filed Jun. 3, 2021, 25 pages.
Pending U.S. Appl. No. 14/808,679, Examiner's Answer to Appeal Brief, dated Sep. 15, 2021, 6 pages.
Pending U.S. Appl. No. 14/808,679, Panel Decision from Pre-Appeal Brief Review, dated Apr. 26, 2021, 2 pages.
Pending U.S. Appl. No. 14/808,679, Pre-Appeal Brief Reasons for Request for Review, dated Mar. 29, 2021, 5 pages.
Pending U.S. Appl. No. 14/808,679, Response to Sep. 10, 2018 Non-Final Office Action dated Dec. 10, 2018, 9 pages.
Pending U.S. Appl. No. 14/808,679, Second Renewed Petition, filed Oct. 31, 2019, 3 pages.
Pending U.S. Appl. No. 16/152,743, Final Office Action dated Jul. 15, 2021, 8 pages.
Pending U.S. Appl. No. 16/210,771, Applicant-Initiated Interview Summary dated Aug. 13, 2021, 4 pages.
Pending U.S. Appl. No. 16/210,771, Final Office Action dated May 14, 2021, 13 pages.
Pending U.S. Appl. No. 16/210,771, Response to May 14, 2021 Final Office Action, filed Aug. 16, 2021, 6 pages.
Pending U.S. Appl. No. 16/280,511, Notice of Allowance dated Aug. 2, 2021, 7 pgs.
Pending U.S. Appl. No. 16/280,511, Response to Dec. 4, 2020 Non-final Office Action dated Jun. 4, 2021, 8 pgs.
Pending U.S. Appl. No. 16/352,759, Non-Final Office Action dated Jun. 30, 2021, 7 pages.
Pending U.S. Appl. No. 16/375,878, Non-Final Office Action dated Jun. 24, 2021, 8 pages.
Pending U.S. Appl. No. 16/535,451 Non-Final Office Action, dated Jun. 24, 2021, 12 pages.

(56) References Cited

OTHER PUBLICATIONS

Pending U.S. Appl. No. 16/865,031, Second Preliminary Amendment, filed Sep. 17, 2021, 10 pages.
Pending U.S. Appl. No. 16/865,772, Second Preliminary Amendment filed Jun. 30, 2020, 4 pages.
Pending U.S. Appl. No. 16/865,772, Third Preliminary Amendment, filed Sep. 17, 2021, 6 pages.
Pending U.S. Appl. No. 17/069,359, Preliminary Amendment, filed Sep. 17, 2021, 6 pages.
Pending U.S. Appl. No. 17/172,731, Preliminary Amendment, filed Sep. 17, 2021, 7 pages.
Pending U.S. Appl. No. 17/277,662 Preliminary Amendment filed Mar. 18, 2021, 8 pages.
Pending U.S. Appl. No. 17/338,960, Response to Notice to File Missing Parts and Amendment, filed Aug. 16, 2021, 7 pages.
Pending Application No. CN 202011281572.3, Amendment filed Sep. 8, 2021 (16 pages) with English Version of the Amended Claims (7 pages).
Pending Application No. EP 15793361.5, Communication Pursuant to Article 94(3) EPC, dated May 3, 2021, 4 pages.
Pending Application No. JP 2019-133057, Response to Sep. 14, 2020 Office Action filed Mar. 18, 2021 (6 pages) with English Version of claims and response (5 pages).
U.S. Appl. No. 16/275,429 (U.S. Pat. No. 10,959,772), file history through Feb. 2021, 18 pages.

* cited by examiner

With Conductivity Change: (Electric Field, V/cm)

With Conductivity Change:
Conductivity Map: (S/m)

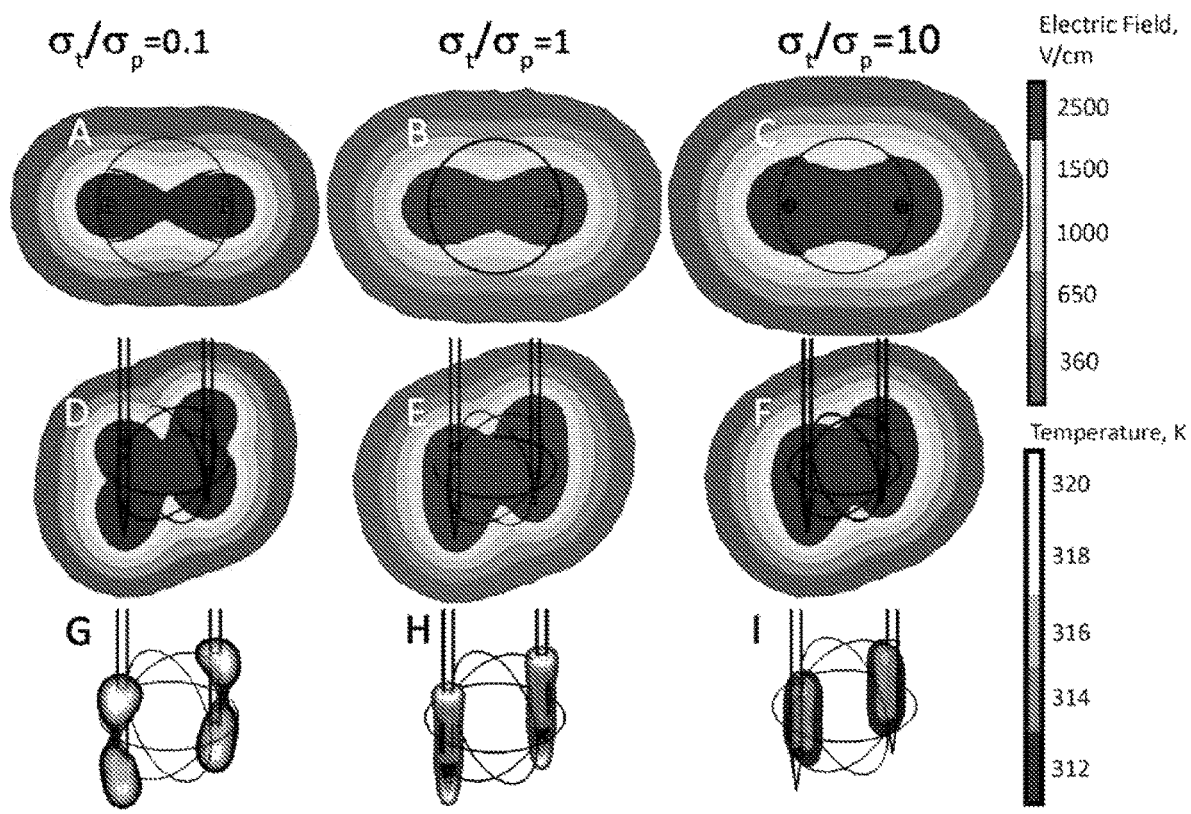
FIG. 2A-I
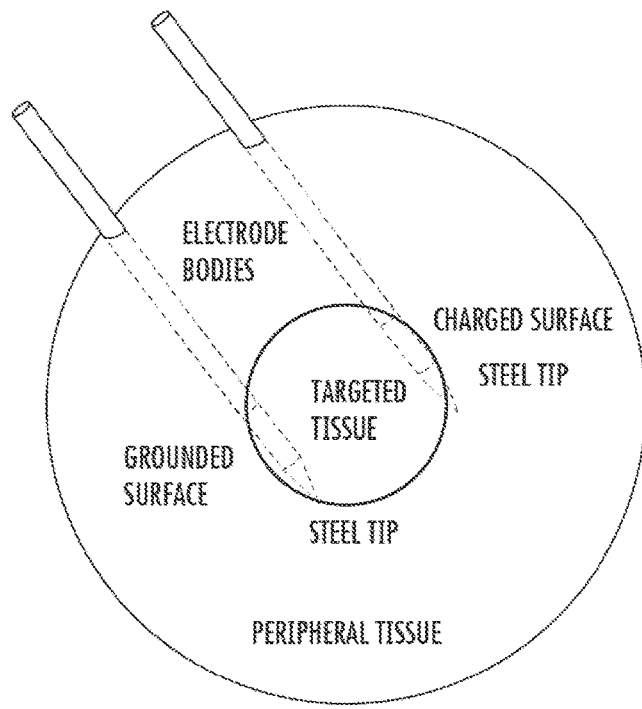
FIG. 2J

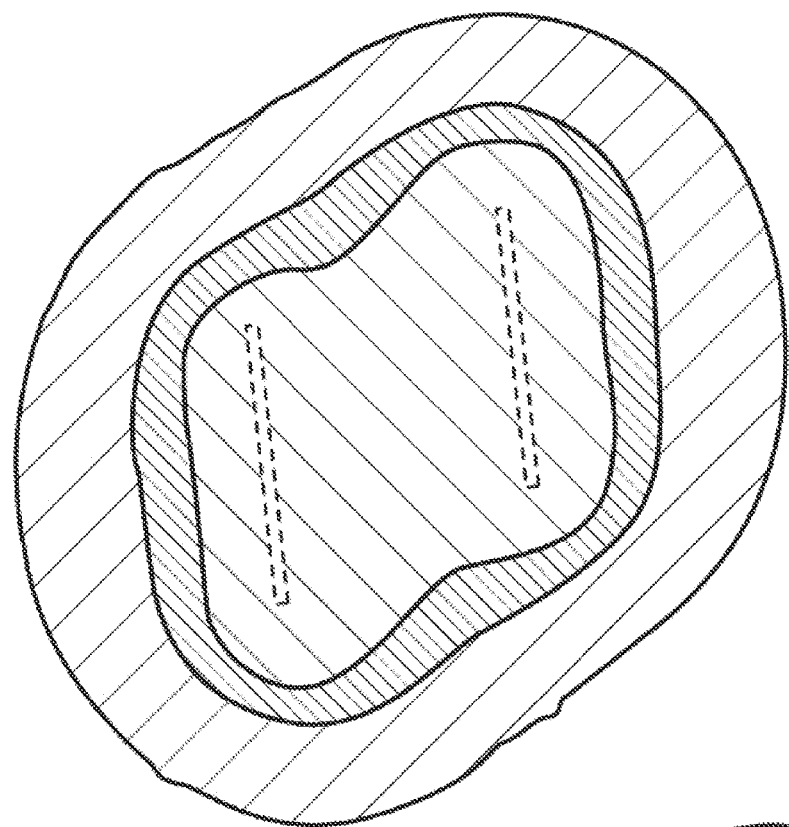
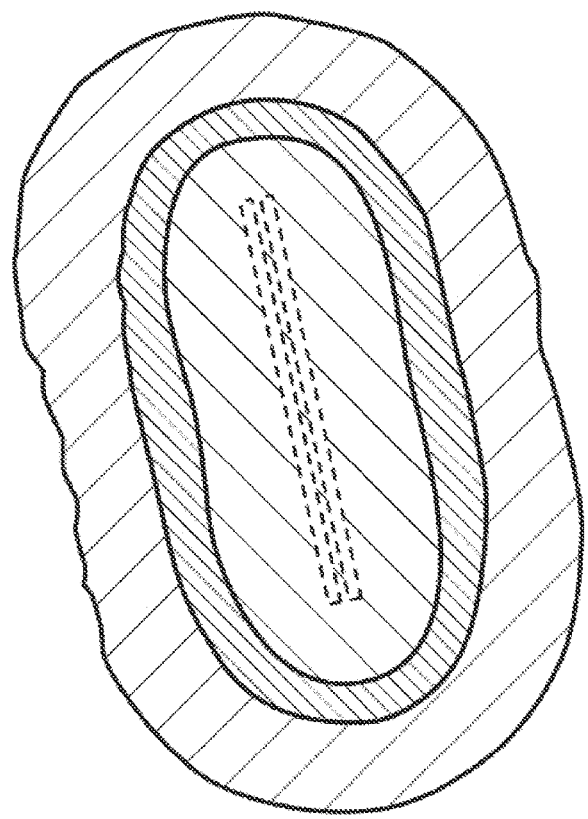
FIG. 11A

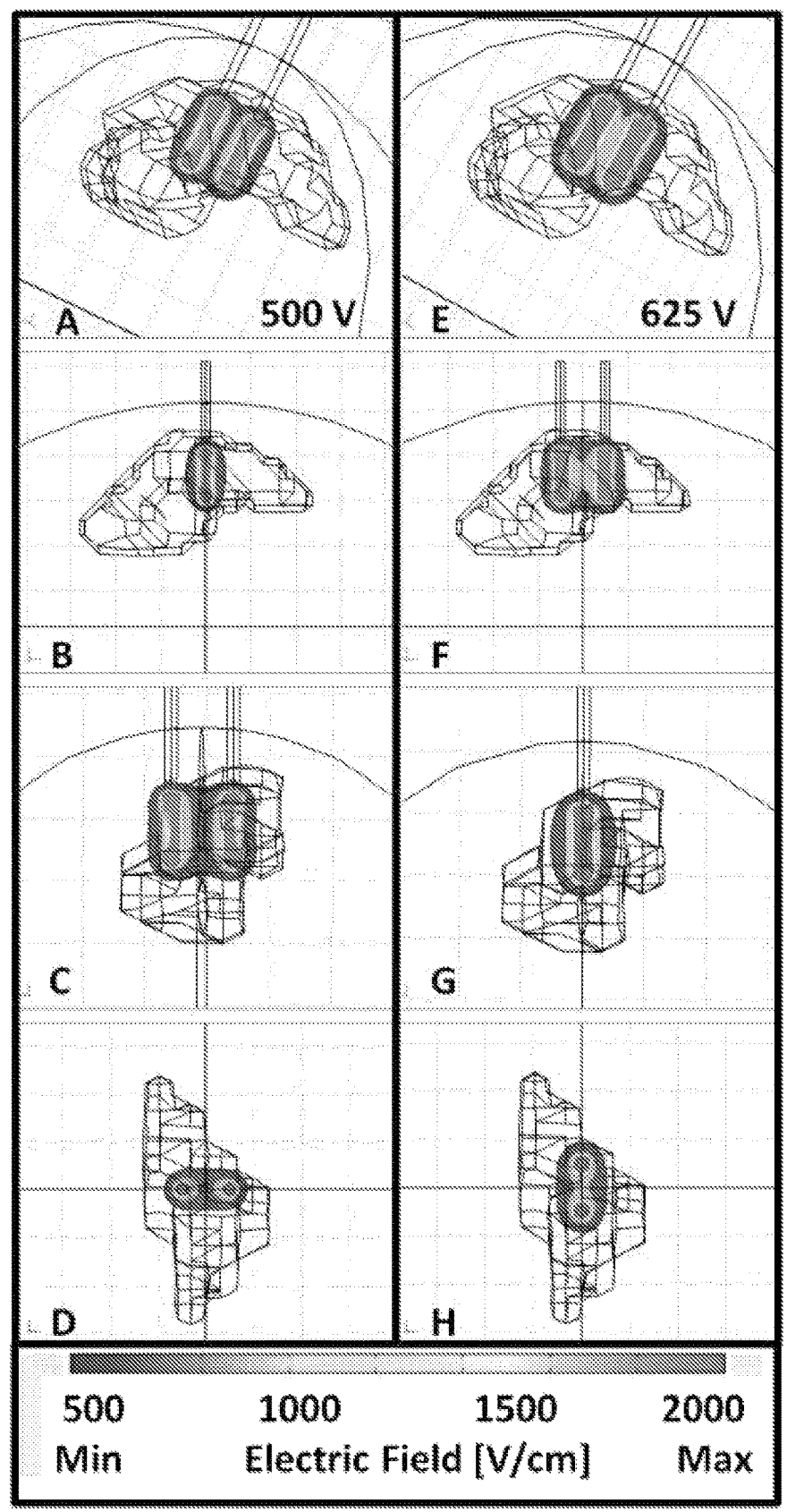
FIGS. 21A-H

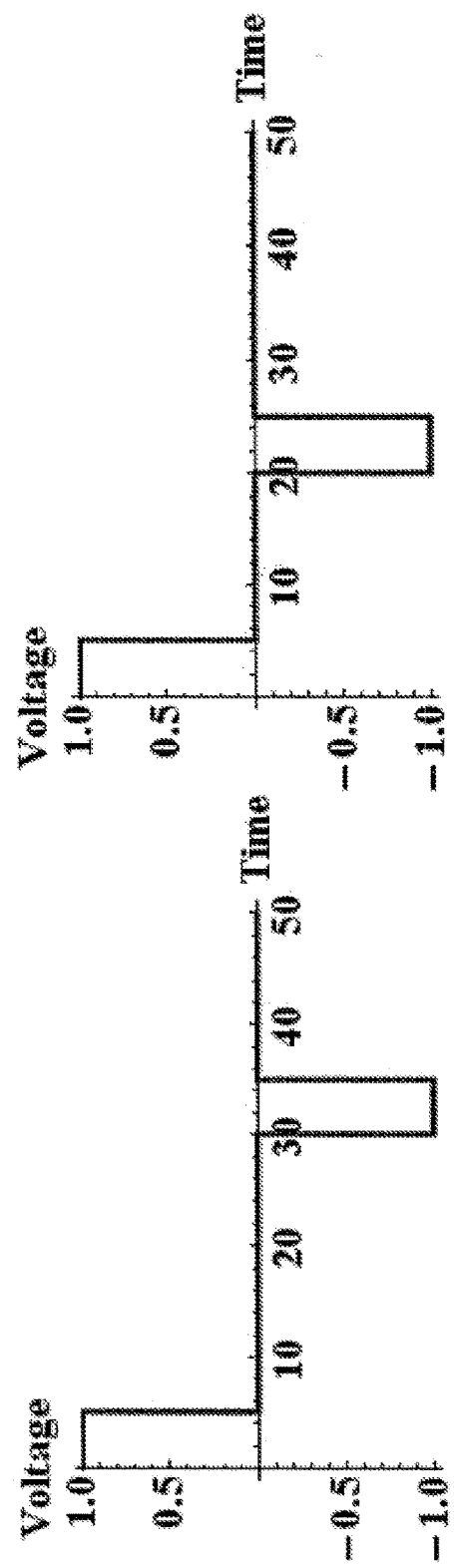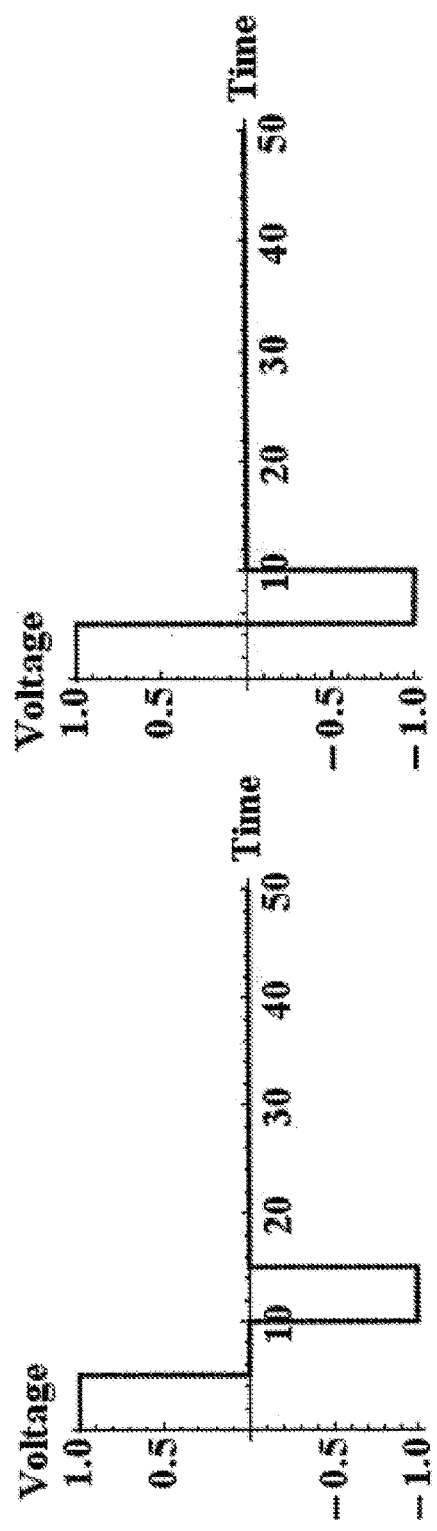
FIG. 24A  FIG. 24B  FIG. 24C  FIG. 24D

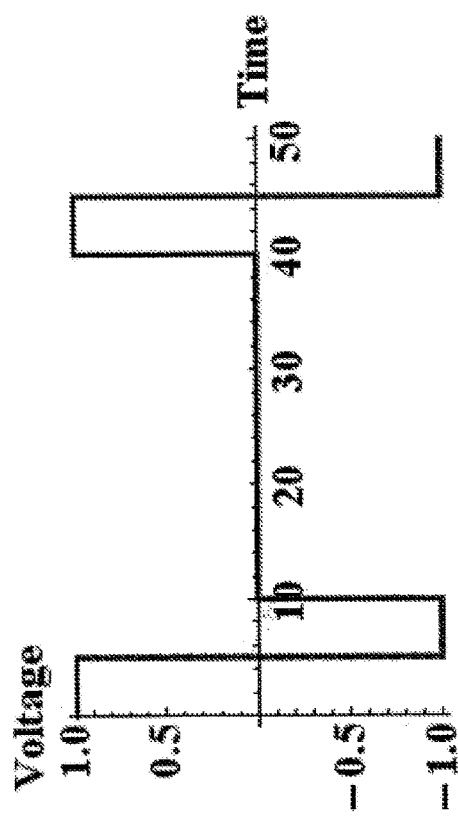
FIG. 24E
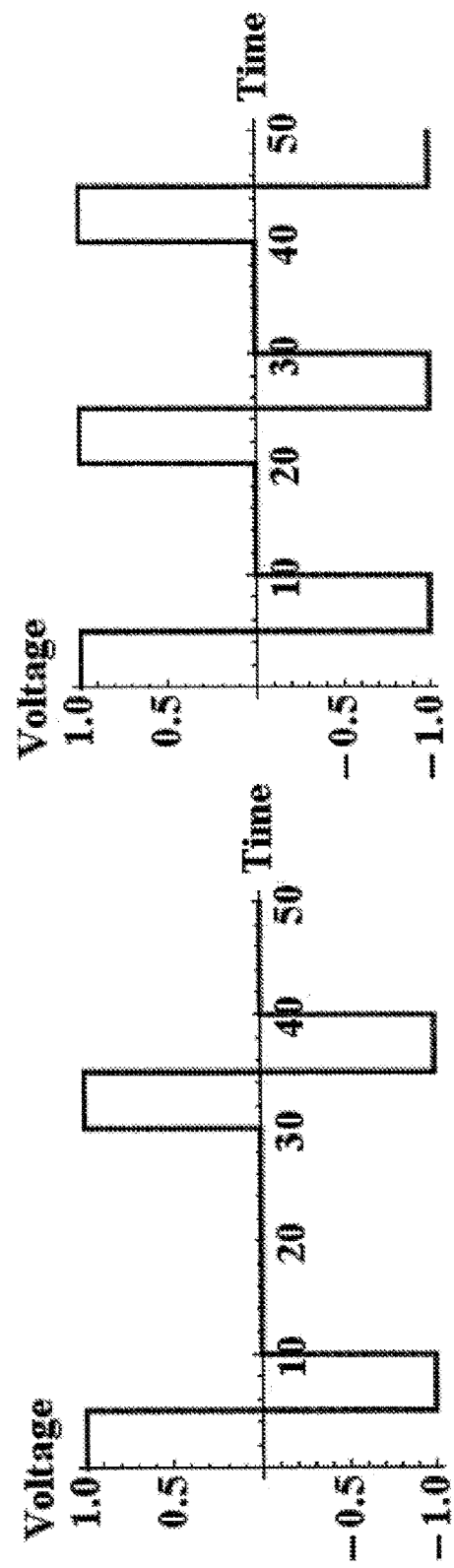
FIG. 24F
FIG. 24G

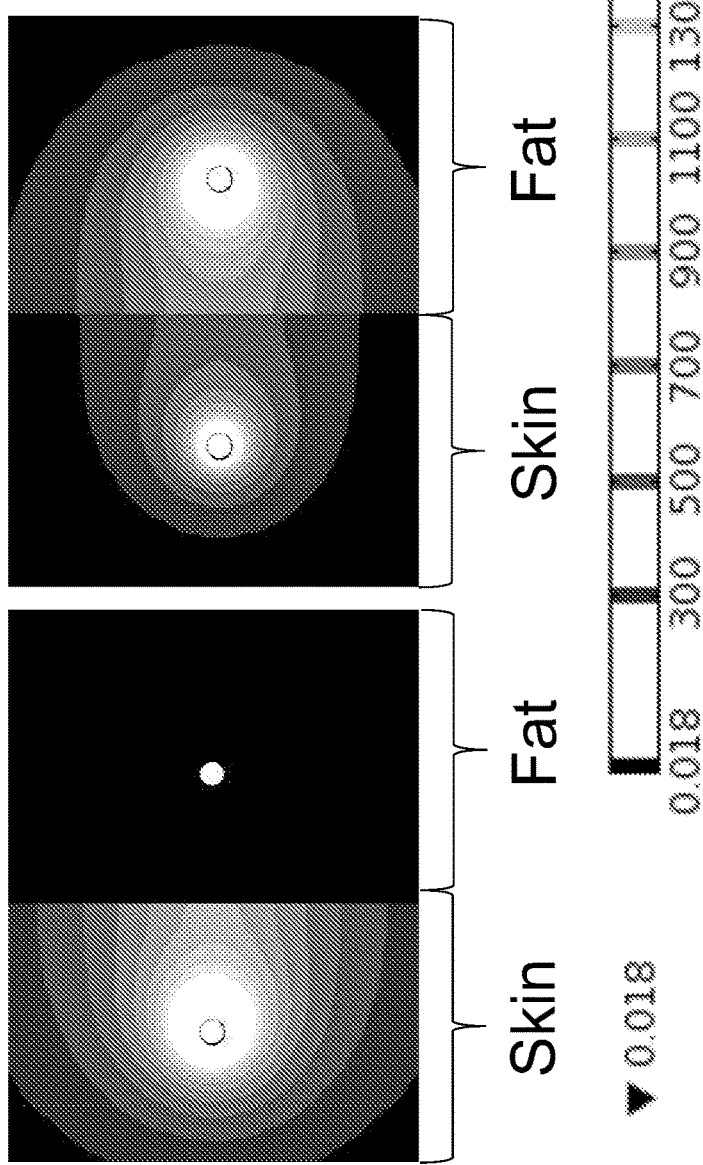

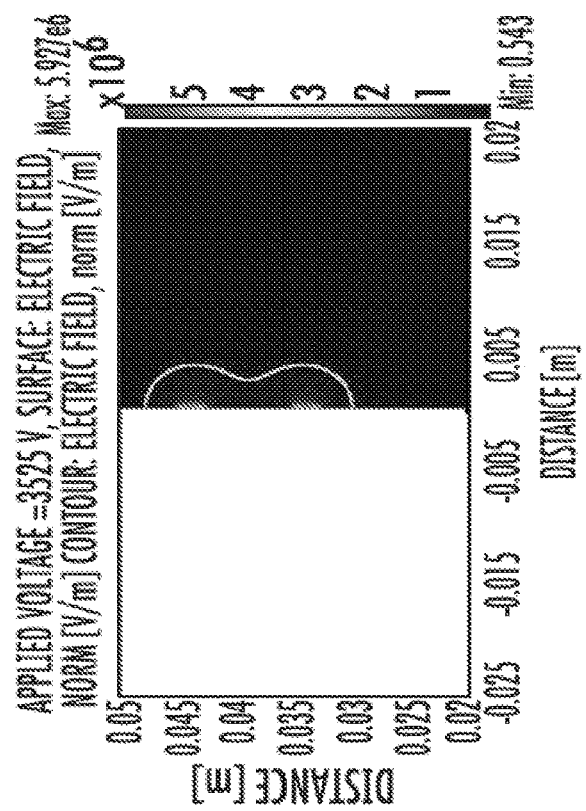
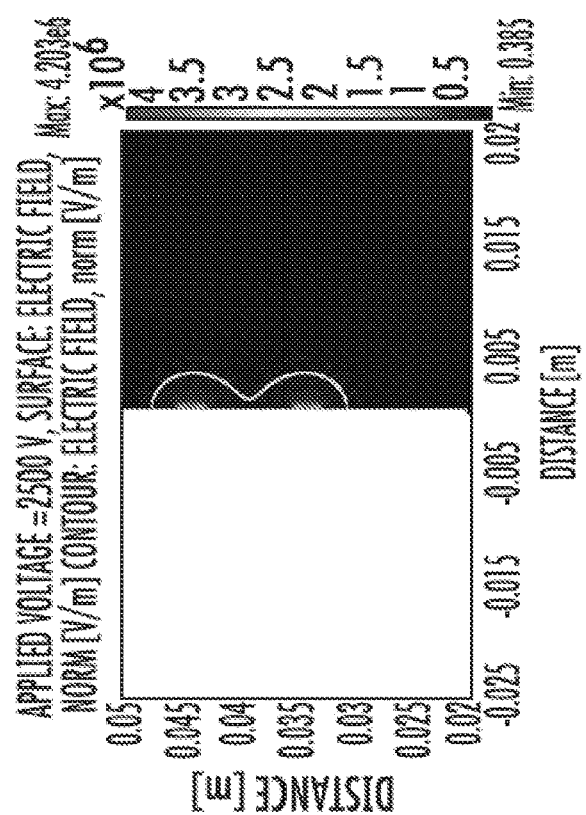
FIG. 35E

DEVICES AND METHODS FOR HIGH FREQUENCY ELECTROPORATION

CROSS-REFERENCE TO RELATED APPLICATIONS

This application is a Continuation Application of U.S. patent application Ser. No. 14/808,679. The '679 application is a Divisional Application of U.S. patent application Ser. No. 12/906,923, filed Oct. 18, 2010. The '923 application claims priority to and the benefit of the filing date of U.S. Provisional Application No. 61/252,445, filed Oct. 16, 2009 and is a Continuation-in-Part (CIP) of U.S. patent application Ser. No. 12/757,901, filed Apr. 9, 2010. The '901 application claims priority to U.S. Provisional Application Nos. 61/167,997, filed Apr. 9, 2009, and 61/285,618, filed Dec. 11, 2009. The '923 application is a CIP of U.S. patent application Ser. No. 12/609,779, filed Oct. 30, 2009 and the '923 application is a CIP of U.S. application Ser. No. 12/491,151, filed Jun. 24, 2009. The '151 application claims priority to U.S. Provisional Application Nos. 61/075,216, filed Jun. 24, 2008, 61/171,564, filed Apr. 22, 2009, and 61/167,997, filed Apr. 9, 2009, and is a CIP of U.S. patent application Ser. No. 12/432,295, filed Apr. 29, 2009. The '295 application claims priority to U.S. Provisional Application No. 61/125,840, filed Apr. 29, 2008. The disclosures of these applications are hereby incorporated by reference herein in their entireties. Additionally, the present application is a CIP of U.S. patent application Ser. No. 13/332,133, filed Dec. 20, 2011, which '133 Application published on May 3, 2012 as U.S. Patent Application Publication No. 2012/0109122, and which '133 Application claims priority to U.S. Provisional Application No. 61/424,872, filed Dec. 20, 2010, and which '133 Application is a CIP of the '901 Application, which '901 Application, as indicated above, claims priority to U.S. Provisional Application No. 61/167,997, filed Apr. 9, 2009, and No. 61/285,618, filed Dec. 11, 2009.

BACKGROUND OF THE INVENTION

Field of the Invention

The present invention provides systems, methods, and devices for electroporation-based therapies (EBTs). Embodiments provide patient-specific treatment protocols derived by the numerical modeling of 3D reconstructions of target tissue from images taken of the tissue, and optionally accounting for one or more of physical constraints and/or dynamic tissue properties. The present invention further relates to systems, methods, and devices for delivering bipolar electric pulses for irreversible electroporation without damage to tissue typically associated with an EBT-induced excessive charge delivered to the tissue and mitigate electrochemical effects that may distort the treatment region.

Description of Related Art

Irreversible electroporation (IRE) and other electroporation-based therapies (EBTs), such as electrogenetransfer or electrochemotherapy, may often be administered in a minimally invasive fashion. There are, however, several considerations that may lead to an increase in the difficulty of administering such treatments. This includes typical applications where deep targeted regions are treated by placing needle or other electrodes deep into the tissue, where one can no longer directly visualize the affected area. There is some evidence that changes in the tissue's permeability, and therefore also its electrical conductivity, allow one to visualize and monitor affected regions in real-time. These changes are most pronounced in homogeneous and image-dense tissues, such as hyperechoic ultrasound tissues, where increased permeability decreases the electroporated echogenicity. However, many tumors and other tissues are far too heterogeneous or exhibit properties that do not allow for simple visualization of the electroporated areas. In addition, these changes for real-time imaging typically only designate electroporated regions, not necessarily those killed for IRE therapies.

In applying EBTs, ensuring adequate coverage of the targeted region (e.g., any mass or lesion or undesirable tissue to be affected, including margins beyond the lesion itself), while sparing healthy tissues is vital to therapeutic success. Due to the limitations inherent in treating deep tissues without exposing them, it is critical for practitioners to develop and implement treatment protocols capable of achieving their clinical objectives.

Furthermore, typical electrodes and pulsing parameters (number of pulses, pulse polarity, pulse length, repetition rate, pulse shape, applied voltage, electrode geometry and orientation, etc.) will have a large impact on the affected areas. Typical therapeutic geometries dictated by current electrode setups will be ellipsoidal in general shape. However, many tumors do not distinctly fit the shapes created by a single setup of an electrode. Therefore, successful implementation of EBTs typically requires a complex array of electrodes and pulse parameters arranged in a specific manner to ensure complete treatment of the targeted area while minimizing effects to healthy tissue and sparing vital structures. Such predictions of superimposing treatment regions for complex protocols can be cumbersome. Therefore, treatment planning techniques that aid or allow a practitioner to develop general treatment protocols for most clinical tumors are typically used to effectively capitalize on the great therapeutic potential for IRE and other EBTs.

Current treatment planning techniques from systems such as the NanoKnife® utilize interpolations and analytical techniques to aid practitioner treatment region predictions. The interpolation techniques provide the physician with diagrams of 3D numerical model solution predicted treatment areas from very specific settings, including an exact number of pulses, pulse length, voltage, and electrode setup (e.g., separation distance, exposure length, and diameter) with dimensions provided for the treatment areas in 2 planes and the general shape. The predicted treatment dimensions are taken from the experimental results of applying that specific set of conditions in experimental subjects, typically in healthy, homogeneous environments. It is from this diagram of expected region, that the physician would set up their electrodes the same way and use the same pulses and arrange multiple applications to the point where they anticipate they will have treated the entire volume.

There is room, however, for improvement in such systems. If the targeted volume is smaller than the dimensions in the diagram, the practitioner has no information about how much to change the physical setup (exposure length, separation distance, etc.), or pulse parameters (voltage, number of pulses, etc.) in order to prevent damaging the surrounding tissue. In another example, if the shape does not fit that of the diagram, the practitioner will not be able to adjust the protocol to minimize damage beyond the targeted margin while still treating the targeted area.

In another solution to facilitating practitioner treatment planning, software is provided that uses a lookup table of treatment dimensions or uses a calibrated analytical solution to mimic the shape of numerical simulations. The lookup table may be taken from a large compilation of simulations run at varying physical and pulse parameters, where dimensions of interest for predicted treatment regions are taken based on a calibrated electric field threshold found to represent the affected margin of interest observed in experiments on healthy tissue (IRE, reversible electroporation, no electroporation, thermal damage).

Although the lookup table would allow a practitioner to manipulate the above variables and receive real-time feedback on predicted dimensions, the geometry of the affected region is often more complex than can be summarized with a few dimensions. Therefore, analytical solutions for the shape of the electric field distribution have been developed and are the current state-of-the-art on the NanoKnife® system. These solutions are able to mimic the shape of the electric field distribution from typical numerical simulations. The value of electric field contour is then matched to that seen from the numerical solution so that they both respond to their physical and pulse conditions in approximately the same manner. A calibration can then be used to adjust the size, and therefore various electric field thresholds (IRE, reversible, no electroporation, thermal damage) depicted to provide predicted affected regions. The practitioner may then adjust the variables such as voltage and separation distance (currently the only two that account for changes in predicted margins in the NanoKnife® embodiment), and see how the predicted affected margins vary in real-time. This provides the practitioner a much better method to find and place an appropriate electrode array with variable voltages to treat the entire region. There is also an optimization autoset probes function that places the probes and sets the voltage based on the number of probes selected and three dimensions input for the targeted region (assuming it to be a perfect ellipsoid).

The current state-of-the-art provides a very basic, fundamental explanation to practitioners about predicted treatment regions. Application of the current techniques in real-life clinical and experimental scenarios in which EBTs will typically be used provides to the practitioner helpful but inflexible tools.

For example, the analytical embodiment is a simple cross-sectional view of predicted margins at the center of the electrodes. This means that it cannot account for the falloff of electric field distribution (and therefore affected margins) at the tips of the electrodes. Although use of this approach can mimic the shape and size of these regions in 2D, it is not possible to accurately depict 3D scenario shapes in detail. Further, the lookup table cannot easily provide an accurate 3D shape, nor can the analytical solution be adapted.

True electroporation applications will increase the conductivity of the affected regions, which will in turn change the size and shape of the electric field distribution. A comparison of the electric field distribution (A,C) and conductivity map (B,D) of two identical numerical models without (A,B) and with (C,D) changing conductivity is shown in FIGS. 1A-D. From these figures, one can see how the conductivity increases from 0.1 S/m (the baseline level for the entire tissue domain, constant in part B) up to 0.155 S/m, an increase of 55%, for regions experiencing predicted IRE (deep red in part D), with regions experiencing varying extents of predicted reversible electroporation filling in between this (cyan through bright red). This change in conductivity in response to electroporation effects results in an altered electric field distribution, which may be seen in part C, where the distribution is larger, especially at the region between the electrodes. Changes in conductivity have been observed to reach several times higher than the baseline conductivity in the literature. These changes can be simulated in numerical solutions, and the general size changes can be accounted for with some accuracy in the analytical solutions by recalibrating them, but their shape is fixed, and cannot accurately reflect the predicted affected region's shape when considering changing conductivity.

Tumors will often have different electrical and physical properties than their neighboring tissues or even from their native tissues of origin (e.g., cancerous astrocytes which may not behave the same as normal ones). In addition, surrounding tissues of different tissue types will also have different properties from each other (bone, muscle, fat, blood). These differences in electrical properties will alter the electric field distribution for a given application of EBTs. Because the electric field to which the tissue is exposed is the primary determinant in the effect on the cell, these changes will change the shape and size of the affected regions. Numerical simulations are capable of modeling the electric field distribution in such heterogeneous systems. However, the rigid analytical solutions cannot be adjusted to account for such differences, and therefore could not as accurately predict affected regions for the different environments in clinical cases. The analytical solution, e.g., could not predict the differences between a tumor situated adjacent to the skull, the quadriceps muscle, or the heart. Although lookup tables could theoretically be developed for the dimensions of the affected regions in a number of environments, the great variability between the anatomy of each patient, each specific tumor, and each exact tumor location relative to its environment is impractical and futile.

FIGS. 2A-J demonstrate the effect of heterogeneous systems on electric field distribution. These figures show the electric field and temperature distribution for a three-dimensional numerical model. More particularly, FIG. 2J shows the model setup, where two needle electrodes (1 mm in diameter) are placed within the outer borders of a targeted region of tissue, surrounded by a peripheral region. The red and black regions on the electrodes represent the energized surfaces, where 4200 V was applied to one electrode and the other was set to ground. The thermal properties were set to represent a targeted region of a tumor within fat. The electrical conductivity for the targeted ($\sigma_t$) and peripheral ($\sigma_p$) tissues was manipulated between 0.025 and 0.25 S/m to establish conductivity ratios ($\sigma_t/\sigma_p$; relative conductivities of the targeted/peripheral region) of 0.1, 1, and 10. FIGS. 2A-I show the numerical model outputs for conductivity ratios ($\sigma_t/\sigma_p$) of 0.1 (A,D,G), 1 (B,E,H), and 10 (C,F,I); showing electric field (A-F) during the pulse and temperature (G-I) distributions 1 second after the first pulse. The higher conductivity ratios show progressively more area treated by IRE with less thermal effects. Targeted tissue boundary may be seen as the solid black line. Observing the electric field distribution at the boundary shows that the shape is also changing (not just size) as a result of the heterogeneous environment. Existing treatment planning systems are not capable of accounting for such dynamic tissue properties in real time.

The current embodiment of the treatment planning software still leaves it up to the practitioner to select a desired number of probes, but provides no simple method of showing how the optimized distributions will be shaped if the user wants to directly compare using different numbers of probes for a given lesion. The current system therefore also does not select the optimal number of probes for the user, a question that may be difficult to answer for more complex electrode geometries.

Temperature changes associated with Joule-type resistive heating of the tissue will also affect local regions conductivity based on its temperature (typically increases by approximately 3%/° C.). This will also change the size and shape of the electric field distribution based on the parameters used; including the number of pulses, pulse length, and repetition rate for an entire protocol (more pulses of longer length with higher repetition rates will all increase the thermally-associated conductivity changes, increasing this variation). Because the current treatment planning tools are based on simulations from the electric field distribution of a single application of a pulse, these dynamic conductivity behaviors also cannot be taken into account. Something that does would have to be able to simulate the changes that occur as a result of thermal effects on conductivity.

The current state of the art does allow the practitioner to describe the size/shape of the lesion in very basic dimensional terms (length, width, depth). This shape is then superimposed to scale with the predicted treatment regions, allowing a practitioner to ensure appropriate distribution and coverage. Although we have already pointed out the insufficiencies in handling this third dimension, it should also be pointed out that the basic ellipsoidal shape assumed by this system is wholly inadequate at describing the complex, often irregular, asymmetric geometries that tumors may take in clinical settings. The practitioner is thus left currently with assessing treatment protocol adequacy in 2D terms.

What is needed is a technique and system (or a series of independent systems) that allows a practitioner to accurately plan and implement in real time patient-specific treatment protocols which are capable of accounting for dynamic tissue properties and which can be used with accuracy and reliability in the clinical or experimental setting for EBTs.

SUMMARY OF THE INVENTION

The numerous limitations inherent in the planning system described above provide great incentive for a new, better system capable of accounting for one or more of these issues. If EBTs are to be seen as an accurate, reliable therapeutic method, then treatment planning methods and packages should be developed that can more accurately predict treatment outcomes with these considerations taken into account in a patient-to-patient basis.

The primary limitation to the above-mentioned, state-of-the-art treatment planning system is its need to provide treatment predictions in real-time, where a practitioner would be capable of changing the voltage or geometry parameters of a treatment protocol and immediately see how that impacts the entire treatment region. However, as more complex tumor shapes, sizes, and environments are encountered, real-time evaluation of superimposed treatment regions is cumbersome at best and inadequate to develop reliable therapies. Therefore, a more advanced system that allows treatment planning in advance of applying the therapy would be ideal to handling these detailed procedures. This allows for the adaptation of numerical solutions to provide treatment regions.

Accordingly, embodiments of the invention provide treatment planning systems, methods, and devices for determining a patient-specific electroporation-based treatment protocol comprising: a) a module operably configured to receive and process information from medical images of a target structure to prepare a 3-D reconstruction model of the target structure; and b) a module operably configured to perform a numerical model analysis using as inputs in the analysis the 3-D reconstruction and information from one or more of physical constraints, tissue heterogeneities, dynamic effects of electropermeabilization, dynamic thermal effects, or effects resulting from multiple treatments; and c) a module operably configured to construct one or more electrical protocols defining a treatment region and treatment parameters for effectively treating the target structure.

Further included in embodiments of the invention are treatment planning systems for determining a patient-specific electroporation-based treatment protocol comprising: a) a processing module operably configured for performing the following stages: 1) receiving and processing information from medical images of a target structure and preparing a 3-D reconstruction model of the target structure; 2) performing a numerical model analysis using as inputs in the analysis the 3-D reconstruction and information from one or more of physical constraints, tissue heterogeneities, dynamic effects of electropermeabilization, dynamic thermal effects, or effects resulting from multiple treatments; and 3) constructing one or more protocols each providing a treatment region with parameters for electroporating the target structure; and b) a processor for executing the stages of the processing module.

Such treatment planning systems can comprise a processing module capable of performing one or more of the stages in real time.

Information from medical images to be analyzed in treatment systems according to embodiments of the invention can be extracted from one or an array of images obtained from pathologic specimens or one or more imaging modalities chosen from radiographs, tomograms, nuclear scintigraphic scans, CT, MRI, PET, or US. The information from one or more of these sources can be compiled to prepare a 3D reconstruction of the target area, which is represented by a surface or a solid volume. The treatment planning systems according to embodiments of the invention can have as a target structure a) a targeted region or mass; or b) a targeted region or mass with neighboring regions; or c) a 3D map of voxels to be treated as independent elements in the finite modeling software.

Preferred numerical model analysis for treatment systems of the invention comprise finite element modeling (FEM). Even more preferred as treatment planning systems, wherein the numerical model analysis involves accounting for physical constraints, tissue heterogeneities, dynamic effects of electropermeabilization, dynamic thermal effects, and multiple treatment effects.

Even further, self-optimization algorithms for constructing the treatment protocols can also be incorporated into the inventive methods, systems, and devices. For example, the treatment planning systems can comprise a self-optimization algorithm which is capable of repeatedly evaluating one or more of physical constraints, placement of electrodes, electric field distribution simulations, and evaluation of outcome success until one or more effective protocol is constructed. It can also generate a predicted treatment time that will aid the physician in determining the optimal protocol.

According to some embodiments of the invention, the treatment planning systems can involve automatically, interactively, or automatically and interactively with or without user input determining the treatment region and parameters for electroporating.

Such treatment planning systems can also be capable of constructing protocols for an initial patient treatment or retreatment with or without additional medical images.

Treatment systems according to embodiments of the invention can also be adapted to instruct an electrical waveform generator to perform the protocol.

Such systems can further comprise an electrical waveform generator in operable communication with the processing module and capable of receiving and executing the treatment protocol.

Instructions for implementing the treatment protocols can comprise specifying a number of bipolar pulses to be delivered, a length of pulse duration, and a length of any delay between pulses. Additionally, the generators of such treatment systems can be operably configured for delivering a bipolar pulse train.

Methods and devices incorporating one or more of the features of the treatment planning systems according to the invention are also considered embodiments.

In particular, treatment planning methods can comprise: a) receiving and processing information from medical images of a target structure and preparing a 3-D reconstruction model of the target structure; b) performing a numerical model analysis using as inputs in the analysis the 3-D reconstruction and information from one or more of physical constraints, tissue heterogeneities, dynamic effects of electropermeabilization, dynamic thermal effects, or effects resulting from multiple treatments; and c) constructing an electroporation protocol based on results of the analyzing; wherein the receiving, processing, analyzing, and constructing is performed in real time.

Other methods may comprise method steps for reducing adverse effects of irreversible electroporation of tissue comprising administering electrical pulses through electrodes to tissue in a manner which causes irreversible electroporation of the tissue but minimizes electrical charge build up on the electrodes, or minimizes charge delivered to the tissue, or both. Adverse effects to be avoided may include, to name a few, one or more of thermal damage of the tissue, deleterious electrochemical effects, or electrolysis.

Preferred methods according to the invention may comprise electrical pulses comprising a series of unipolar and bipolar pulses with a net charge of zero. More particularly, the net charge of zero can be achieved by a change in potential direction for each pulse, or a change in potential direction within each pulse.

Further, electrical pulses generated in the methods can together comprise a pulse protocol comprising a train of unipolar pulses followed by a train of unipolar pulses of opposite polarity, or a train of bipolar pulses, or simultaneous unipolar pulses of opposite polarity which are offset from one another by a desired amount, or a combination of protocols.

Electrical pulses used in the methods, systems, and devices of the invention can have a waveform which is square, triangular, trapezoidal, exponential decay, sawtooth, sinusoidal, or of alternating polarity, or comprise a combination of one or more waveforms.

Control systems for electroporation devices are also considered embodiments of the present invention. Such systems can be configured to comprise: a) a processor in operable communication with a control module; b) a control module executable by the processor and in operable communication with an electrical circuit, wherein the control module is operably configured for initiating switching of the circuit at a rate of between 10 ms to 1 ns; and c) an electrical circuit operably configured to enable delivery of a voltage to an electrode and switching of the voltage to a second electrode to cause reversing of the polarity of the electric potential between the two electrodes.

Similarly, electroporation system embodiments of the invention can comprise: a) an electroporation device capable of delivering a first unipolar electrical pulse; b) the electroporation device further capable of, or a second electroporation device capable of, delivering a second unipolar electrical pulse which is opposite in polarity to the first unipolar pulse; c) a processor in operable communication with a control module; d) a control module executable by the processor and in operable communication with the electroporation device(s), wherein the control module is operably configured for initiating delivery of the first unipolar electrical pulse at a time 1 and for initiating delivery of the second unipolar electrical pulse at time 2 offset from time 1 by 1 second to 1 nanosecond.

Electroporation devices can also be operably configured to enable delivery of an electrical pulse to a first electrode, switching of the pulse to a second electrode to cause reversing of the polarity of the electric potential between the two electrodes, and switching of the pulse back to the first electrode or to zero, wherein a cycle of switching is established which cycle is capable of being performed at a rate of between 10 milliseconds to 1 nanosecond.

Such devices, systems, and methods can be configured to provide for switching to occur between or within the electrical pulse. Devices, for example, can be configured such that the electrical pulses together comprise a pulse protocol comprising a train of unipolar pulses followed by a train of unipolar pulses of opposite polarity or a train of bipolar pulses.

BRIEF DESCRIPTION OF THE DRAWINGS

FIGS. 2A-I are schematic diagrams showing the numerical model outputs for conductivity ratios ($\sigma_t/\sigma_p$) of 0.1 (A,D,G), 1 (B,E,H), and 10 (C,F,I); showing electric field (A-F) during the pulse and temperature (G-I) distributions 1 second after the first pulse.

FIG. 2J is a schematic diagram showing placement of the electrodes in the targeted tissue for the set up illustrated in FIGS. 2A-I.

FIG. 11A is a schematic representation of an electric field distribution map, showing a top view of the electrodes of FIG. 10 in an energized state.

FIGS. 21A-H is a graphic representation of a three-dimensional (3-D) solid representing a tumor volume and displaying the voltage configurations that would mainly affect tumor tissue in this particular situation.

FIGS. 24A-G are graphs showing various pulsing protocols according to the invention, demonstrating exemplary frequencies, pulse length, and time delay between pulses.

FIG. 27A depicts a two-dimensional display for the use of four electrodes of alternating polarity. FIG. 27B depicts an axis symmetric display for the use of four similar electrodes of alternating polarity. FIG. 27C depicts a two-dimensional display for the use of four charged electrodes, the center two at 5000V and 0V and the outer two at 2500V. FIG. 27D depicts an axis symmetric display for the use of a similar electrode set up as FIG. 27C. FIG. 27E depicts a two-dimensional display for the use of three electrodes with the center one at 2500V and the outer two at 0V. FIG. 27F depicts an axis symmetric display for the use of three electrodes similar to Panel E. FIG. 27G depicts a two-dimensional display for the use of three charged electrodes, the center at 0V, the left at 5000V, and the right at 2500V. FIG. 27H depicts an axis symmetric display for the use of a similar electrode set up as Panel G. FIG. 27I depicts a two-dimensional display for the use of three charged electrodes, the center at 1750V, the left at 3000V, and the right at 0V. FIG. 27J depicts an axis symmetric display for the use of a similar electrode set up as FIG. 27I.

FIGS. 34A-C are schematic diagrams showing electric field, norm (V/cm) contours predicted by the FEM during a 1000 V amplitude burst with a center frequency of 1 kHz (FIG. 34A) and 1 MHz (FIG. 34B). In FIG. 34C, the homogeneous solution is shown for a constant pulse.

FIG. 35 depicts electrical field outputs from various configurations employing two electrodes. FIG. 35E depicts a side view of electrical field outputs from one device having two electrically conductive regions separated by an insulative region of a length of 0.5 cm.

DETAILED DESCRIPTION OF VARIOUS EMBODIMENTS OF THE INVENTION

Figure 1A:
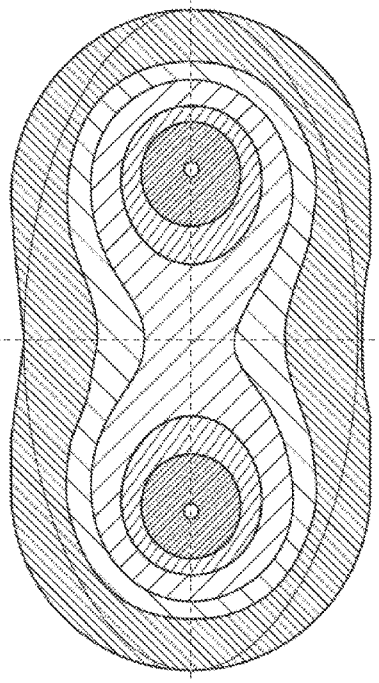
FIGS. 1A-D are schematic diagrams comparing the electric field distribution (A, C) and conductivity map (B,D) of two identical numerical models without (A,B) and with (C,D) changing conductivity.
Figure 1C:
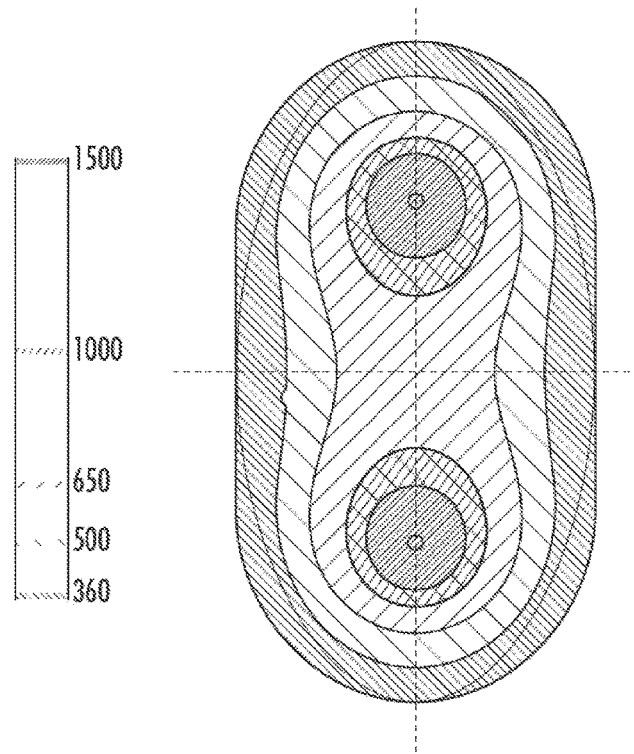
Figure 1B:
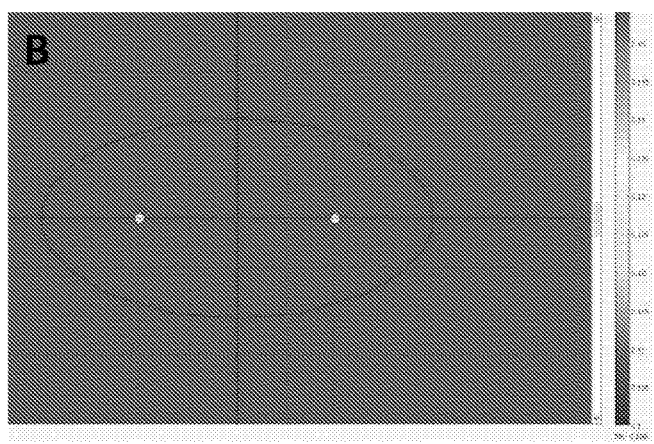
Figure 1D:
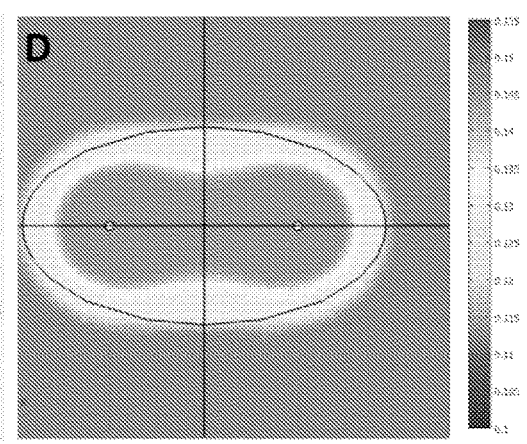

Irreversible electroporation (IRE) is a new focal tissue ablation technique. The treatments are capable of sparing major blood vessels, extracellular matrix and other sensitive or critical structures. The procedure involves the delivery of low-energy electric pulses through minimally invasive electrodes inserted within the tissue. The target tissue is exposed to external electric field distributions around the electrodes, which alter the resting transmembrane potential of the cells. The degree of tissue electroporation (i.e., no effect, reversible electroporation and/or irreversible electroporation) depends on the magnitude of the induced transmembrane potential.

Numerical models for electric field optimization are available and typically include the physical properties of the tissue and treatment parameters including electrode geometry and pulse parameters (e.g., duration, number, amplitude, polarity, and repetition rate). These models can also incorporate the dynamic changes in tissue electric conductivity due to electroporation and thermal effects.

In embodiments of the invention there is provided a numerical model to visualize the IRE treated regions using sequential independent combinations of multiple energized and grounded electrodes. Specifically, in such models electric conductivity changes due to electroporation and thermal effects from an IRE pulse sequence are capable of being incorporated into the analysis for developing and constructing more effective treatment protocols. A particular embodiment involves setting the resulting conductivity distribution as the initial condition for the next pulse sequence, then repeating this procedure sequentially until all the pulse sequences are completed. In this manner, electric conductivity dependencies from previous pulses are incorporated and more accurate electric field distributions are presented. It is important to note that it is assumed that once a tissue is irreversibly electroporated, the tissue conductivity would not revert back. Consequently, a comprehensive IRE distribution can be presented in which the conductivity changes due to the previous pulses are considered. Such methods are most useful when using three or more electrodes with electrode-pairs being energized independently.

The electric conductivity map in certain circumstances can be crucial in the treatment planning of irreversible electroporation and other pulsed electric field therapeutic applications. The conductivity map is what determines how the current generated by the applied voltages/potentials will flow and the magnitude of the electric field. Several factors affect this distribution before, during and after the treatment including tissue heterogeneities, electropermeabilization, thermal effects and multiple treatments.

First, each tissue has its own "resting/unique" electric conductivity before the application of the electric pulses. Thus, in any particular organ or system there could be a mixture of conductivities that need to be accounted for in the treatment planning as in the case of white matter, gray matter and tumor tissue in the brain for example. Also, due to the permeabilization of the cells in the tissue that are exposed to an electric field threshold capable of altering the membrane structure, there is an increase in conductivity as well (electroporation effect). In addition, each of the tissue's conductivity will vary with changes in temperature as is the case for brain (3.2% $C^{-1}$) or liver (2% $C^{-1}$).

The main region treated by irreversible electroporation does not have sufficient increase in temperature to generate thermal damage, however, at the electrode tissue interface (where the electric field is highest) there is a significant increase in temperature and thus the conductivity map is altered. Capturing these and other dynamic effects can be crucial since they represent more accurate/realistic treatment geometries and pulse parameters that are not captured elsewhere. Accounting for these effects in treatment planning software is expected to lead to the optimization of pulse parameters and minimize damage to surrounding healthy tissue.

Numerical modeling methods, such as finite element modeling (FEM), are more accurate and are actually where the previous treatment planning systems derive their solutions (the lookup table and analytical solutions are calibrated to mimic the numerical solutions).

The reason numerical solutions were not implemented previously is that software packages to do so can be expensive, can take extensive periods to come up with a solution (inhibiting real-time feedback as was the goal above), and require familiarity with complex software in order to develop protocols (practically requiring an engineer to develop the plans). Because the direction of EBTs is toward application in more complex settings where more accurate solutions are desirable and take priority over time for development, the system described in this disclosure is one that can be performed with numerical solutions by developing the treatment plan well in advance (hours, days, weeks, or months) of its implementation.

Example I

General Stages of Planning Electroporation-Based Treatments.

A canine patient with a 360 cm³ tumor in the left thigh was treated according to a treatment planning embodiment of the invention. This treatment plan serves to demonstrate the complexity and numerous steps typically involved in developing and implementing a comprehensive treatment plan for electroporation-based therapies. This description is intended to provide guidance as to the formulation of a basic treatment planning system, which can be operably configured to include one or more of the following stages:

Image Acquisition.

Images of the target lesion or of a portion of the body to be treated can be acquired by taking an array of medical images using one or more imaging modalities, including CT, MRI, PET, or US to name a few.

Figure 3:
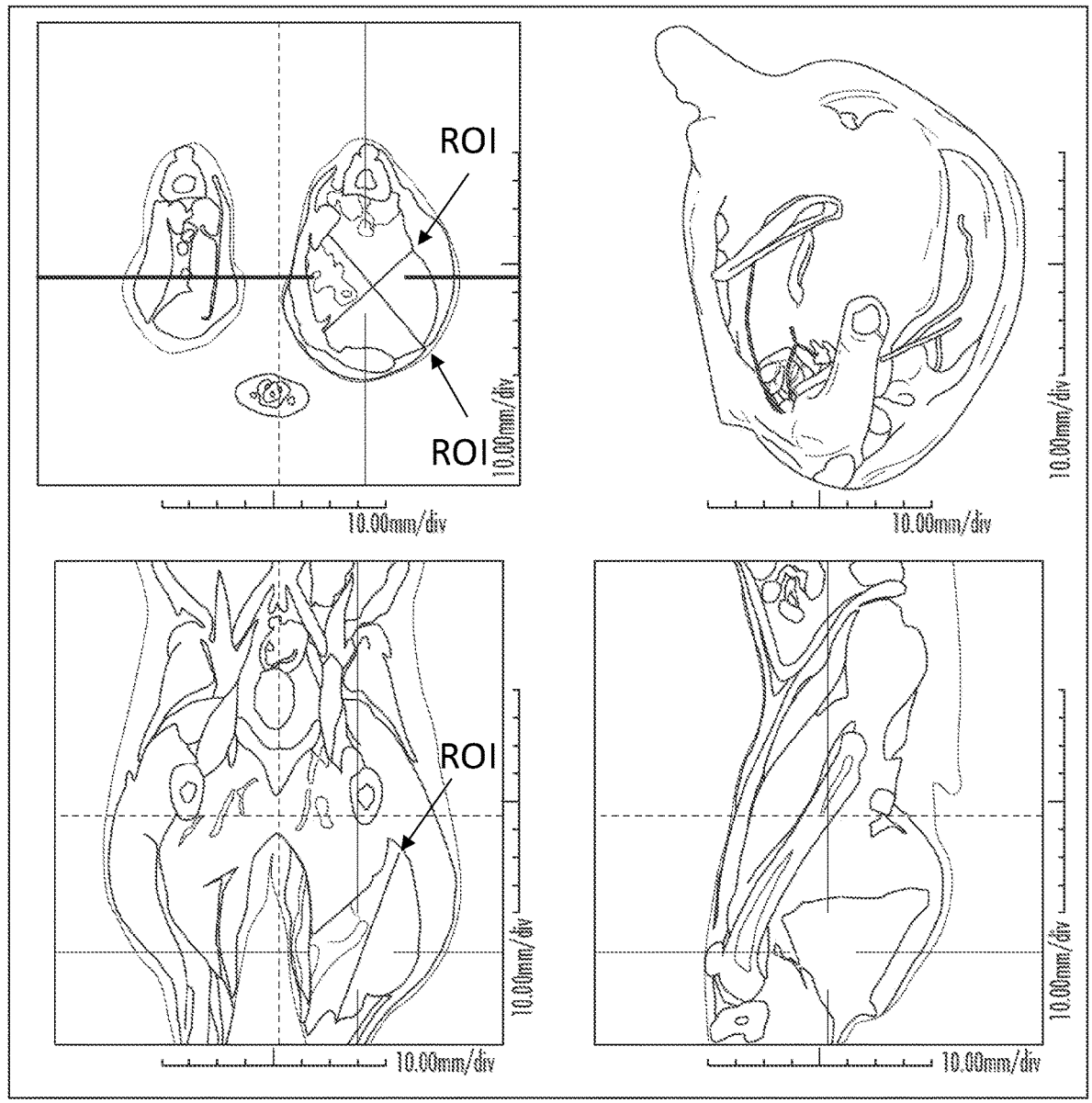
FIG. 3 is a series of CT images showing the presence of a tumor in the left thigh of the canine patient of Example I.

As shown in FIG. 3, in preparation for isolating and reconstructing a target region, an imaging modality such as computed tomography CT can be used to determine the presence of a tumor. Using an image or series of images, information about or relating to the region of interest can be collected and used to determine a targeted region, its location, its position, any important or relevant nearby structures that must be accounted for (such as blood vessels, nerves, collecting ducts, etc.), and any relative basic dimensions (such as depth within tissue, basic cross-sectional sizes, distance from other structures, etc.). The CT images shown in FIG. 3 have used axial slices with TeraRecon software to compile the pixels into voxels and develop other sectional slices as well as an overall 3D reconstruction of the scans based on radiodensity (though individual regions of interest have not been isolated). Other imaging modalities such as ultrasound or MRI may also be used to assess the lesion.

Regions of Interest (ROI) Tracing.

Figure 4:
FIG. 4 is a CT image from FIG. 3, within which the region of interest is traced.

The target ROI can be outlined in the images used to identify the tumor, whether manually or by way of a computer program, to identify a potential treatment area. For example, a computer program capable of detecting anomalies, such as the OsiriX open-source image analysis software (Geneva, Switzerland), could be used to outline the targeted region (e.g., a tumor, site for electrogenetransfer, etc.). As shown in FIG. 4, one of the CT scans from FIG. 3 is shown with the region of interest traced. Tracing the region of interest in each of a series of CT images compiling the 2D traces of each slice would allow for compilation of 3D geometry for the target region.

Visualizing and Reconstructing 3D Geometry.

The traced regions of interest from a series of axial CT slices can be compiled and interpolated between the steps to create a three-dimensional geometry that the practitioner could use to gain an understanding of the basic shape of the target mass and/or its location relative to other tissues.

Figure 5:
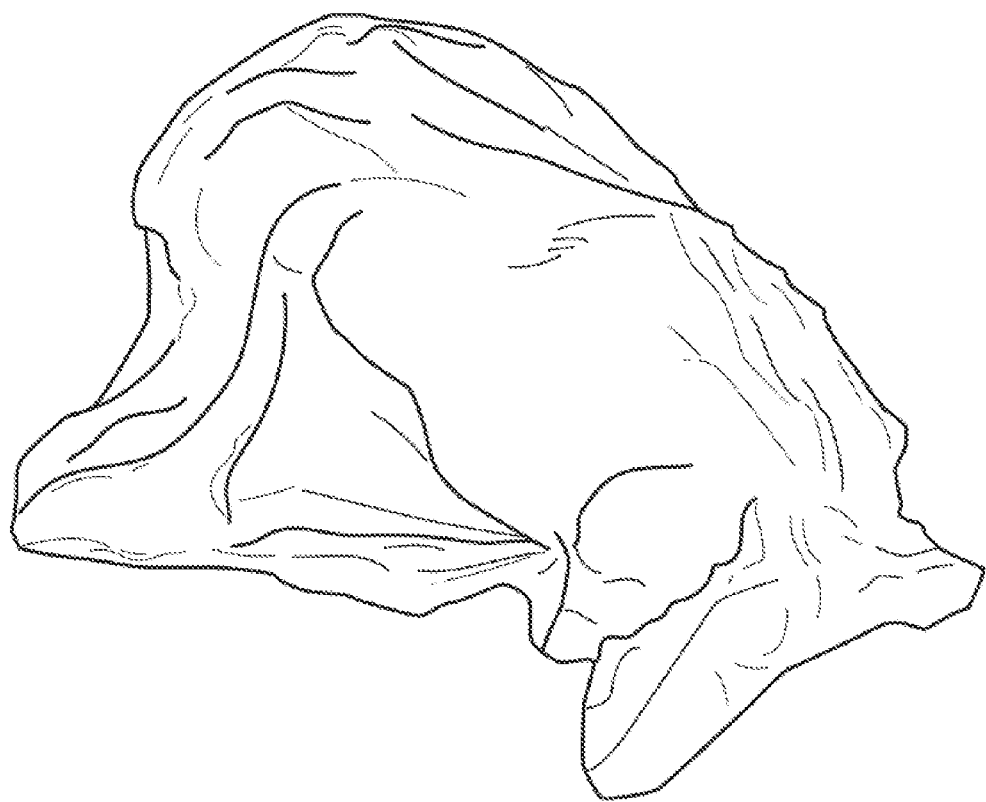
FIG. 5 is a drawing of a 3D reconstruction of the target region of Example I, which was reconstructed by compiling a series of axial traces to create a representative shape of the targeted region in three dimensions.

FIG. 5 shows a series of axial traces having been compiled to create a representative shape of the targeted region in three dimensions. This reconstruction may be maneuvered to assess its general shape and thus allow determination of potentially efficient electrode insertion approaches.

Figure 6:
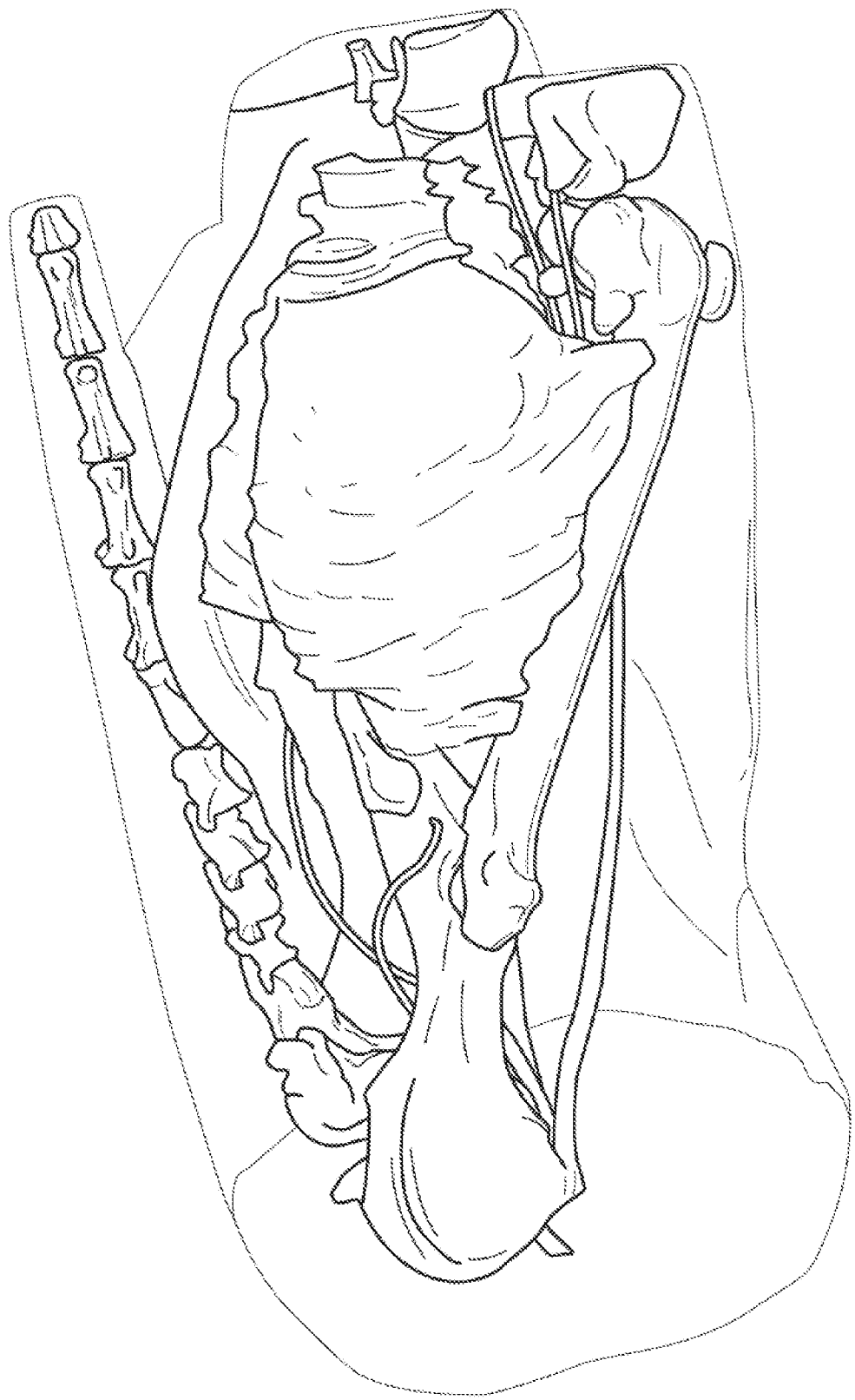
FIG. 6 is the drawing of the 3D reconstructed geometry shown in FIG. 5 visualized relative to the rest of the patient.

If desired, the reconstructed geometry can also be visualized relative to the rest of the patient. This allows one to assess (in greater detail than the initial FIG. 3 images) physical constraints such as bones preventing electrode insertion, relative location of sensitive structures, and orientation of the lesion relative to the body, allowing a practitioner to evaluate optimal electrode insertion approaches. For example, in FIG. 6, the long axis of the tumor is roughly parallel to the length leg and femur, so a user may consider reducing the number of electrodes and insertions used by orienting the electrodes along this axis, or they may go with more electrodes perpendicular to the top of the leg (since the femur prevents access from the bottom of the leg).

Geometry Modeling.

The 3D geometry can then be imported into finite element modeling software (FEM). Indeed, several geometries can be imported using software such as Comsol Multiphysics (Comsol, Stockholm, Sweden), including: a) just the targeted region or mass; b) the targeted region and other traced neighboring regions (muscle, fat, bone, etc); or a 3D Map of all the voxels to be treated as independent elements in the finite modeling software. The coordinate system from the medical images can also be matched.

Figure 7:
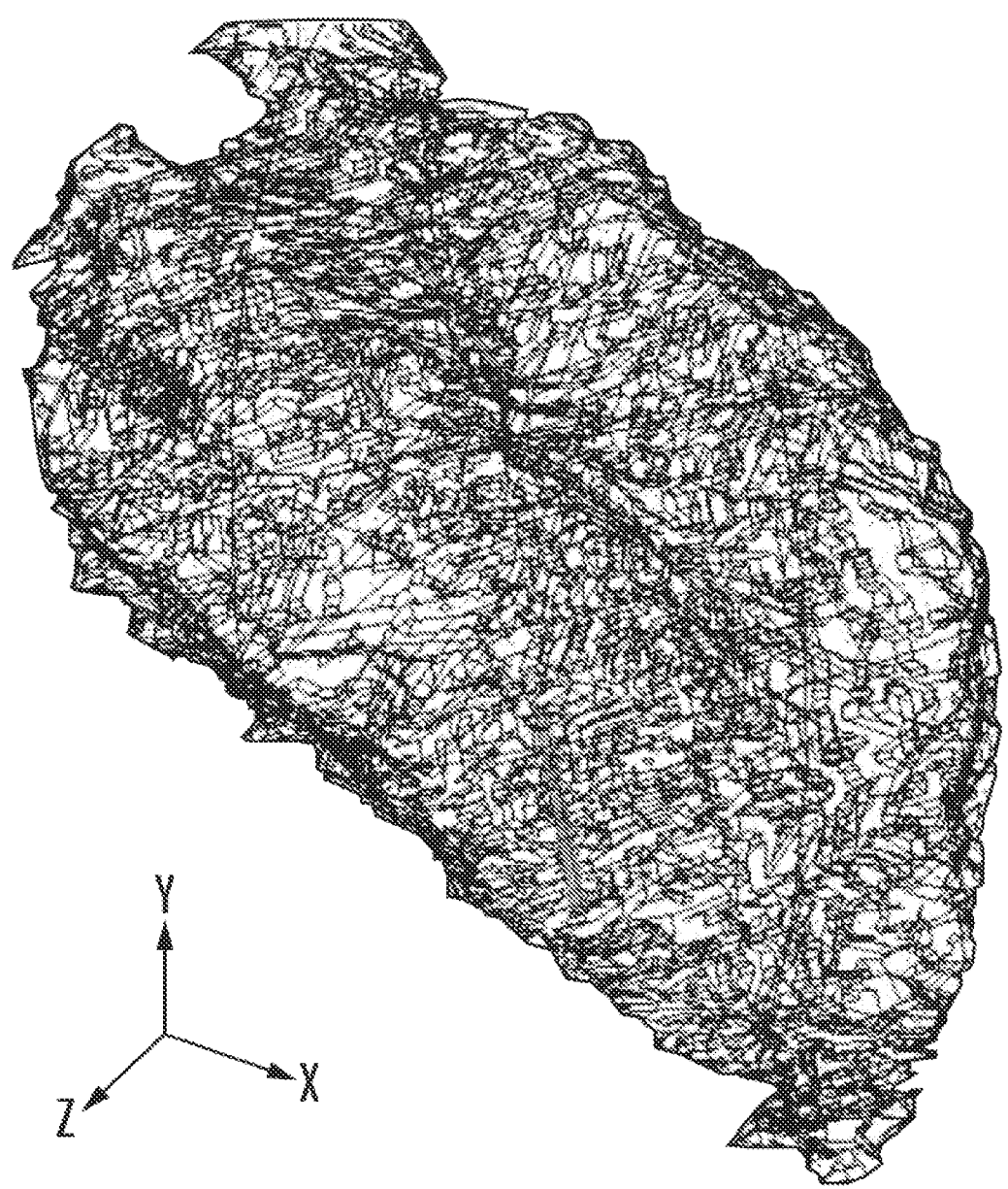
FIG. 7 is a graphic representation of the 3D reconstruction of FIG. 5 as imported into and converted within Comsol Multiphysics.

FIG. 7 shows a model of the 3D target geometry as imported into numerical modeling software. More particularly, the geometry developed and shown in FIG. 5 may be converted to a surface or a solid and imported into numerical modeling software. Here, the black shape is a converted geometry within Comsol Multiphysics for the targeted region reconstructed above. Its dimensions and volume have been normalized to ensure its size matches that of the reconstructed volume.

Assign Model Properties.

Any physical and/or thermal properties and/or electrical properties can be assigned in numerous ways. For example, the properties can be assigned arbitrarily; deduced by designating which of the target region or the other traced neighboring regions are of what tissue type and using properties of these tissue types from the literature; experimentally measured with a "pre-pulse" (e.g., as described in U.S. patent application Ser. No. 12/491,151, "Irreversible Electroporation to Treat Aberrant Cell Masses;" or the properties can be derived from an algorithm or coordination scheme based on voxel or pixel value imported from the 3D map.

The assignment of properties to the model can be performed within software and manually accounted for in placements. If such properties are either assigned arbitrarily or are deduced as described above, the different shapes depicted in the model (e.g., FIG. 7) may each be assigned a different set of properties to best represent the tissue or material used (such as 0.025 S/m for the fatty tumor, and 0.5 S/m for the surrounding tissue).

In a preferred embodiment, the tissue properties are derived from medical images. Due to the properties of tissue and how the tissues are assessed by modern imaging techniques, it may be possible to derive accurate estimations of a tissue's properties based on its response to the various imaging modalities.

For example, for computed tomography, pixel values are based on the radiodensity of the tissue at that point in the image (its attenuation). It is common practice to scale these attenuations relative to distilled water according to the equation:

$$HU = \frac{\mu_X - \mu_{water}}{\mu_{water} - \mu_{air}} \times 1000$$

where $\mu_X$, $\mu_{water}$, and $\mu_{air}$ are the linear attenuation coefficients of that point in the tissue, water, and air, respectively. Essentially, this system normalizes the radiodensity of all tissues relative to water.

A tissue's Hounds Unit (HU) value may serve as a representation of its relative water content, with larger absolute value HU's (because it can be negative as well) containing less water. Thus, one could determine (with some noise) a function of HU that goes in the domain from −1000 (air, minimal radioattenuation) to +1000 (an equivalent difference of higher radioattenuation), where the curve estimates the water content. The data in Table I supports this concept.

TABLE I

| Substance | HU | Conductivity, S/m (from literature) |
|---|---|---|
| Air | −1000 | 0 |
| Fat | −120 | 0.025 |
| Water | 0 | — |
| Muscle | +40 | 0.5 |
| Bone | >+400 | .0025 |

These are general evaluations of conductivity. It does not matter what the conductivity of distilled water μs, but it would likely be taken to be that of physiological saline for conductivity estimation (1.2 S/m). From qualitatively assessing the data in Table I, it can be seen that the closer a tissue's HU is to 0, the higher its conductivity. This is also reflected because it is known that muscle has a higher water content than fat, which is closer to the HU of 0 and a higher conductivity, while bone having the least water content of all, is the least conductive.

Figure 8:
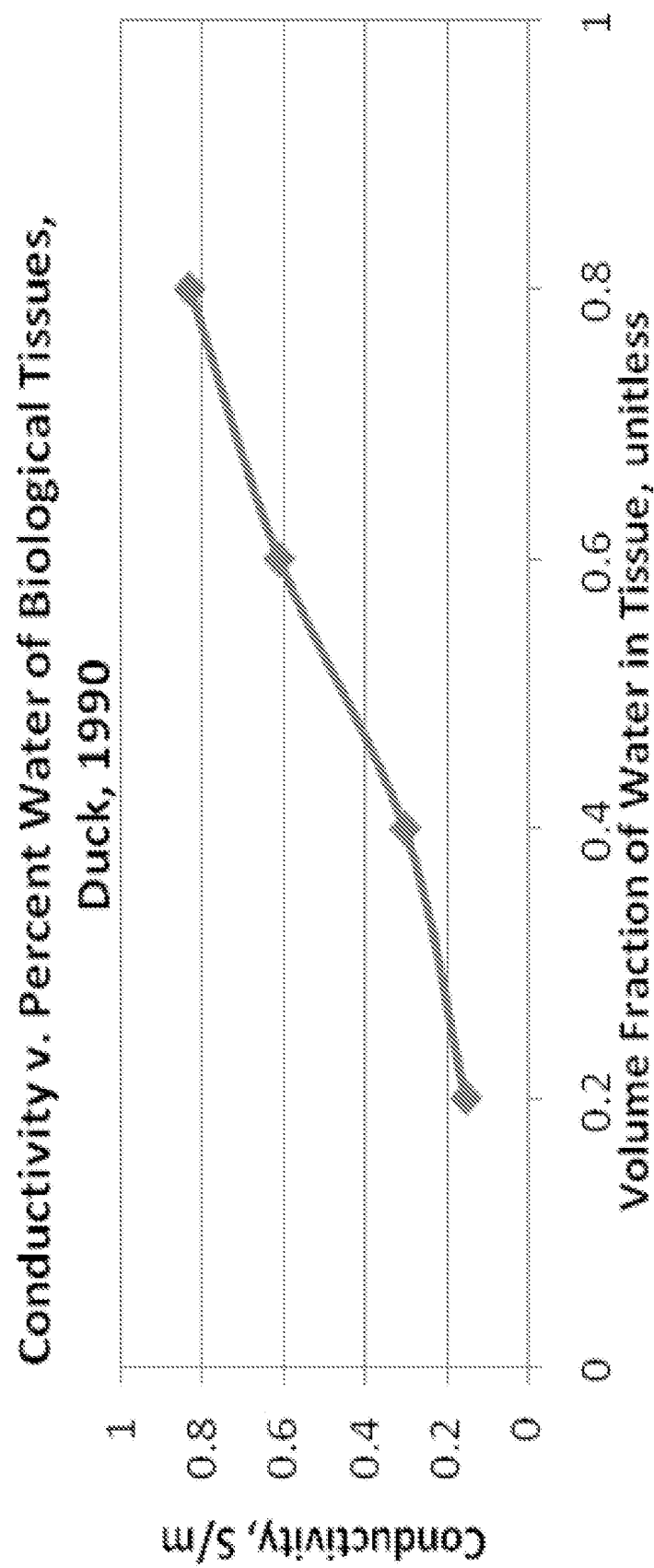
FIG. 8 is a graph from Duck, 1990, showing the relationship between conductivity and %-water, which may also be used to estimate a tissue's electrical properties.

Although not a comprehensive table, the trends are clearly evident that one may be able to fit an interpolation function between HU and conductivity. With further exploration, it may be seen that this may be a result of higher volumetric water concentrations having higher conductivity. The idea that higher percentage of water causes a tissue to have a radiodensity more similar to that of water is an assumption, but when taking it into account, the relationship between conductivity and %-water may also be used to estimate the tissue's electrical properties, as described in Duck, 1990 (FIG. 8).

Evaluate any Physical Placement Constraints.

Potential physical placement constraints, such as vital structures (nerves, brain, blood vessels, etc.), access orientation preferences (from head, from rear, supine, prone patient positioning, etc.), and/or physical barriers (bones, sensitive structures, etc.) can be identified. The potential constraints can then be used to guide/constrain what angles are possible for the electrodes and if the electrodes should be placed to avoid certain areas more than others.

Figure 9:
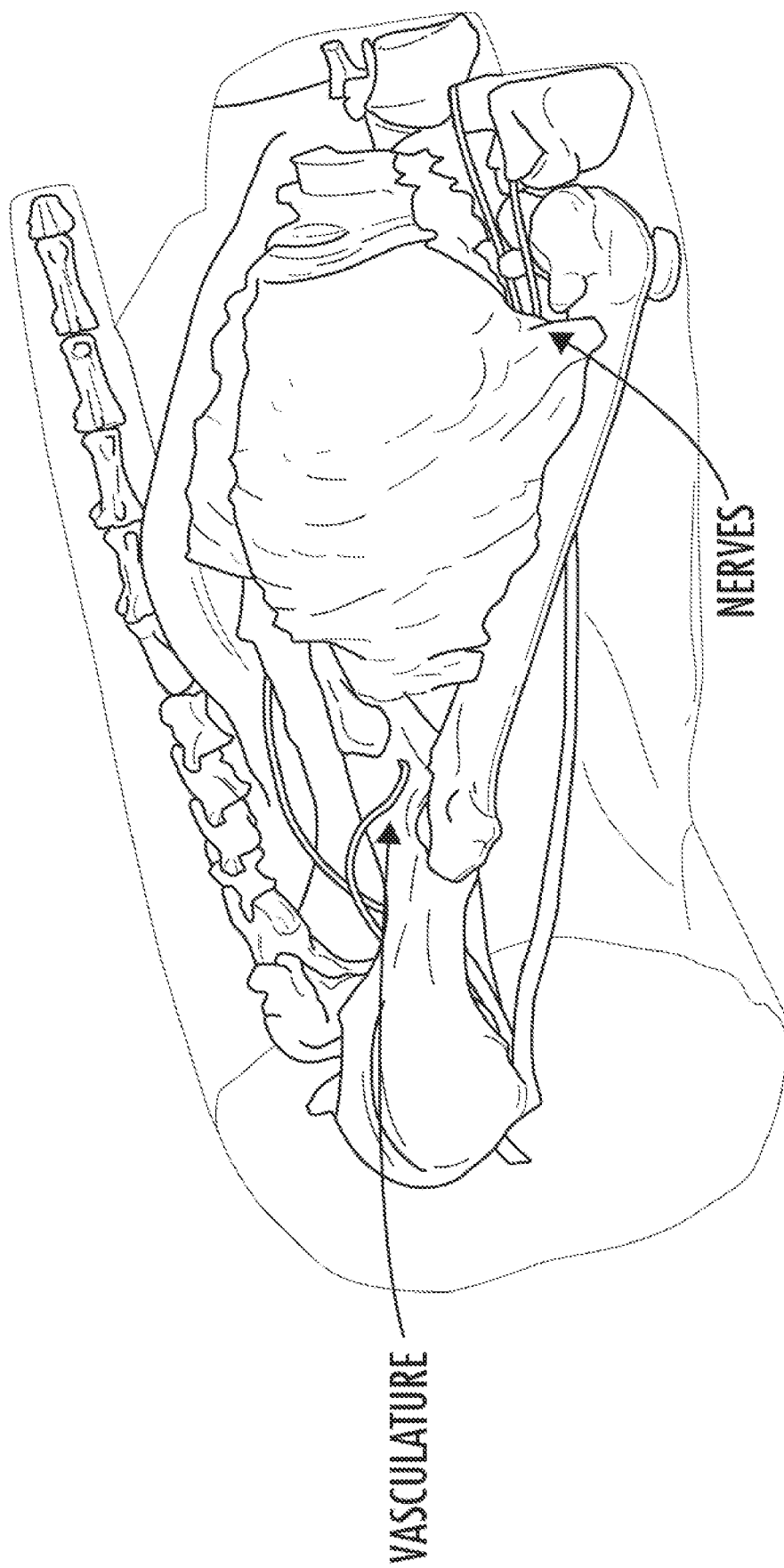
FIG. 9 is the drawing of the 3D reconstruction of the target tumor of FIG. 5 visualized in relation to surrounding structures within the body, which is a tool useful for developing treatment constraints.

FIG. 9 shows a graphic 3D reconstruction of the target tumor in relation to surrounding structures within the body, which is useful for developing treatment constraints. The physical location of the tumor relative to the rest of the body (shown in FIG. 9 by arrows pointing out vasculature and nerves, for example) can be demonstrated using the previously prepared 3D geometric representation of the tumor. This information may be used to constrain or direct where the electrodes should be placed and give priority to regions that should be spared relative to regions that would not cause as significant of problems.

Placement of Electrodes.

Any number of electrodes could be placed into or around the targeted region. Their number, location, orientation, and size could all be adjusted independently.

Figure 10:
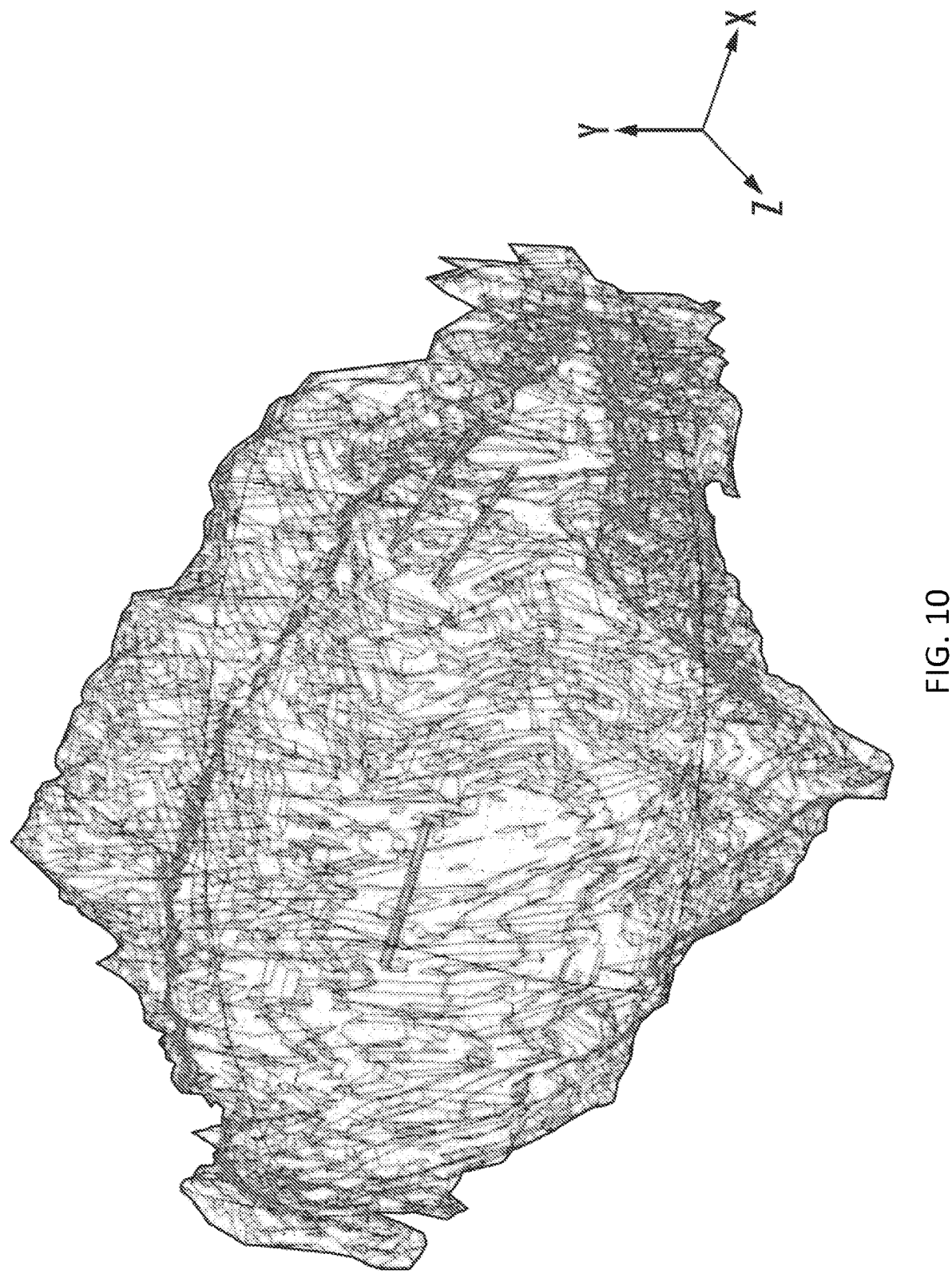
FIG. 10 is a graphic representation of the 3D reconstruction of FIG. 5 as imported into and converted within Comsol Multiphysics and further including a demonstrative electrode placement for an exemplary treatment protocol.

FIG. 10 is a graphic 3D representation of the imported tumor geometry with electrodes placed. Here, the geometric representation of the targeted region is depicted in red, while representations of electrodes are shown at two locations in blue. The number, orientation, and location of these electrodes is capable of being manipulated to satisfy the desired treatment objectives.

Simulation of the Electric Field Distribution.

Simulation of the electric field distribution (e.g., numerically solved electric field distributions) are capable of being correlated with experimental data to superimpose predicted volumes of affected regions (treated, untreated, thermal damage).

For example, FIG. 11 shows the electrodes depicted in FIG. 10 in an energized state. For the electrode on the left, a section on the end has been set to a voltage while a section on the rest has been set to ground with a section of insulation between, creating a voltage gradient that surrounds the single needle. For the pair of electrodes on the right, the entire length of one electrode has been set to a voltage while the other electrode has been set to ground, creating a voltage gradient between them.

The color maps are representative electric field isocontour regions that may be used in determining predicted treatment regions, reversible regions, or safety margins based on electric field thresholds. For example, if the protocol anticipates an IRE electric field threshold of 500 V/cm, then the entire volume of the tissue exposed to this electric field or higher (depicted in green) would be the predicted treatment region. In addition, if it were desired to ensure sparing of a sensitive structure such as a nerve, and an exact resolution of the above-predicted 500 V/cm IRE electric threshold was insufficient to guarantee sparing, a different electric field may be used to predict a safety margin which would be used to ensure that this threshold is not crossed by the sensitive structure (such as 250 V/cm depicted in red).

Figure 11B:
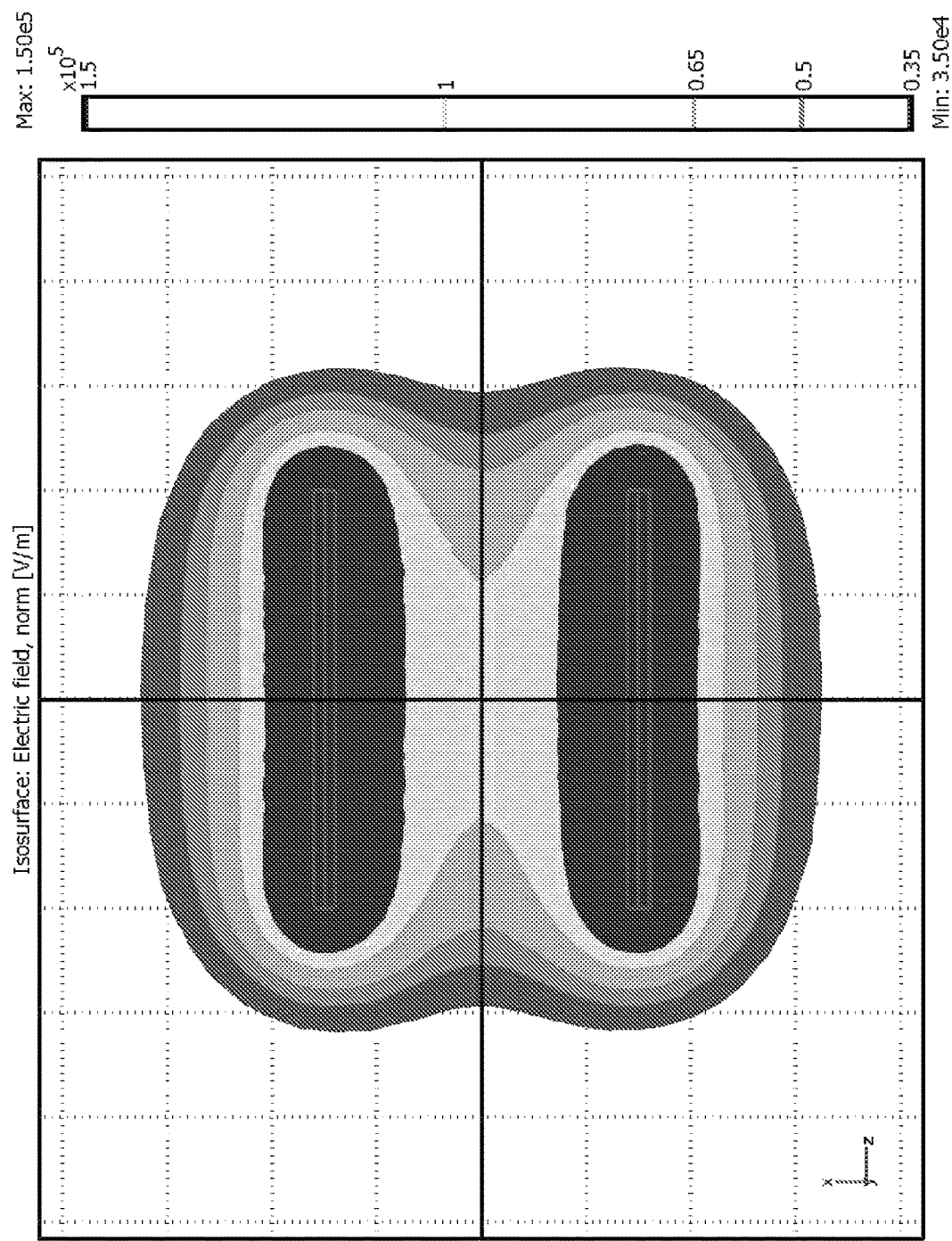
FIGS. 11B-D are schematic diagrams demonstrating fall-off of the electric field distribution in the third dimension, showing an exemplary electric field distribution in the xz-plane (FIG. 11B), in the xy-plane at the midpoint of the electrodes, and in the xy-plane at the tips of the electrodes.
Figure 11C:
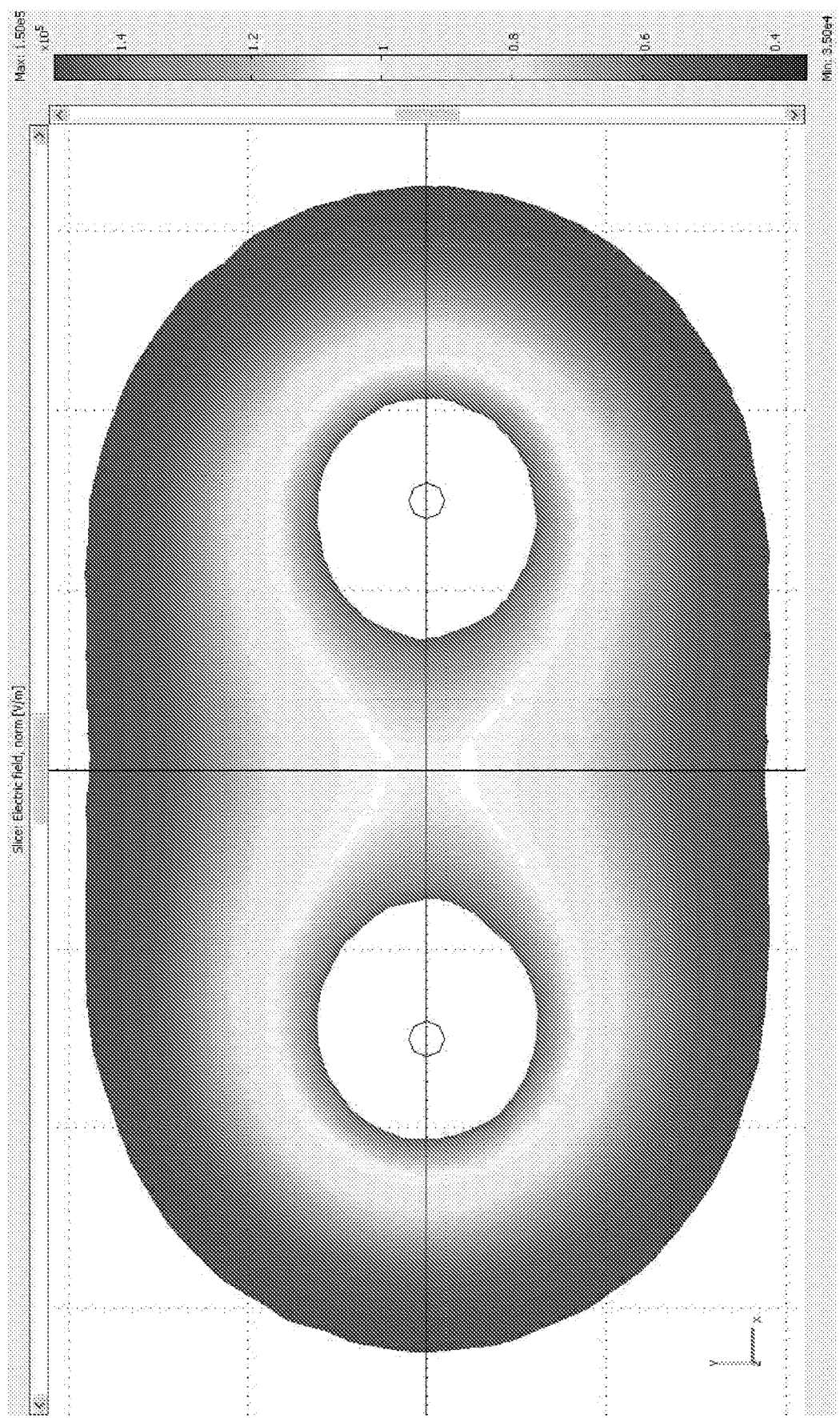
Figure 11D:
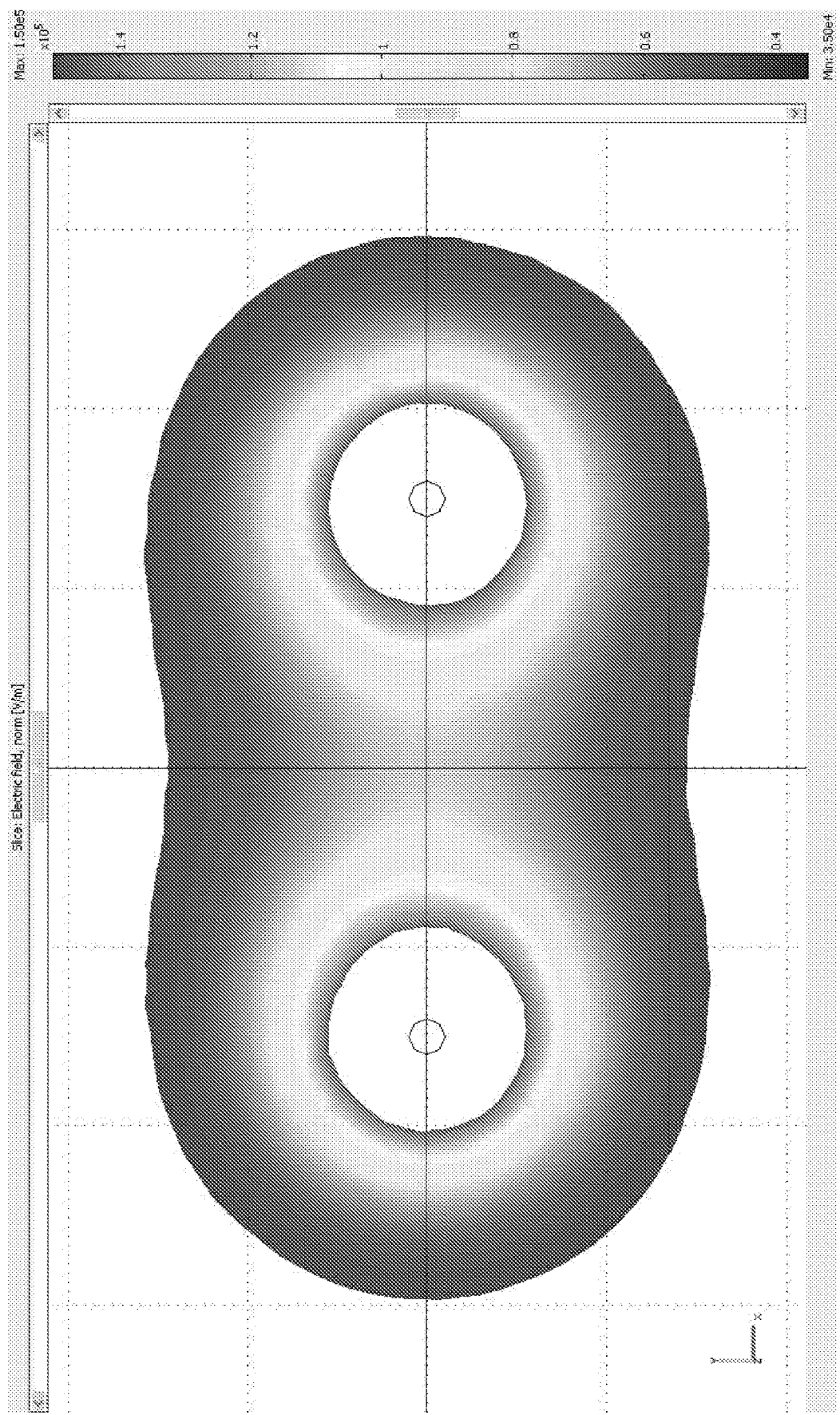

Another factor to consider in any analysis for determining proper placement of the electrodes and/or the charge needed for a particular application is the expected behavior of the electric field relative to the electrodes. As shown in FIGS. 11B-D, the electric field distribution is typically at a maximum at the cross-sectional region midway between the lengths of the electrodes and tapers off toward the ends of the electrodes.

More particularly, the image shown in FIG. 11B shows the electric field distribution between 35000 and 150000 V/m looking at both electrodes simultaneously in the xz-plane. The grey rectangles are the electrodes, running along the z-axis, and separated by 1.5 cm (center-to-center) along the x-axis. Here, one can see that the electric field is greatest at z=0, and decreases as one moves towards the tips of the electrodes. The 2-dimensional cross-sectional estimates are calibrated to represent the electric field distribution at z=0, and do not take into account the losses that occur over the length of the electrode.

FIGS. 11C and D in comparison show x-y cross-sectional plane view of the electric field distribution at z=0 and the x-y cross-sectional plane view electric field distribution at z=1 cm (the tips of the electrodes), respectively. By comparing these two distributions, it can be seen that the electric field distribution decreases as distance from the center of the electrode lengths increases. To accurately predict the treatment regions in three dimensions, these differences should be taken into account for the overall 3D nature of treatments. The methods, systems, and devices according to the invention include consideration of this factor.

Evaluate Success of Outcome.

Determine whether the setup used appropriately meets its treatment demands of affecting the desired regions while preventing unacceptable effects on untargeted and sensitive regions. This could be assessed qualitatively or quantitatively with a fitness function.

Optimization.

The evaluation of physical constraints, placement of electrodes, simulation of the electric field distribution, and evaluation of outcome success can be repeated until a suitable solution is developed. This optimization stage can be performed manually (interactively) by a practitioner or automatically. The Optimization Quality Function of Formula I discussed in more detail below could also be used for manual optimization.

Figure 12A:
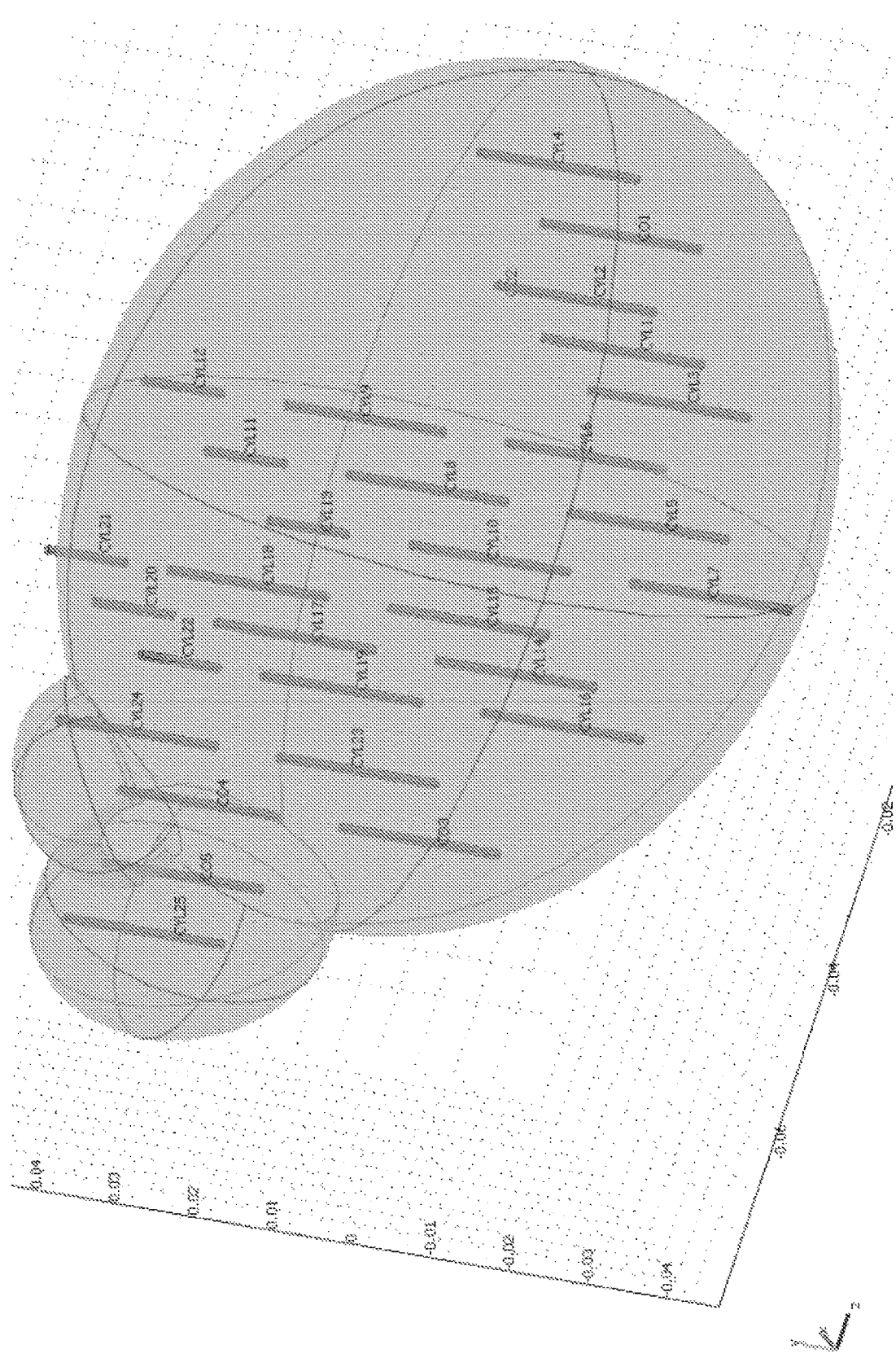
FIG. 12A is a schematic drawing showing a representative geometry of the treatment area in which compiled ellipsoids (shown in pink) illustrate the electroporation protocol developed to attain the desired treatment objectives.

In this embodiment, the optimization phase of the system was performed qualitatively and was iterated with the previous four steps until settling on the electrode array shown in FIGS. 12A and B. In this embodiment, the resultant representative geometry of compiled ellipsoids (shown in pink) illustrates the satisfactory electroporation protocol developed in order to attain the desired treatment objectives. In FIG. 12A, it can be seen that a highly complex array of electrodes (blue) was selected, where some electrodes are inserted and exposed an amount (such as 1 or 2 cm), to treat an amount of depth with pulsing, before withdrawing them some and repeating the pulsing. This was done to ensure complete treatment along the depth of the treatment. The blue cylinders depict discrete electrode placements for pulsing, and the ones stacked on top of each other represent this aspect.

Figure 12B:
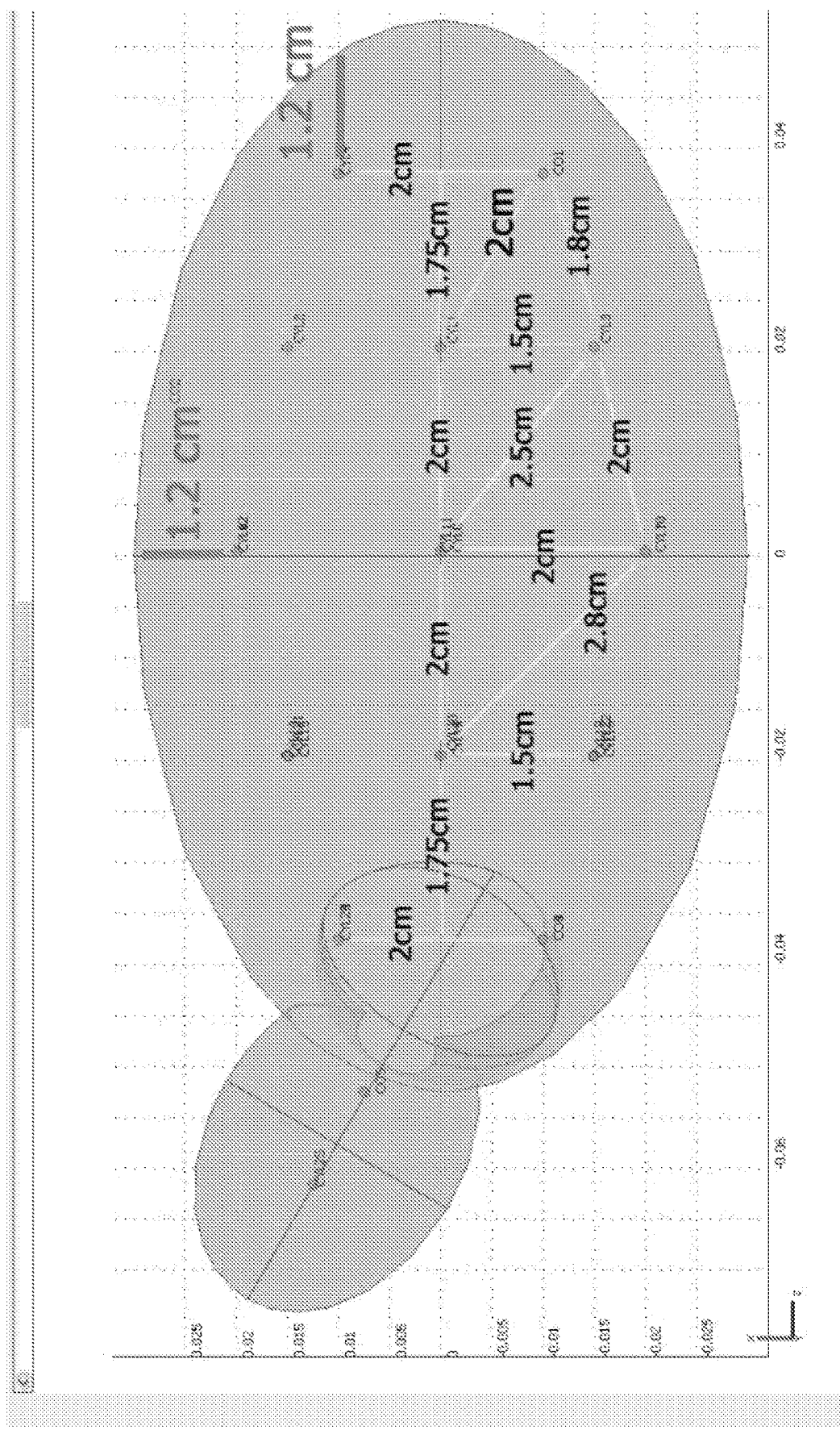
FIG. 12B is a schematic drawing showing a top view of the treatment area geometry shown in FIG. 12A, and further demonstrating the electrode insertion paths.

Further, as shown in FIG. 12B, a top view of the graphic representation of the treatment area of FIG. 12A is provided, in which the electrode insertion paths can be seen. Since the electrodes were all running perpendicular, spacing dimensions have been outlined to aid the placement of the electrodes for the practitioner. The pulses would be administered between each electrode and the electrodes in closest proximity to it. Electric pulse parameters are adjusted between each electrode firing pair based on separation distance and the desired treatment region (based on targeted volume and avoidance of sensitive tissues). The dimensions in red are also used as guidelines for the placement of the outer electrodes relative to the margins of the tumor to prevent excessive treatment of peripheral (untargeted) regions.

Implementation.

Once a desired solution has been developed, the generator system for applying the designated pulsing protocol can be set up for implementation of the desired protocol. More particularly, the practitioner could then place the electrodes according to the prescribed protocol and let the generator apply the pulses.

Also during implementation, the systems, methods, and or devices according to the invention can be operably configured to monitor certain variables. One such variable can include monitoring the temperature of the electrodes and/or surrounding tissue in real time during treatment to ensure limited to no thermal damage to the tissue being treated. If monitored in real time, adjustments could then be made, if necessary, to avoid damage.

One, multiple, or all phases of system embodiments according to the invention can be performed manually or be performed (in whole or in any number of parts) by an automated system capable of performing the phases for the practitioner. Many of these steps can be performed without user input, and could be blocked off into distinct automated processes (with/without coupling to human-performed processes) or could be linked together through a comprehensive system. All of this is able to be done for an initial treatment, or redone for any retreatments that may be necessary, with or without new images (depending on case circumstances).

Example II

Comprehensive Package System: Treatment Planning Software.

Due to the great complexity and time required to develop customized treatment protocols for each patient, it is desirable to automate one or more steps, or the entirety, of the treatment planning process. Since Cassini Oval and other analytical solutions are limited by their ability to incorporate many of the complexities commonly found in treatment situations (such as heterogeneities, complex geometries, different electrode dimensions and orientations, etc.), and because the trend seems to be to move treatment planning towards a simpler solution for practitioners so less time is wasted in trying all the different available options—a robust automatic treatment planning system that incorporates numerous variables and runs a self-optimization algorithm to automatically determine the optimal treatment parameters needed to be used to treat a particular patient is highly desired.

Systems according to embodiments of the invention are flexible in that such systems can be operably configured to solve many scenarios numerically and to select the best electrode geometry and pulse parameters for a given situation. Alternatively or additionally, solutions may be obtained analytically, with tables, etc.

Embodiments of the systems according to the invention can be operably configured to be run on an independent system well in advance of treatment administration to allow sufficient computation time, review, and possible re-working of the protocol prior to treatment. The appropriate protocol could then be uploaded directly to the pulse generator.

Model Creation.

Preferred embodiments of systems according to the invention include a model creation stage for establishing an initial model of the target area.

Geometry:

Treatment geometries (information, such as tumor dimensions, electrodes, and peripheral tissue dimensions, for example) may be input manually, by analyzing medical images that were taken and any reconstructions, from computer analyses of medical images/tomography, or other (2D and 3D) mapping techniques.

Properties:

Conductivity values for the model subdomains may be obtained by measuring them on the subject directly (placing electrodes within tissue then applying a voltage and measuring the current to get $Z/\sigma$), by taking typical values found in the literature for the tissue types, or by noninvasive a measuring techniques such as functional Magnetic Resonance Imaging (fMRI), Electrical Impedance Tomography, etc; and combining these with the relevant equations (for E-field distributions, it is the ratio between tissues/regions that alters the field, absolute values will only be important when considering thermal effects). Medical images that already obtain the conductivity values (fMRI) or coupled to conductivity values (analyzing and mapping a medical image for the different tissues and coupling the regions to a conductivity value determined as described above) may then be used as the geometries for a numerical/analytical model as the various subdomains, to establish the initial model.

Electrodes.

Once the model geometry has been developed, a single or any set of electrode options (type, number, dimensions, etc.) may be selected to be used or allowed to be selected by the program.

Running the Program.

After setting up the geometry and electrode options to consider, the practitioner would essentially select a "GO" button to let the program run through the many variations to use and solve each using FEM or advanced analytical methods. The program would solve each scenario for various effects (no effect, reversible electroporation, irreversible electroporation, or thermal) and distributions within the model. Thermal considerations will greatly increase the computational cost of the model, but may be desired to determine thermal damage and scarring, especially in very sensitive structures.

Exemplary Optimization Quality Function.

The systems of embodiments of the invention can employ a variety of algorithms (iterative, genetic, etc.) in order to optimize the treatment parameters for the best possible result for a particular patient scenario. Such systems can also be operably configured to employ a function for evaluating the quality of each solution, where desired results, D, (IRE and/or REB throughout the targeted regions) are added; and the undesired results, U, (thermal damage, IRE beyond targeted region, etc.) are subtracted, with each aspect having its own unique scaling (since IRE to entire targeted region is far more important that avoiding IRE to healthy tissues). One such function can include:

$$\psi(ET, EP, \varphi, \ldots) = A \cdot [IRE]_D + B \cdot [REB]_D - C \cdot [Therm]_D - E \cdot [IRE]_U - F \cdot [REB]_U - G \cdot [Therm]_U \quad \text{Formula I:}$$

wherein D=Desired/Targeted Volume (done as a percentage);

U=Undesired/Peripheral Volume (done as an absolute value);

A, B, C, E, F, G=Scaling factors, with likely situations including: 1) A & B>>C, E, F, and G (treatment success most important); 2) G>>C (thermal to healthy worse than to targeted; 3) B & F may be neglected in purely IRE treatments; and 4) F can typically be assumed to be=0 since no negative effects to the tissue would be associated with this parameter, since it would either have no effect (without chemicals), or will not have an effect on healthy cells (with selective chemicals); but may matter in situations involving nonselective chemicals;

ET=Electrode Type and geometry (single/dual, diameter, length);

EP=Electrode Positioning (location and orientation in 3D space);

φ=Applied voltage;

ψ=Quality, the value of the protocol on the entire domain of the targeted and surrounding volumes.

Additional details on ψ(ET, EP, φ, . . . ): This is the value function of a given treatment protocol for the modeled domain previously mentioned as a function of electrode type and geometry, electrode positioning, applied voltage, and any other factors. More specifically: 1) ET (style, number, dimensions), with style referring to the style of the pulse, such as single, multi-unipolar, hybrid, proprietary, etc., with number referring to the number of probes used, and dimensions referring to the geometry and dimensions of all exposed and insulated regions in all three directions for each electrode used.

EP refers to the position of each or all electrodes in relation to a reference point arbitrarily chosen within the (x, y, z) domain of the model (location and orientation). In one example, the center of the tumor could be selected as the reference point and arbitrarily set to (0, 0, 0). The reference point may also be selected ahead of time or afterwards by the practitioner that will be easy for the practitioner to physically use at the time of treatment administration, such as some anatomical landmark that can be used as a reference for where the electrodes are and the electrode orientation. It is also possible to match the coordinate system from the medical images.

The ψ function may be solved for altered ET and EP, and the φ may then be scaled accordingly for the geometry (since it the model geometry and properties that will affect the shape of the distribution, the absolute value of it may be scaled to the applied voltage after this shape is found for each ET and EP). This would dramatically reduce the number of iterations and thus the computational cost.

In embodiments, the system can be operably configured to iteratively adjust ET, EP, etc. and obtain the resulting ψ, storing the top ones (or all those meeting some type of baseline threshold criterion). The resulting stored solutions would then be saved for presentation to the practitioner for conducting a review and visually assessing the value of each solution for selecting the protocol that best meets the demands of the therapy (could range on their arbitrary criterion such as the best quality, most simple to administer and apply the EP in the treatment, most robust, etc.)

The electrical parameters used (number of pulses, repetition rate, shape, pulse length, etc.) can be set as standardized parameters for typical treatments, and optionally these parameters can be flexible in case certain scenarios require different values—such as abdomino-thoracic procedures requiring repetition rate to be synchronized with the patient's heart rate to reduce the risk of pulse-induced arrhythmias. If known or found experimentally, standard electrical parameters can be used to determine the best combination of treatment parameters to use and have been applied to various tissues/tumors to determine the electric field threshold of each for this set of parameters, thus allowing treatment outcome to be reviewed and not just electric field distributions. Table II provides a list of exemplary electric parameters that can be manipulated within the IRE treatments discussed herein.

TABLE II

| Parameters | |
|---|---|
| Pulse length: | ns-ms range |
| Number of pulses: | 1-50,000 pulses |
| Electric Field Distribution: | 1-5,000 V/cm |
| Frequency of Pulse Application: | 0.001-1000 Hz |
| Frequency of pulse signal: | 0-100 MHz |
| Pulse shape: | square, triangular, trapezoidal, exponential decay, sawtooth, sinusoidal, alternating polarity |
| Pulse type: | Positive, negative, neutral electrode charge pulses (changing polarity within pulse) Multiple sets of pulse parameters for a single treatment (changing any of the above parameters within the same treatment to specialize outcome) |
| Electrode type: | Parallel plate: 0.1 mm-70 cm diameter (and larger for applications relating to e.g., whole organ decellularization) Needle electrode(s): 0.001 mm-1 cm diameter Single probe with embedded disk electrodes: 0.001 mm-1 cm diameter Spherical electrodes: 0.0001 mm-1 cm diameter Needle diameter: 0. 001 mm-1 cm Electrode length (needle): 0.1 mm to 30 cm Electrode separation: 0.1 mm to 5 cm, or even 5 cm to 20 cm, or 20 cm to 100 cm, and larger (for reversible electroporation, gene delivery, or positive electrode with ground patch on patient's exterior, e.g.) |

Additional considerations, such as multiple pulse protocols that create dynamic tissue properties as a function of electric field, and temperature changes, may need to be investigated or added. Such dynamic properties are demonstrated in FIGS. 13-19.

Figure 13A:
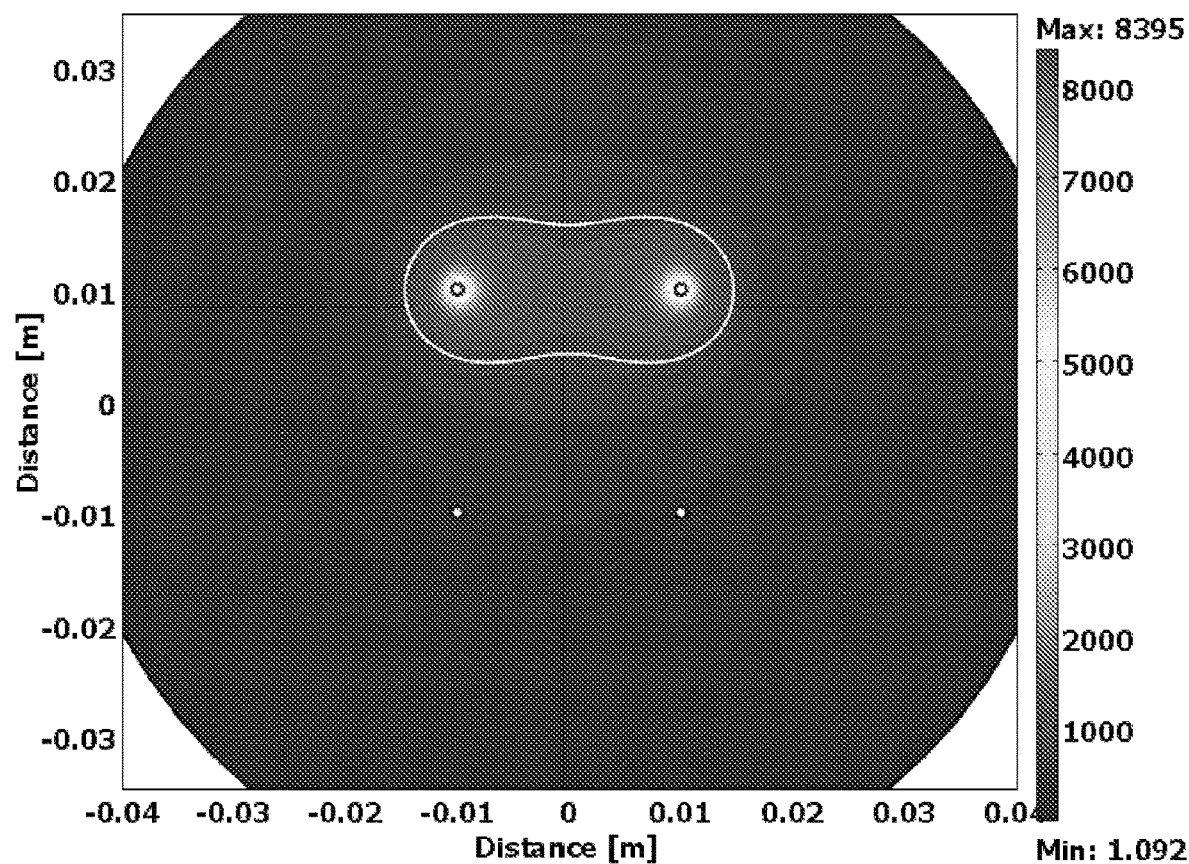
FIGS. 13A-B are respectively schematic diagrams of an electric field distribution and a corresponding conductivity map demonstrating a homogeneous distribution that only changes by 0.1% for visualization purposes when irreversible electroporation is accomplished.
Figure 13B:
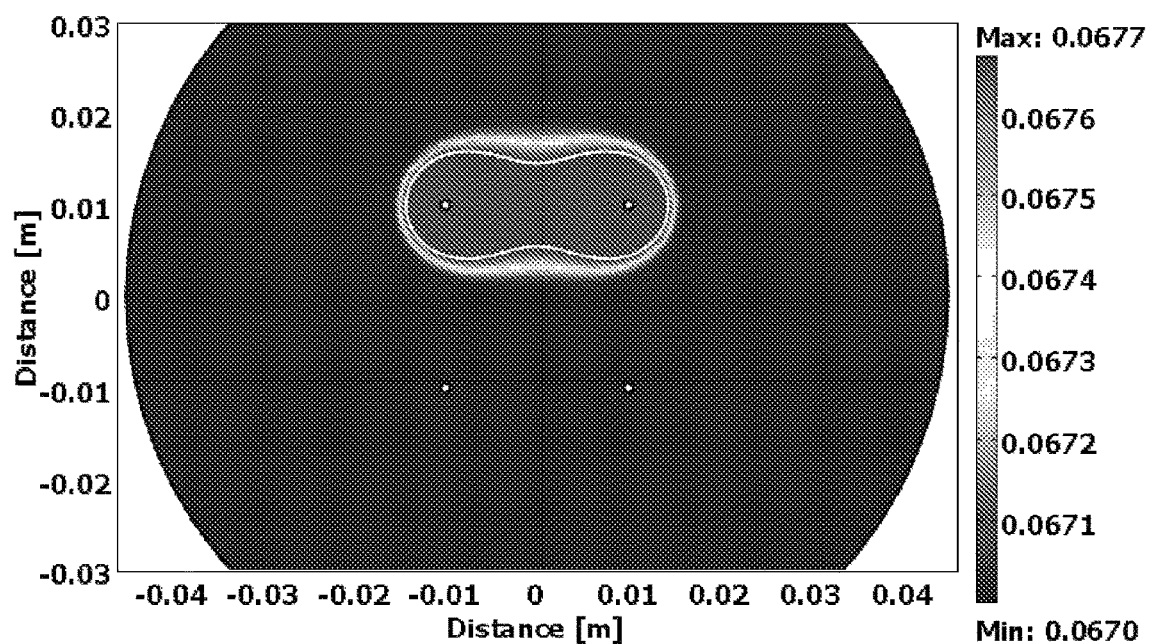

FIGS. 13A-B demonstrate a situation in which there would be little to no change in the physical properties of the tissue as a result of electroporation. More specifically, as shown in FIG. 13A, an electric field distribution [V/cm] generated by an applied voltage difference of 3000V over the upper two electrodes is shown. FIG. 13B provides a conductivity map [S/m] displaying a homogeneous distribution that only changes by 0.1% for visualization purposes when irreversible electroporation is accomplished. The white outline represents the region of tissue that is exposed to an electric field magnitude that is sufficient for generating irreversible electroporation.

Figure 14A:
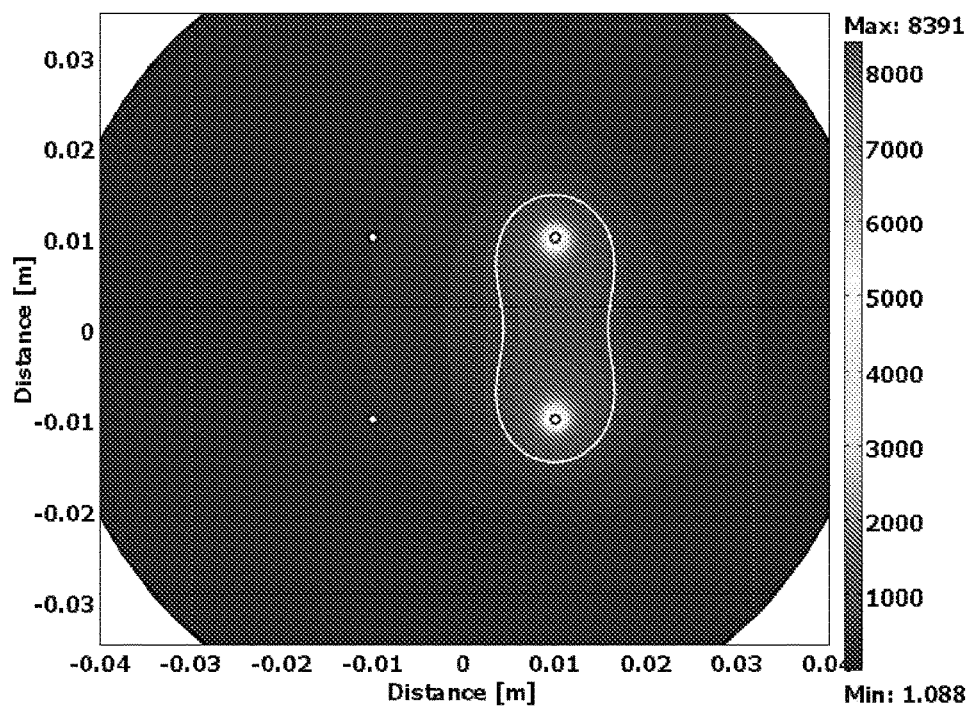
FIGS. 14A-B are respectively schematic diagrams of an electric field distribution and a corresponding cumulative conductivity map demonstrating a treatment region where more than two electrode pairs are energized and homogeneous distribution only changes by 0.1% for visualization purposes when irreversible electroporation is accomplished.
Figure 14B:
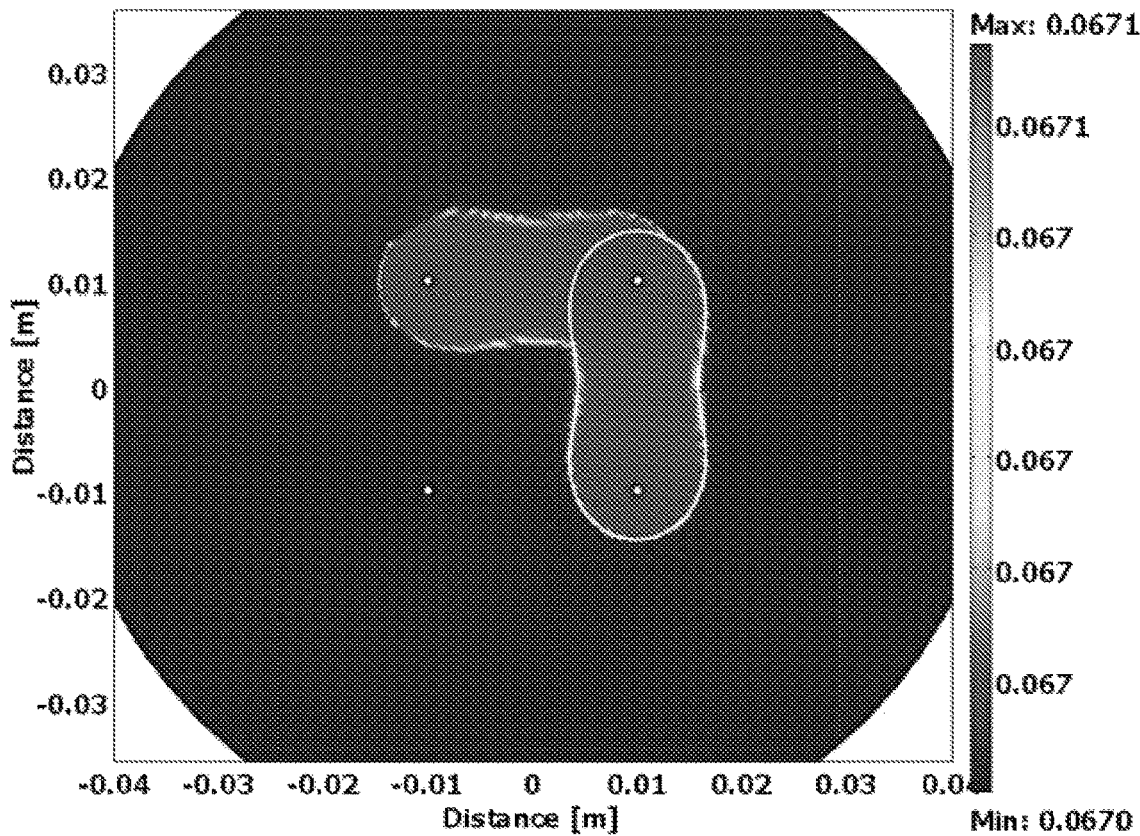

FIGS. 14A-B demonstrate an electric field distribution and conductivity map for a treatment region for a given situation in which more than two electrode pairs are energized. In FIG. 14A, an electric field distribution [V/cm] generated by an applied voltage difference of 3000V over the right two electrodes is shown. FIG. 14B shows a conductivity map [S/m] displaying a homogeneous distribution that only changes by 0.1% for visualization purposes when irreversible electroporation is accomplished in this set up. In FIG. 14B, a cumulative visualization of the treatment region is shown.

Figure 15A:
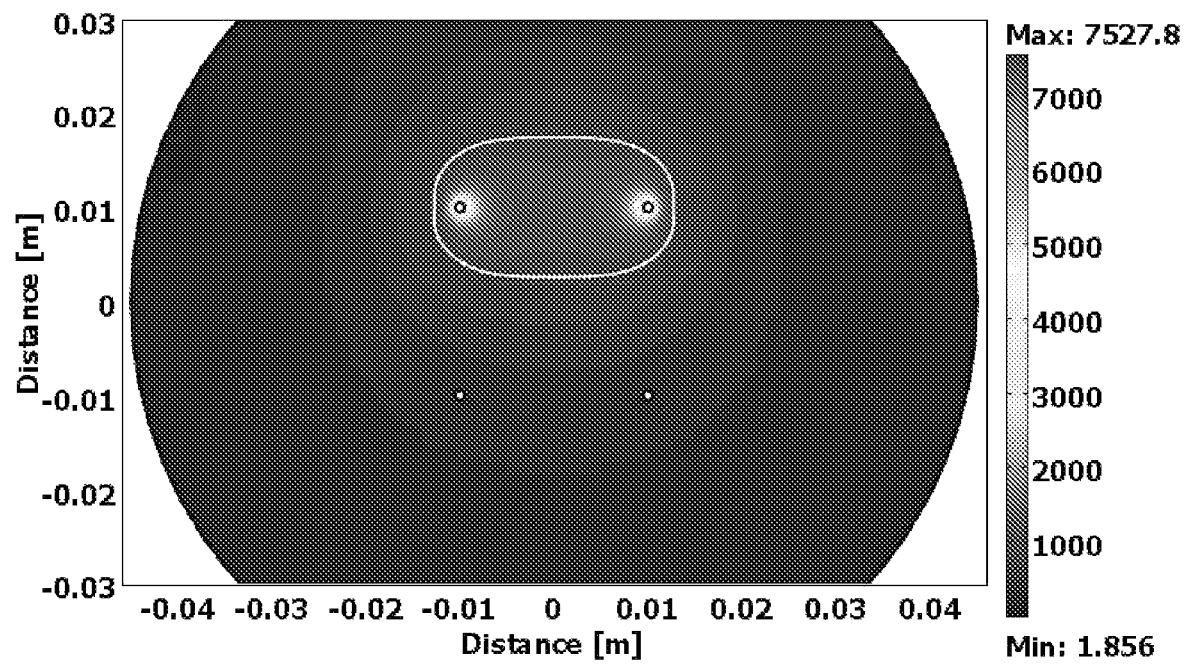
FIGS. 15A-B are respectively schematic diagrams of an electric field distribution and a corresponding conductivity map demonstrating a heterogeneous distribution that changes from 0.67 S/m to 0.241 due to electropermeabilization caused by electroporation.
Figure 15B:
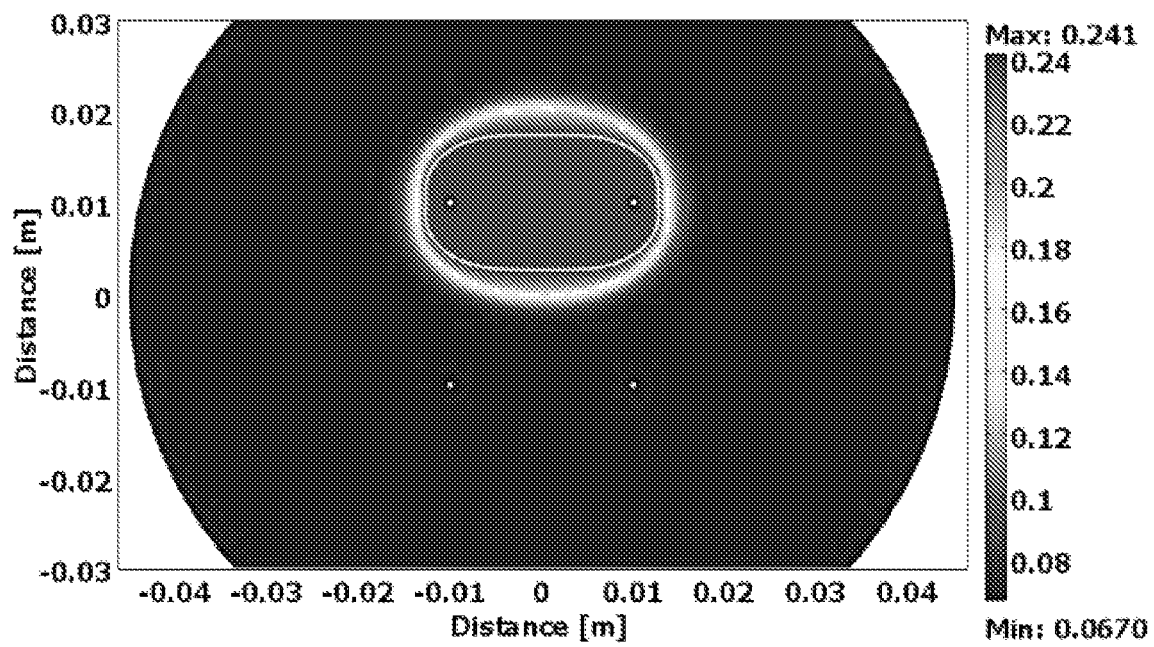

FIGS. 15A-B demonstrate a change in the shape and size of the treatment region due to electropermeabilization. More particularly, in FIG. 15A, an electric field distribution [V/cm] generated by an applied voltage difference of 3000V over the upper two electrodes is shown. FIG. 15B provides a conductivity map [S/m] displaying a heterogeneous distribution that changes from 0.67 S/m to 0.241 due to electropermeabilization as a result of electroporation. Of particular note in this example, the shape and size of the treatment region is consequently adjusted as a result of this change. In FIG. 15B the shape and size of the planned treatment region is different than in the above examples (FIGS. 13B and 14B) in which the conductivity was assumed to remain constant throughout the delivery of the pulses.

Figure 16A:
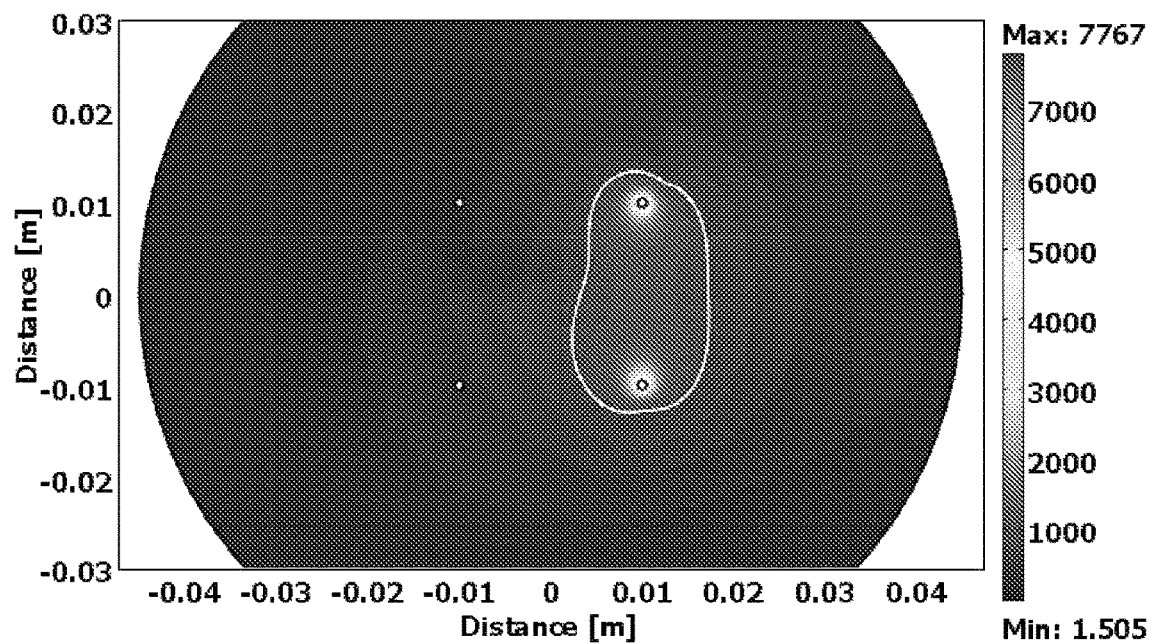
FIGS. 16A-B are respectively schematic diagrams of an electric field distribution and a corresponding conductivity map demonstrating a heterogeneous distribution that changes from 0.67 S/m to 0.241 S/m due to electropermeabilization.
Figure 16B:
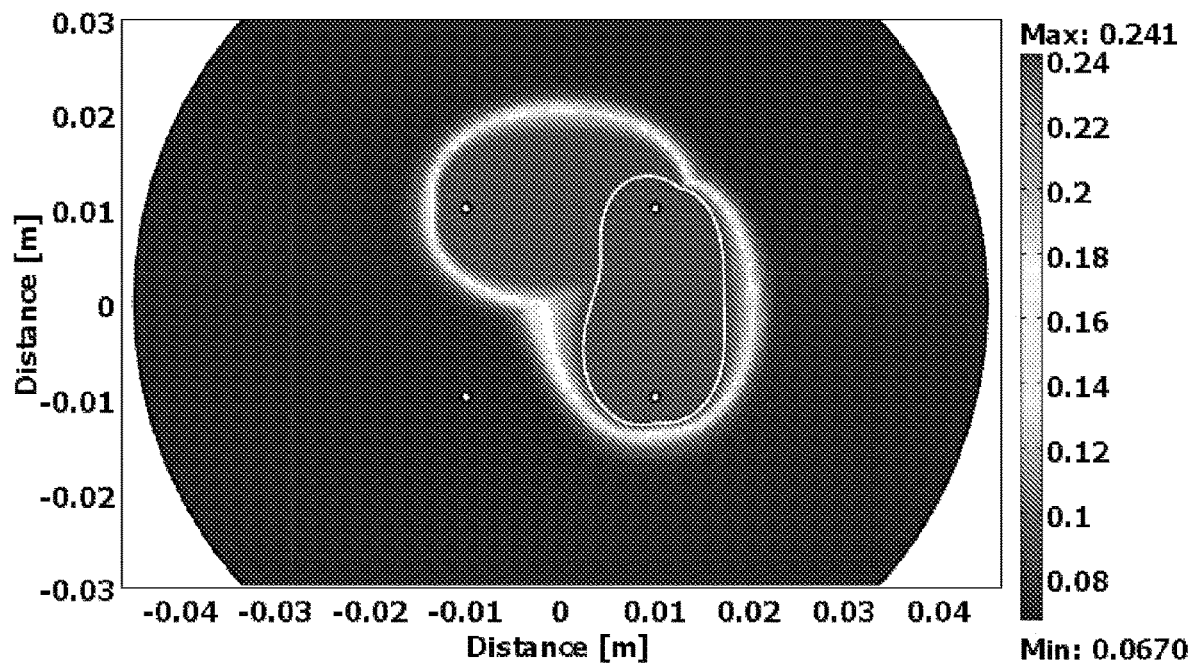

FIG. 16A provides an electric field distribution [V/cm] generated by an applied voltage difference of 3000V over the right two electrodes, while FIG. 16B shows a conductivity map [S/m] displaying a heterogeneous distribution that changes from 0.67 S/m to 0.241 S/m due to electropermeabilization. Of particular interest, the first set of pulses using the top two electrodes increased the conductivity of the tissue which in turn modified the electric field distribution (i.e., treatment region) for the second application of pulses (right two electrodes) adjacent to the permeabilized region.

The following examples are different than the previously described examples in which the treatment region depended on electropermeabilization, and multiple electrode combinations. In this case, a 2-D model of an irreversible electroporation protocol is shown in which the electric parameters of the protocol included 90 pulses, at 2000V, delivered at a frequency of 1.5 Hz, using 100 μs pulses. The 2D model generates much higher temperatures and thus changes relative to the complete 3D model since the heat has a larger volume in which to diffuse. Nevertheless, this case is reported for illustration purposes and to show that in fact these dynamic effects can be incorporated into treatment planning models. Changes only due to temperature are incorporated in this example to emphasize the importance of accounting for these effects in the models.

Figure 17A:
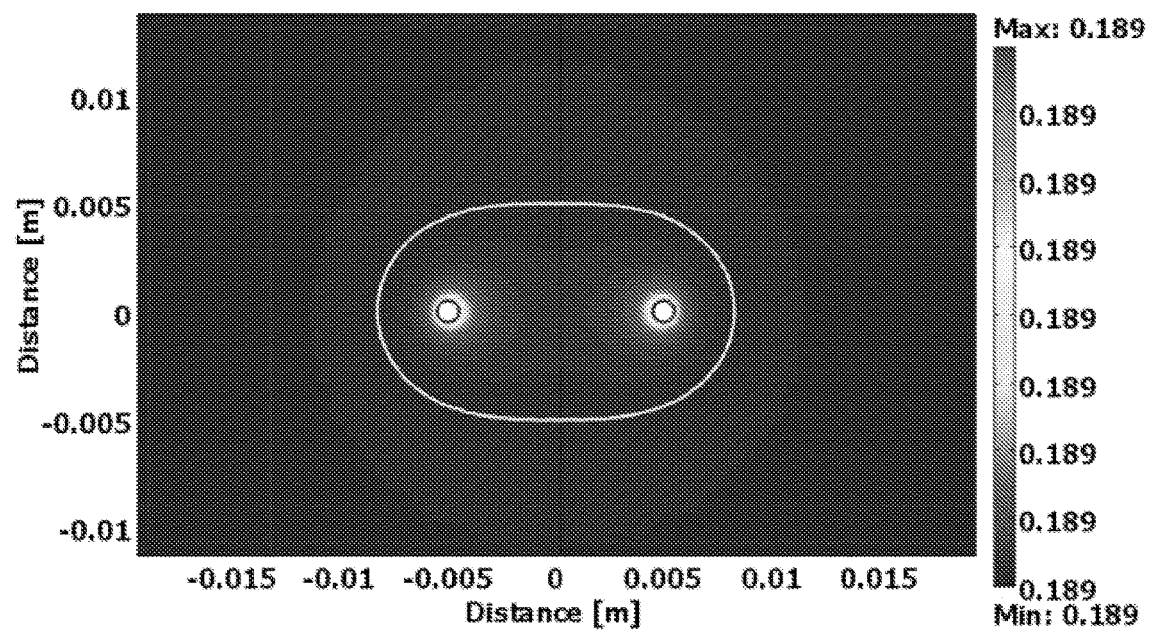
FIGS. 17A-B are respectively schematic diagrams of an electric conductivity map and corresponding potential thermal damage resulting from electroporation at t=0 s.
Figure 17B:
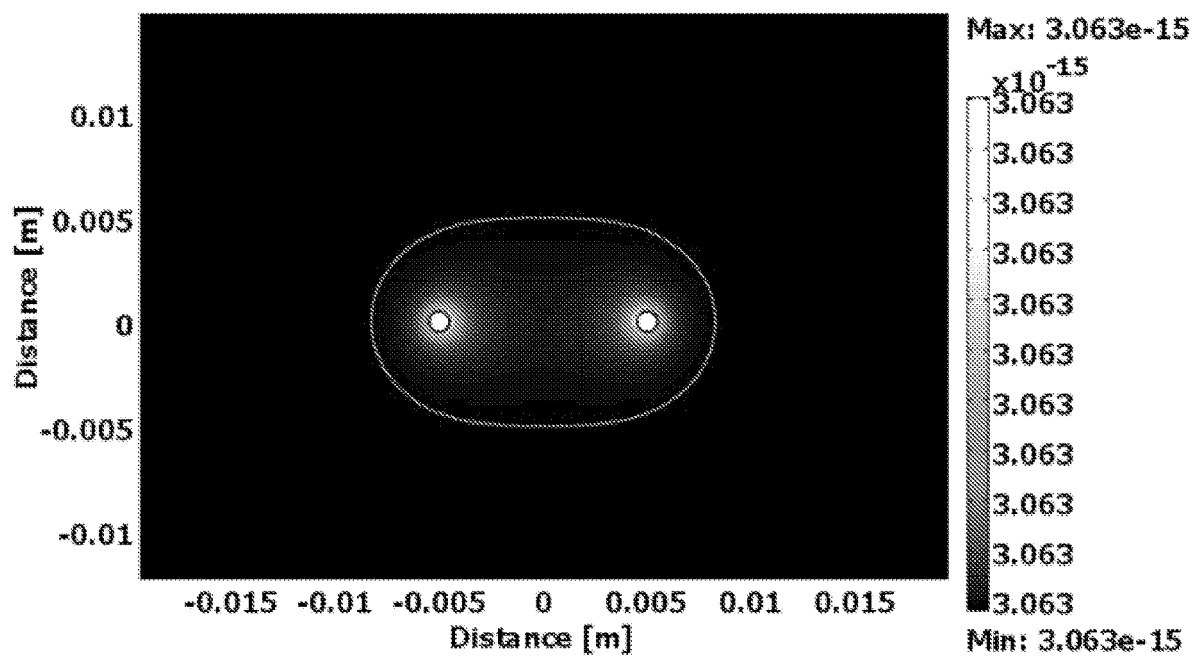

To illustrate the thermal effect of electroporation on tissues contacting the electrodes, FIGS. 17-19 are provided. FIG. 17A provides an electric conductivity [S/m] map at t=0 s in which the irreversible electroporation area is 2.02 cm$^2$. FIG. 17B shows a thermal damage assessment by the potential increase in temperature due to the electric pulses which occurs when greater than 0.53.

Figure 18A:
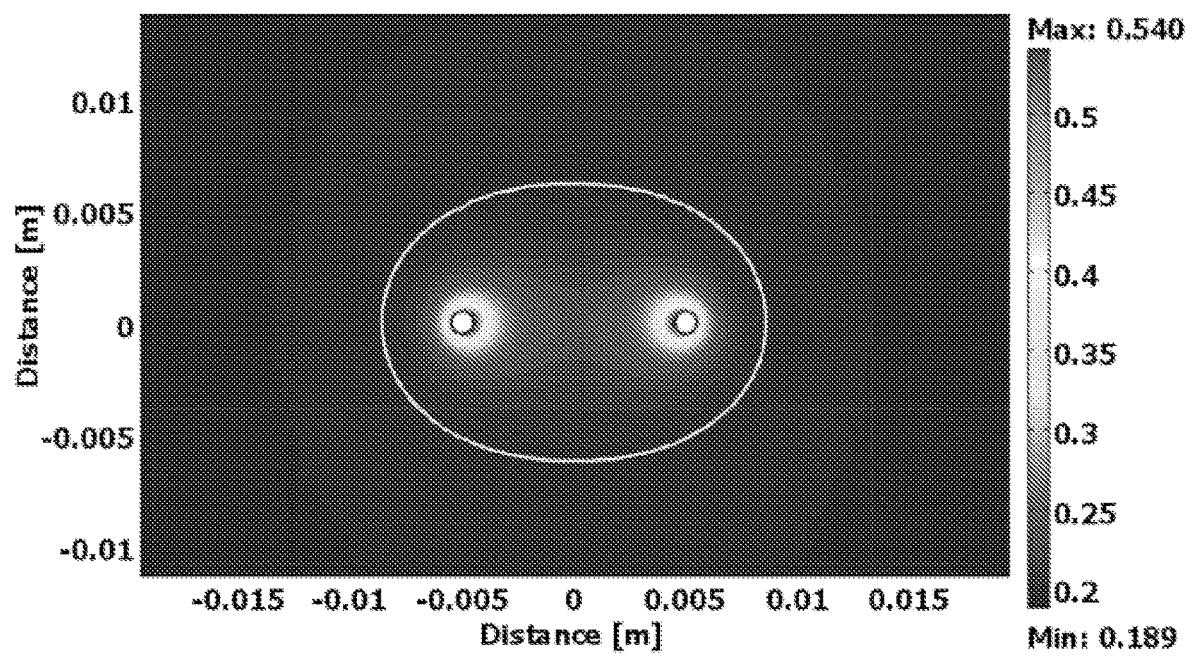
FIGS. 18A-B are respectively schematic diagrams of an electric conductivity map and corresponding potential thermal damage resulting from the electroporation at t=30 s.
Figure 18B:
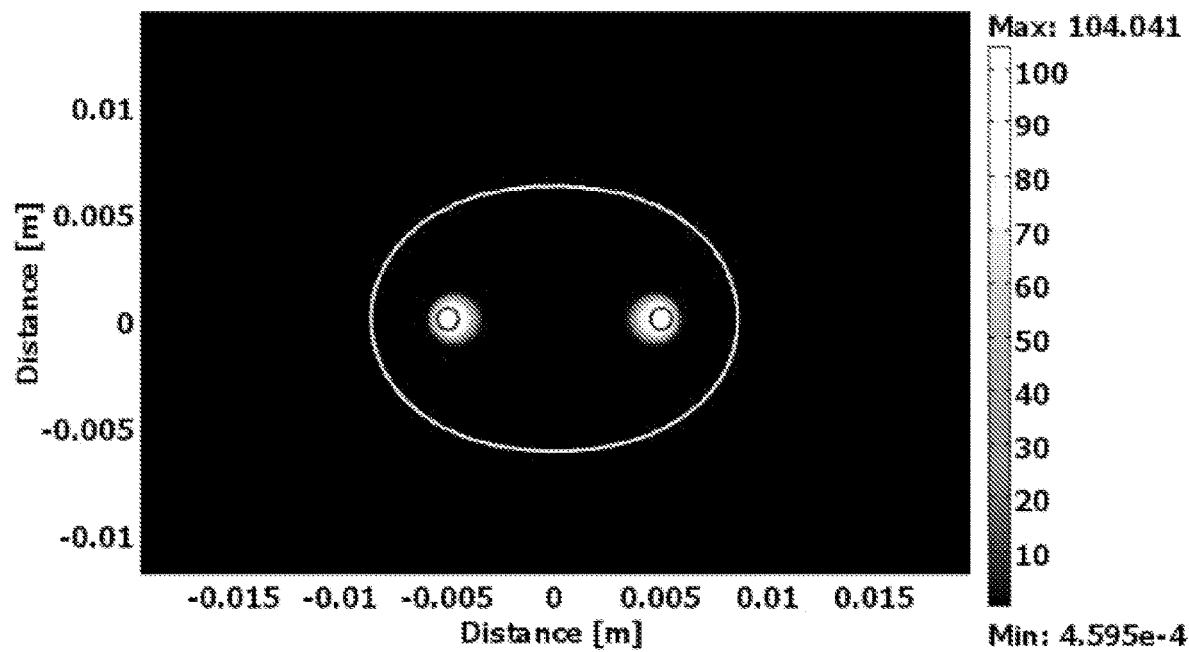

FIG. 18A provides an electric conductivity [S/m] map at t=30 s in which the irreversible electroporation region is 2.43 cm$^2$. FIG. 18B shows some thermal damage visualized at the electrode-tissue interface 0.11 cm$^2$.

Figure 19A:
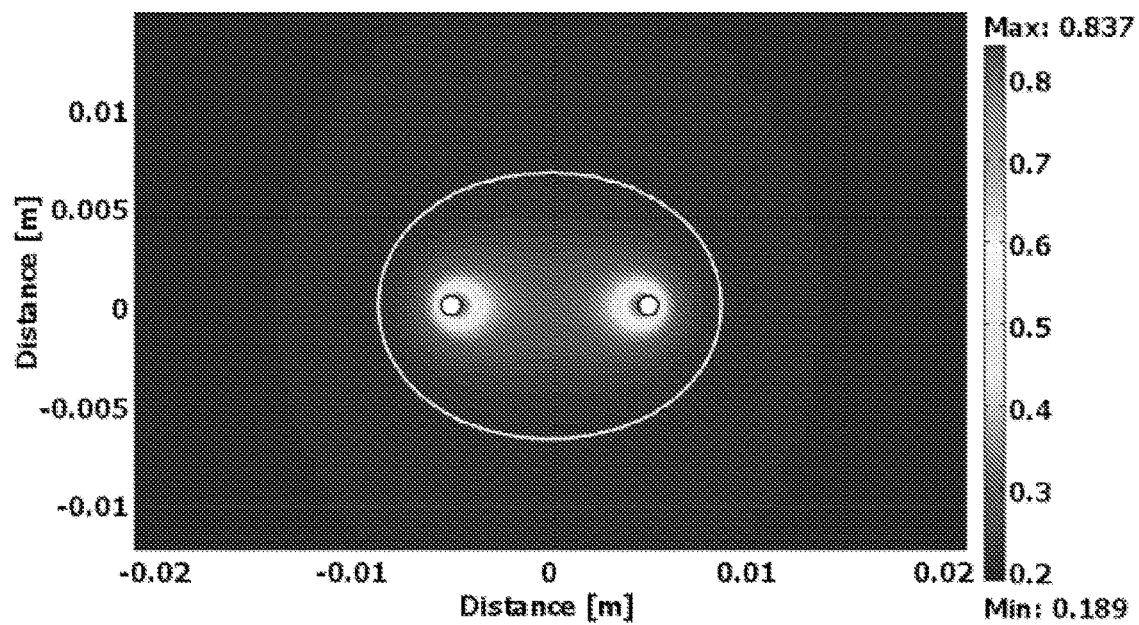
FIGS. 19A-B are respectively schematic diagrams of an electric conductivity map and corresponding potential thermal damage resulting from the electroporation at t=60 s.
Figure 19B:
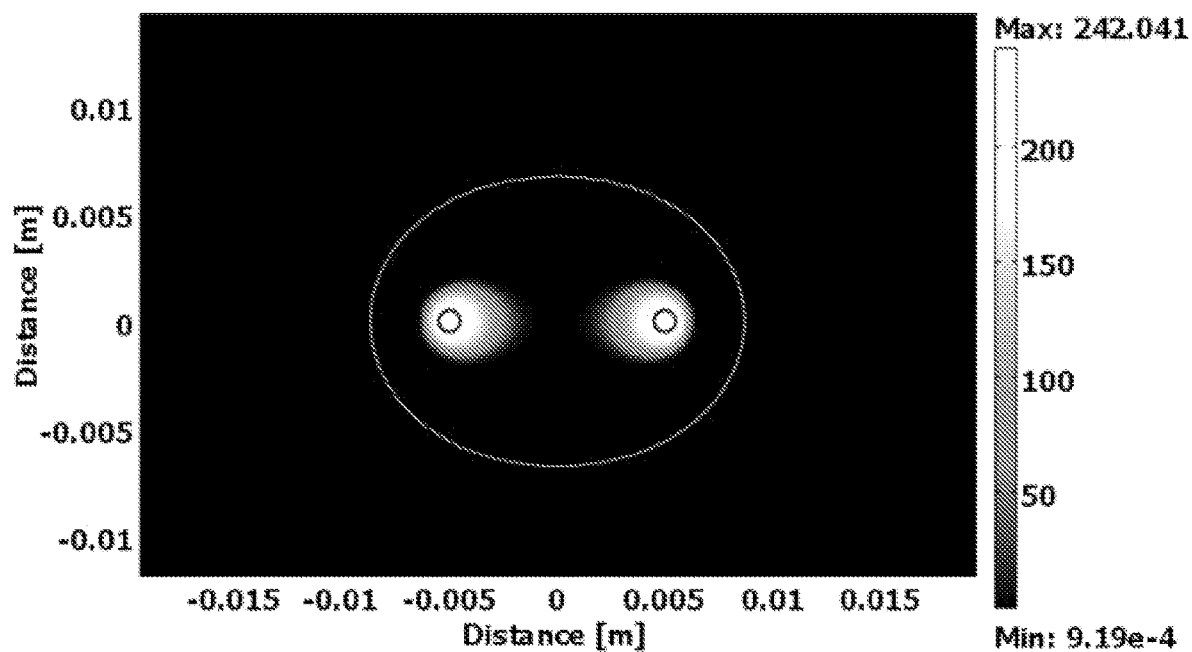

FIG. 19A provides an electric conductivity [S/m] map at t=60 s in which the irreversible electroporation area is 2.63 cm$^2$. FIG. 19B shows significant thermal damage at the electrode-tissue interface due to thermal effects 0.43 cm$^2$.

Therapy Application.

Once the practitioner has selected a desired solution from the options on the treatment planning software, the electrical protocol (pulse characteristics, number, sequence, etc.) could be saved and then uploaded to the pulse generator system. At this point, the practitioner would have to do no more than place the electrodes in the predetermined positions and hit "START", at which point the instrument carries out the prescribed pulsing conditions.

Example III

Exemplary Methods for IRE Treatment Planning.

Figure 20A:
FIGS. 20A-B are two-dimensional (2-D) diagnostic T1 post-contrast MRI scans in which the tumor was traced.
Figure 20B:

Open source image analysis software (OsiriX, Geneva, Switzerland) was used to isolate the brain tumor geometry from the normal brain tissue. The tumor was traced in each of the two-dimensional (2-D) diagnostic T1 post-contrast MRI scans as shown in FIGS. 20A-B. Attempts were made to exclude regions of peritumoral edema from the tumor volume by composite modeling of the tumor geometry using all available MRI sequences (T1 pre- and post-contrast, T2, and FLAIR) and image planes.

As provided in FIGS. 21A-H, a three-dimensional (3-D) solid representation of the tumor volume was generated using previously reported reconstruction procedures. The tumor geometry was then imported into a numerical modeling software (Comsol Multiphysics, v.3.5a, Stockholm, Sweden) in order to simulate the physical effects of the electric pulses in the tumor and surrounding healthy brain tissue. The electric field distribution was determined in which the tissue conductivity incorporates the dynamic changes that occur during electroporation. In this model, a 50% increase in conductivity was assumed when the tissue was exposed to an electric field magnitude greater than 500 V/cm, which has been shown as an IRE threshold for brain tissue using specific experimental conditions. Currently, the threshold for brain tumor tissue is unknown so the same magnitude as normal tissue was used for treatment planning purposes.

Based on the tumor dimensions and numerical simulations, the voltage configurations that would mainly affect tumor tissue were determined and are provided in Table III as well as are displayed in FIGS. 21A-H.

TABLE III

| VOLTAGE (V) | ELECTRODE GAP (CM) | ELECTRODE EXPOSURE (CM) | VOLT-TO-DIST RATIO (V/CM) | PULSE DURATION | NUMBER OF PULSES | FREQUENCY |
|---|---|---|---|---|---|---|
| 500 | 0.5 | 0.5 | 1000 | 50 μs | 2 × 20 | ECG synchronized |
| 625 | 0.5 | 0.5 | 1250 | 50 μs | 4 × 20 | ECG synchronized |

IRE Therapy.

Total intravenous general anesthesia was induced and maintained with propofol and fentanyl constant rate infusions. A routine left rostrotentorial approach to the canine skull was performed and a limited left parietal craniectomy defect was created. The craniectomy size was limited to the minimum area necessary to accommodate placement of the IRE electrode configurations required to treat the tumor, as determined from pre-operative treatment plans. Following regional durectomy, multiple biopsies of the mass lesion were obtained, which were consistent with a high-grade (WHO Grade III) mixed glioma.

After administration of appropriate neuromuscular blockade and based on the treatment planning, focal ablative IRE lesions were created in the tumor using the NanoKnife® (AngioDynamics, Queensbury, N.Y. USA), and blunt tip electrodes. The NanoKnife® is an electric pulse generator in which the desired IRE pulse parameters (voltage, pulse duration, number of pulses, and pulse frequency) are entered. The NanoKnife® is also designed to monitor the resulting current from the treatment and to automatically suspend the delivery of the pulses if a current threshold is exceeded.

The electrodes were inserted into the tumor tissue in preparation for pulse delivery. The blunt tip electrodes were connected by way of a 6-foot insulated wire (cable) to the generator. After foot pedal activation, the pulses were conducted from the generator to the exposed electrodes.

The two sets of pulse strengths were delivered in perpendicular directions to ensure uniform coverage of the tumor and were synchronized with the electrocardiogram (ECG) signal to prevent ventricular fibrillation or cardiac arrhythmias (Ivy Cardiac Trigger Monitor 3000, Branford, Conn., USA). The sets of pulses were delivered with alternating polarity between the sets to reduce charge build-up on the surface of the electrodes. In addition, shorter pulse durations than those used in previous IRE studies were used in order to reduce the charge delivered to the tissue and decrease resistive heating during the procedure. Previous calculations and experimental data from previous intracranial IRE experiments ensured that no thermal damage would be generated in normal brain. The temperature measured near the electrodes showed a maximum 0.5° C. increase after four sets of twenty 50-μs pulses when using similar parameters to the ones in Table I. In addition, the charge delivered during the procedure was typical or lower than that used in humans during electroconvulsive therapy, a treatment for depression that also uses electric pulses.

Example IV

Treatment Systems, Methods, and Devices Using Bipolar Electric Pulses.

It has been found that alternating polarity of adjacent electrodes minimizes charge build up and provides a more uniform treatment zone. More specifically, in IRE treatments there is an energized and grounded electrode as the pulses are delivered. In embodiments, charge build-up on the surface of the electrodes can be minimized by alternating the polarity between sets of pulses. It is believed that there are still electrode surface effects that can be associated with negative outcomes.

Figure 22:
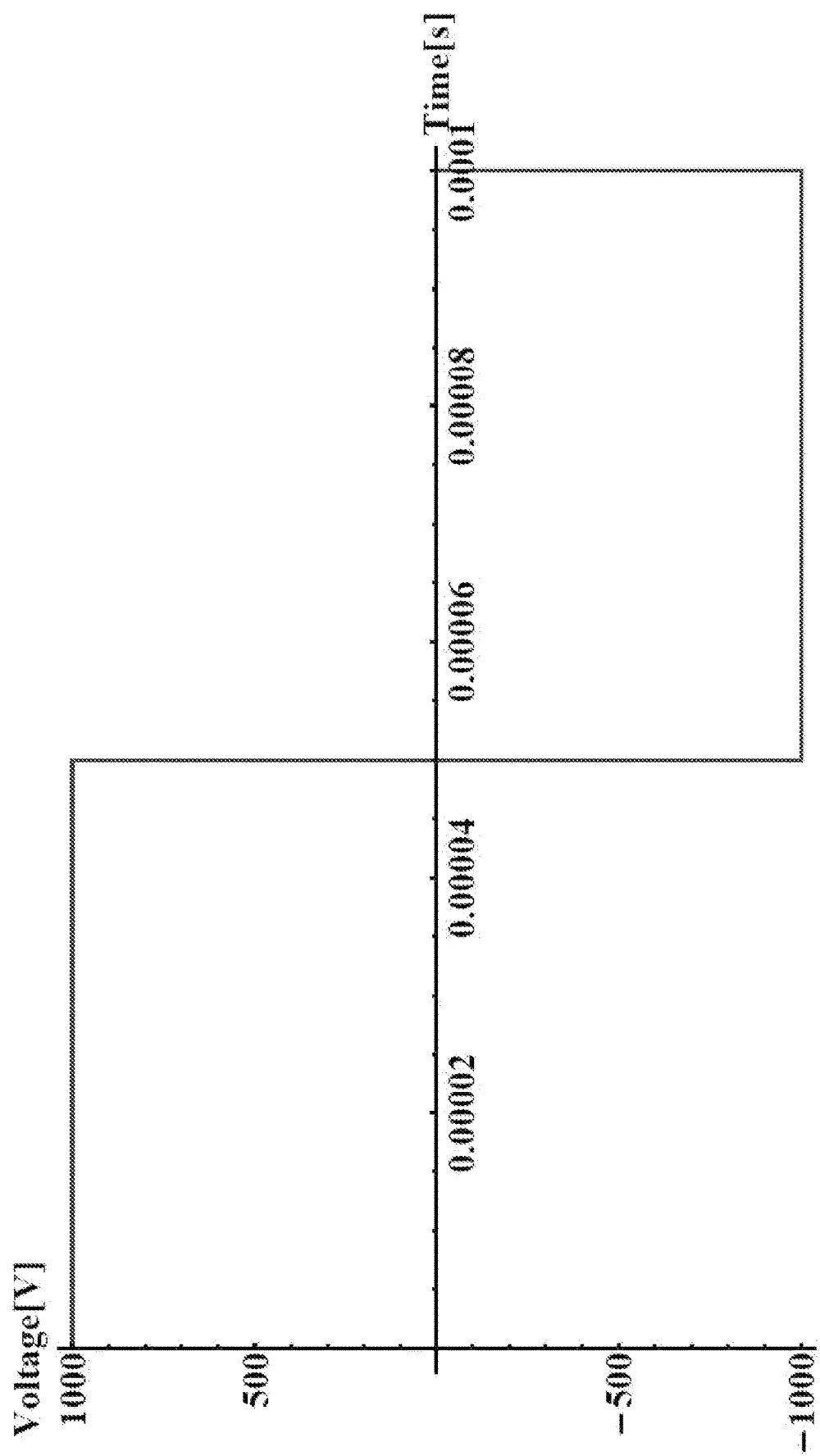
FIG. 22 is a graph showing a Bipolar IRE pulse (100 μs duration) with alternating polarity in the middle of the pulse.

Further, the use of bipolar pulses (net charge of zero) as seen in FIG. 22 is a way to further minimize the charge delivered to the tissue. FIG. 22 is a graph showing a Bipolar IRE pulse (100 μs duration) with alternating polarity in the middle of the pulse in order to minimize charge delivered to the tissue. In this manner, negative effects can be prevented, reduced, or avoided as part of IRE treatment in the brain, including deleterious electrochemical effects and/or excessive charge delivered to the tissue as in electroconvulsive therapy.

In one experiment, a superficial focal ablative IRE lesion was created in the cranial aspect of the temporal lobe (ectosylvian gyrus) using the NanoKnifeB (AngioDynamics, Queensbury, N.Y.) generator, blunt tip bipolar electrode (AngioDynamics, No. 204002XX) by delivering 9 sets of ten 50 μs pulses (voltage-to-distance ratio 2000 V/cm) with alternating polarity between the sets to prevent charge build-up on the stainless steel electrode surfaces. These parameters were determined from ex-vivo experiments on canine brain and ensured that the charge delivered during the procedure was lower than the charge delivered to the human brain during electroconvulsive therapy (an FDA approved treatment for major depression).

Other undesirable consequences of various electroporation protocols have also been experienced. More specifically, with the application of electric potentials, electrical forces may drive ions towards one electrode or the other. This may also lead to undesirable behavior such as electrolysis, separating water into its hydrogen and oxygen components, and leading to the formation of bubbles at the electrode-tissue interface. These effects are further exacerbated for multiple pulse applications. Such effects may cause interference with treatment by skewing electric field distributions and altering treatment outcomes in a relatively unpredictable manner. By altering the polarity between the electrodes for each pulse, these effects can be significantly reduced, enhancing treatment predictability, and thus, outcome. This alternating polarity may be a change in potential direction for each pulse, or occur within each pulse itself (switch each electrode's polarity for every pulse or go immediately from positive to negative potential within the pulse at each electrode).

Figure 23A:
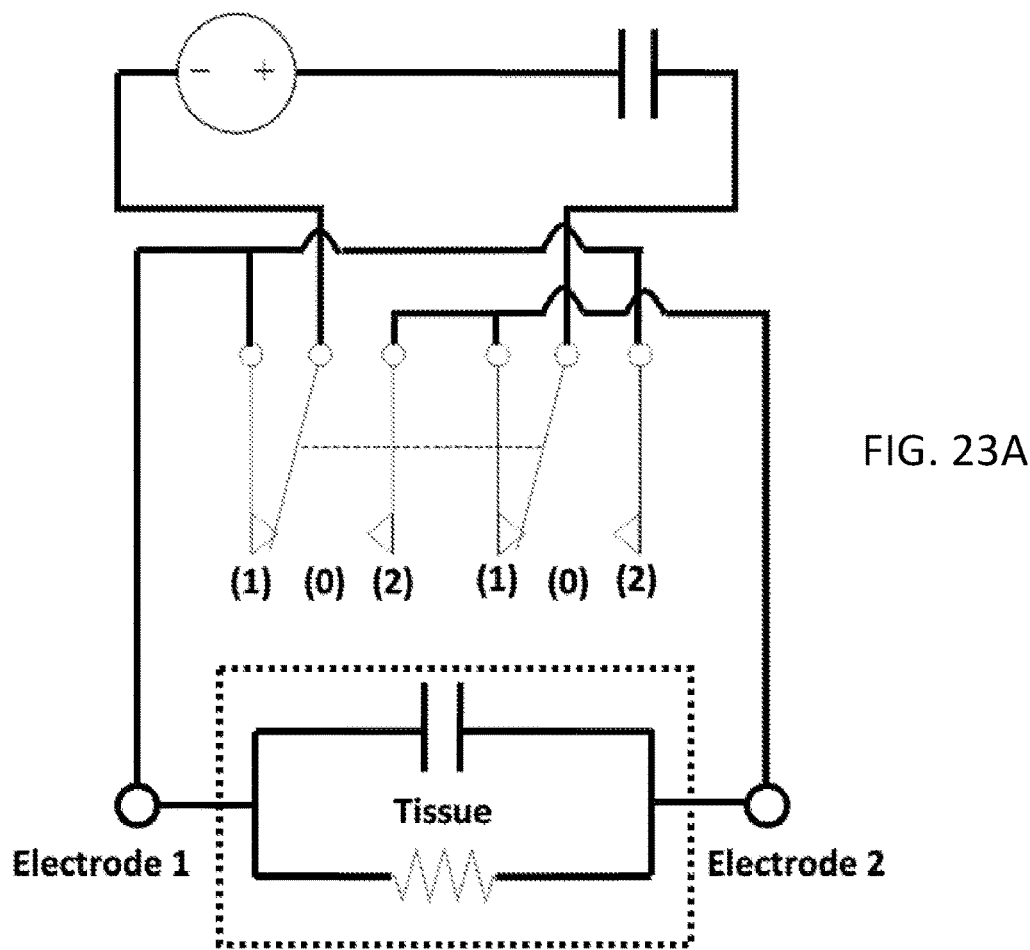
FIG. 23A is a schematic diagram of a representative circuit model for switching polarity between pulses and multipolar pulses.
Figure 23B:
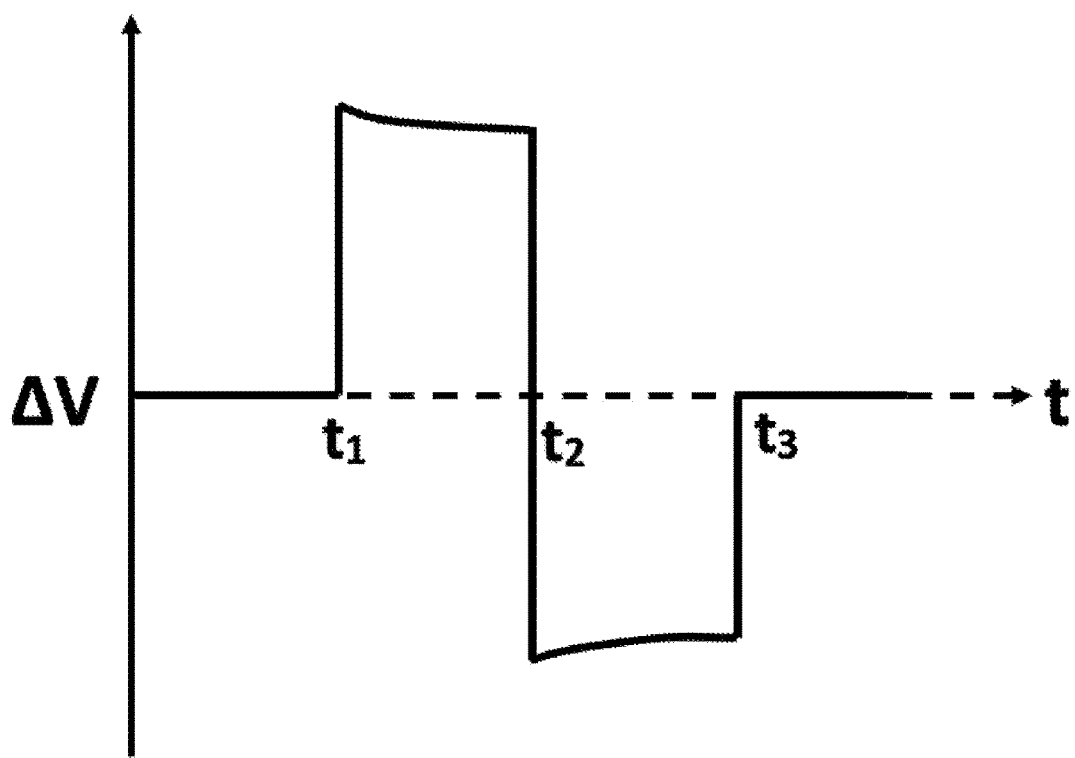
FIG. 23B is a graph showing the shape of a bipolar pulse that can be created using the electrical circuit of FIG. 23A.

FIG. 23A is a schematic diagram of a representative circuit model for switching polarity between pulses and multipolar pulses. As shown in FIG. 23A, a basic circuit according to embodiments of the invention may contain a) a generator supply circuit containing a voltage source and capacitor bank to accumulate sufficient charge for pulse delivery; b) a simultaneous switching mechanism; c) electrodes for pulse delivery (here, 2 electrodes are shown); and d) a parallel capacitor-resistor equivalent to represent the behavior of biological tissues. FIG. 23B shows an exemplary bipolar pulse that can be created using the circuit of FIG. 23A.

The circuit can be operably configured to function in the following representative manner. At Time 0, the switches are in position 0. The voltage source would be used to charge an array of capacitors to the desired electric potential for a given pulse. At Time $t_1$, the switches move to position 1. This causes rapid initiation of capacitor discharge, generating a high-slope ΔV between the electrodes placed in the tissue (the first half of a square wave). This gives electrode 1 a "negative" voltage and electrode 2 a "positive" voltage (based on their relative electric potentials). The capacitor(s) continue delivering the electric charge over time, causing a logarithmic decay of the electric potential to which the tissue is exposed. At Time $t_2$, the switches move to position 2. This changes which electrode is connected to which end of the circuit, rapidly reversing the polarity of the electric potential, making electrode 1 "positive" and electrode 2 "negative." The peak of this reversal is the same as the remaining charge on the capacitors after the decay between $t_1$ and $t_2$. The remaining charge on the capacitors continues to decay. At Time $t_3$, the switches return to position 0. This disconnects the circuits, creating a rapid drop in the electric potential between the electrodes, returning ΔV to zero. Alternatively, at Time $t_3$, the switch could return to position 1, then alternate between positions 1 and 2 for a desired period of time to deliver several bipolar pulses in rapid succession. Such switching circuitry would enable delivery of a bipolar pulse train comprising individual pulses having a duration ranging from 10 ms to 1 ns, much faster than any human could achieve.

It should be mentioned that the electric potential difference is arbitrary, and the polarity of any of the pulses in the above-mentioned example are for demonstration only, and are not the sole method of obtaining multipolar pulses. Alternative approaches are possible and this basic circuitry representation may be adapted to generate any series of complex pulses by changing the pattern of switch behavior.

For instance, unipolar pulses may have their polarity reversed every pulse or after any number of pulses by moving the switches from position 0 to 1 for pulse delivery, then back to 0 (first pulse); then from position 0 to 2 for delivery, then back to 0 (second pulse of opposite polarity). As shown in FIGS. 24A-D, a unipolar pulse of any polarity can be reversed after one or more pulses up to any number of desired pulses for a particular application. For example, a time delay between the unipolar pulse and the reversed polarity unipolar pulse can be any desired duration as well, including from 5 times the pulse length (FIG. 24A), to 3 times the pulse length (FIG. 24B), to 1 time the pulse length (FIG. 24C), to no delay (or effectively no delay) at the time of switching (FIG. 24D).

Further, it has been discovered that the number of electrical pulses that can be applied to successfully treat tumors can be quite high. Prior art methods of using IRE for various purposes included the use of relatively few pulses, for example 8 pulses or so. Reports of use of up to 80 pulses for IRE have been published; however, to the inventors' knowledge, a higher number of pulses has not been recommended. The present invention provides for the use of a relatively high number of pulses, on the order of 90 pulses or greater. For example, in exemplary embodiments, 90 pulses are used. Other embodiments include the use of more than 90 pulses, such as 100 pulses, 110 pulses, or more. Moderately high numbers of pulses, such as those in the range of 50-90 pulses can also be used according to the invention, as well as moderate numbers of pulses, such as those in the range of 20-50 pulses. It has also been determined that voltages traditionally used for IRE are too high for beneficial treatment of tumors in situ. For example, typically, IRE is performed using voltages of between 4000 V/cm to 1500 V/cm. The present invention provides for use of voltages of much lower power. For example, the present methods can be performed using less than 1500V/cm. Experiments performed by the inventors have shown that 2000 V/cm can cause excessive edema and stroke in patients when applied to brain tissue. Advantageously, for treatment of brain tumors, applied fields of about 500 V/cm to 1000 V/cm are used. Thus, in general for treatment of brain tumors, applied fields of less than 1000 V/cm can be used. Further, where a range is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

As shown in FIGS. 24E-G, the pattern of alternating between pulse polarities can be repeated any number of times to accomplish a desired result. For example, the bipolar pulse of FIG. 24D is shown repeated at timing intervals of 3 times the pulse length (FIG. 24E), to 2 times the pulse length (FIG. 24F), to 1 time the pulse length (FIG. 24G). The delay between bipolar pulses can also be zero (or effectively zero) and/or the bipolar pulses can be repeated any number of time to establish a particular desired pulsing protocol or pattern.

The pulses could also be made multipolar by switching from position 0 to 1 (first polarity), then to position 2 (reversed polarity), then back to position 1 (returning to initial polarity), and so on, all within the same pulse.

Even further, the bipolar pulses can be configured in a manner to deliver a charge to the tissue where the net effect of the pulse is something other than zero. For example, the magnitude of the positive portion of the pulse can be different than the magnitude of the negative portion of the pulse. More specifically, the pulse can be 90% positive and 10% negative or 90% negative and 10% positive. Indeed, any ratio of positive:negative charge can be used, including from 0:100 (mono-polar and positive) to 100:0 (mono-polar and negative). Specifically, 50:50 (net charge of zero) is preferred, but 90:10, 80:20, 75:25, 60:40 and the reverse can be used depending on the desired effect.

Additionally, the time between any switch could be used to alter the length of any pulse or change the pulse repetition rate. And, if varying combinations of different capacitor banks were used in the system, then depending on which ones were connected, it would be possible to change the applied voltage to the electrodes between pulses or within a pulse (of any polarity).

The shape and type of pulse can also be varied for particular applications. In various embodiments, the individual electric pulses can be unipolar while in other embodiments, the individual electric pulses can be bipolar. In certain preferred embodiments, a train of unipolar pulses is delivered in one direction, followed by a subsequent pulse train of opposite polarity. Depending on the outcome desired, the waveforms of the electric pulses are triangular, square, sinusoidal, exponential, or trapezoidal. Other geometric shapes are contemplated as well. In some embodiments, an electrode is connected to a system for employing electrical impedance tomography (EIT), computed tomography (CT), Magnetic Resonance Imaging (MRI), or ultrasound to image the tissue prior to treatment by applying small alternating currents that themselves do not damage the tissue.

A large variety of other parameters can influence the efficiency of membrane poration, such as the shape of the electrical pulses, polarity, size of target cells, and thermal conditions during and after the pulses.

Another method for avoiding excessive charge build up in tissues being treated by electroporation is to deliver counteracting pulses simultaneously from one or more pulse generator. In embodiments, the pulses delivered by the generators can overlap in time for some portion of the pulse and be offset from one another.

Figure 25A:
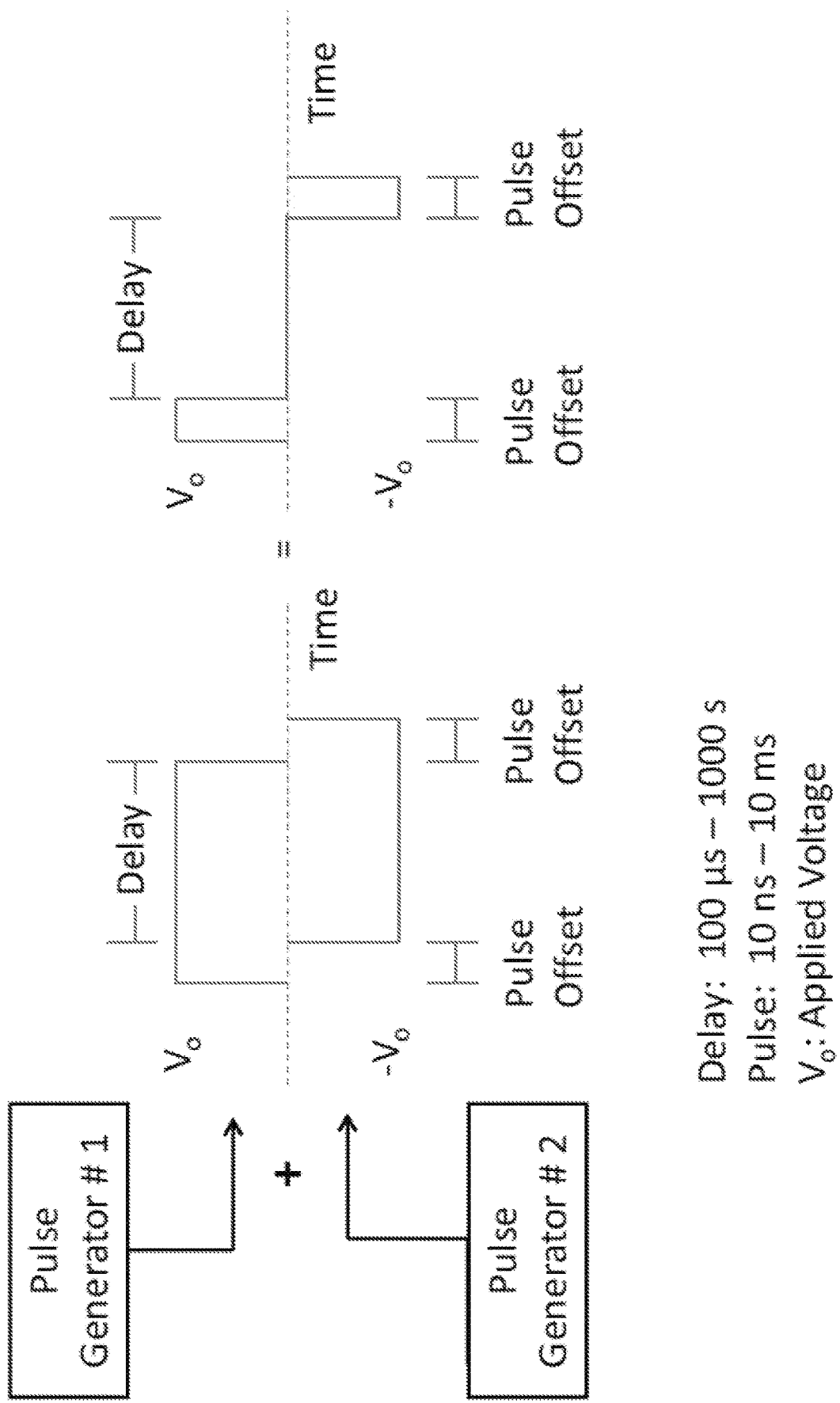
FIGS. 25A-B are schematic diagrams showing variations in techniques for generating bipolar electrical pulses in accordance with embodiments of the invention.

FIG. 25A illustrates the concept of overlapping the equal but opposite charges delivered from separate pulse generators. In particular, a first pulse generator administers a first positive pulse for a desired amount of time. Here, the pulse has a duration in the 10 ns to 10 ms range. At some time after the first pulse is generated, a second pulse from a second pulse generator is administered. In this example, the second pulse is of the same magnitude as the first pulse yet opposite in polarity. By overlapping the pulses, or simultaneously applying the pulses, the net effect during the overlap is that the tissue does not experience a charge. In effect the overlap of the pulses creates a delay and the charge delivered to the tissue is only the portion of each pulse that is outside of the overlap, i.e., the offset.

Figure 25B:
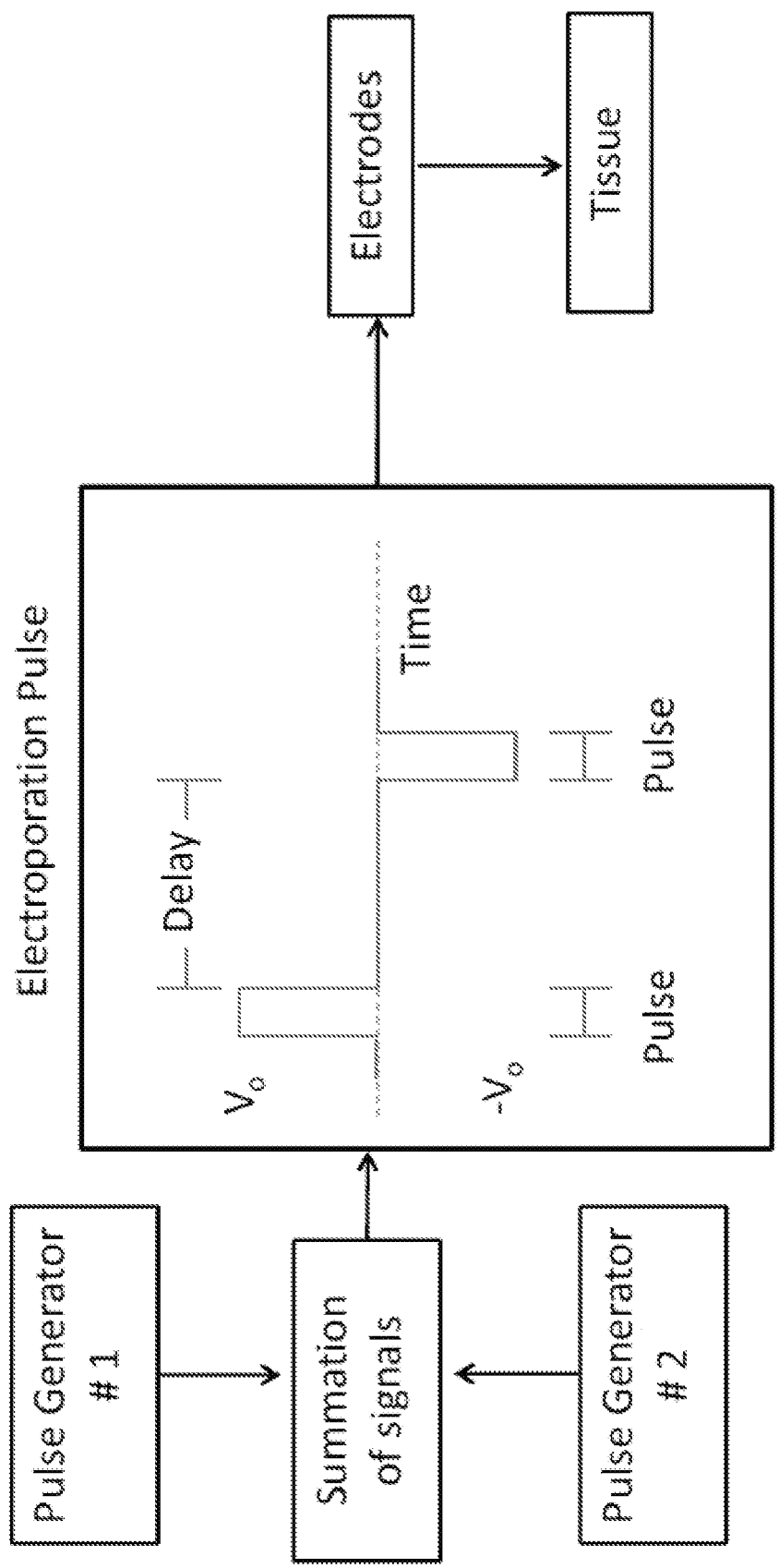

FIG. 25B illustrates one example of administering opposing polarity pulses from two pulse generators simultaneously, but offset and with no overlap. As shown, a first positive electrical pulse is initiated by a first pulse generator. At a desired time following administration of the first pulse, a second pulse equal in magnitude to the first pulse but opposite in charge is initiated using a second pulse generator. It is noted that in this figure that although a summation of the two individual signals offset by a delay (pulse duration) is shown, one of skill in the art could easily incorporate additional signals in order to manipulate additional pulse parameters. Further, and as with all embodiments described in this specification, the positive and negative applied voltages do not have to be of equal magnitude.

In one such embodiment, electrical pulses are delivered in a series of two pulses of alternating polarity (from millisecond to nanosecond range). Use of alternating polarities reduces or eliminates charge buildup on the electrode(s). For example, two NanoKnife™ (AngioDynamics, Queensbury, N.Y.) devices can be linked to the same electrode array, and programmed to deliver synched or slightly offset pulses to the electrodes. The first pulse can generate a 2500 V/cm electric field of 500 ns duration. This pulse is followed immediately (yet slightly offset) by the onset of a second pulse, which generates a −2500 V/cm electric field for 500 ns. The net effect of the pulses in the tissue is a net charge of zero and an additional benefit is avoiding the need for complex circuitry as the need for abrupt switching of the polarity is obviated.

Also during implementation of a desired treatment protocol, the systems, methods, and or devices according to the invention can be operably configured to monitor certain variables, such as temperature of the electrodes and/or surrounding tissue. If monitored during the procedure and in real time, adjustments to the protocol, including adjustments to the type, length, number, and duration of the pulses, could then be made, if necessary, to avoid damage of the tissue being treated.

Example VI: Parameters

The following are parameters that can be manipulated within the IRE treatments discussed herein.
Pulse length: 5 μs-1 ms
Number of pulses: 1-10,000 pulses
Electric Field Distribution: 50-5,000 V/cm
Frequency of Pulse Application: 0.001-100 Hz
Frequency of pulse signal: 0-100 MHz
Pulse shape: square, exponential decay, sawtooth, sinusoidal, alternating polarity Positive, negative, and neutral electrode charge pulses (changing polarity within probe)
Multiple sets of pulse parameters for a single treatment (changing any of the above parameters within the same treatment to specialize outcome).

It is important to note that bipolar pulses are only effective for electroporation if each pulse within the train is long enough in duration to charge the plasma membrane to a permeabilizing level. If this is not the case, the pulses offset each other from fully charging the plasma, and supraporation effects dominate when the pulse amplitude is increased. Additionally, a delay can be included between pulses within the train, or the total number of pulses within the train can be controlled, to limit the Joule heating in the tissue while still delivering a lethal dose of energy. Embodiments of the invention are equally applicable to any electroporation-based therapy (EBT), including therapies employing reversible electroporation, such as gene delivery therapy and electrochemotherapy, to name a few. One of skill in the art is equipped with the skills to modify the protocols described herein to apply to certain uses.

The repetition rate of pulse trains can also be controlled to minimize interference with, and allow treatment of vital organs that respond to electrical signals, such as the heart. The concept of alternating polarity of pulses can be extended to the use of multiple electrodes. For example, a combination of three electrodes can be used to deliver three sequential sets of alternating polarity pulses to a target tissue. More specifically, Electrode A can be used to deliver a 500 ns pulse at 1000 V at a starting time (T=0) and a 500 ns pulse at −1000 V at T=1 μs. Electrode B can be used to deliver a 500 ns pulse at 1000 V at T=500 ns, and a 500 ns pulse at −1000 V at T=1.5 μs. Electrode C can be used to deliver a 500 ns pulse at 1000 V at T=1 μs, and a −1000V pulse at T=2.0 μs. Of course, this concept can be applied using any numbers of electrodes and pulse times to achieve highly directed cell killing.

Example V

Monitoring Temperature During Electroporation Procedures

One of the main advantages of N-TIRE over other focal ablation techniques is that the pulses do not generate thermal damage due to resistive heating, thus major blood vessels, extracellular matrix and other tissue structures are spared. See B. Al-Sakere, F. Andre, C. Bernat, E. Connault, P. Opolon, R. V. Davalos, B. Rubinsky, and L. M. Mir, "Tumor ablation with irreversible electroporation," PLoS ONE, vol. 2, p. e1135, 2007; and J. F. Edd, L. Horowitz, R. V. Davalos, L. M. Mir, and B. Rubinsky, "In vivo results of a new focal tissue ablation technique: irreversible electroporation," IEEE Trans Biomed Eng, vol. 53, pp. 1409-15, July 2006, both of which are incorporated by reference herein in their entireties. The inventors have found that with real time temperature data measured at the electrode-tissue interface, the non-thermal aspect of the technique can be confirmed. One such way to measure temperature in-vivo during the pulse delivery is to use fiber optic probes.

Figures 25C, 26A, 26B:
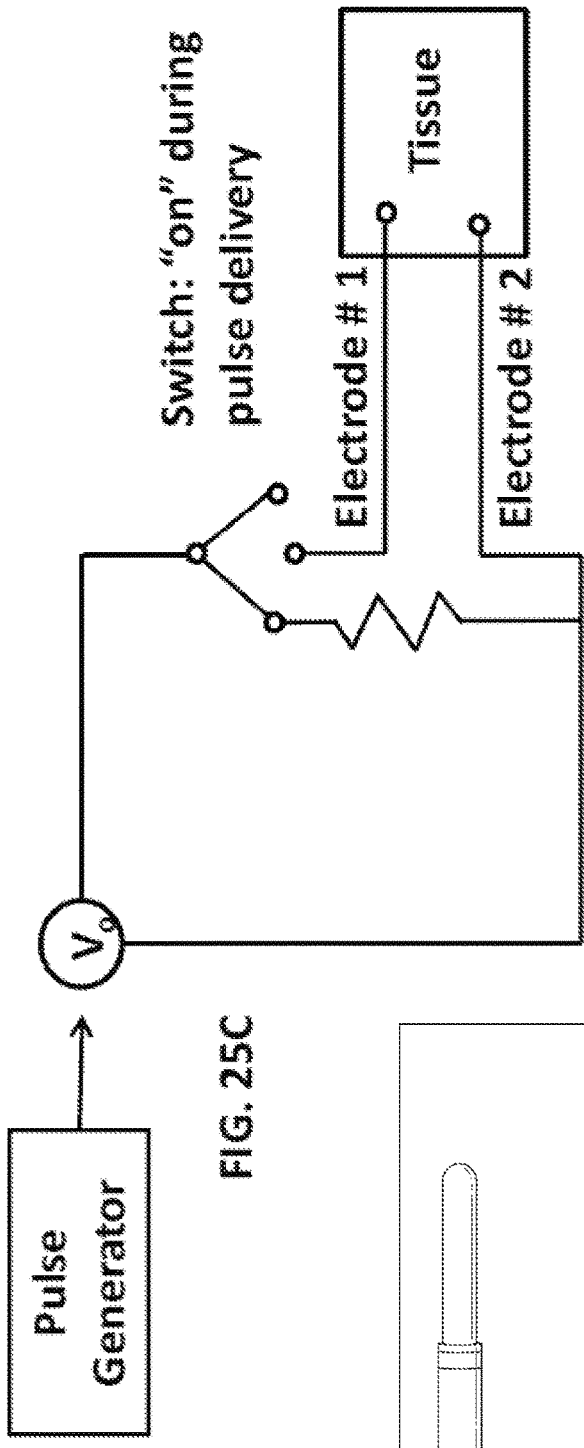
FIG. 25C is a schematic diagram of a representative circuit model for generating and administering simultaneous, continuous, but offset pulses as shown in FIG. 25A.
FIG. 26A is a photograph showing the N-TIRE electrodes with attached fiber optic probes, which were used in this intracranial treatment of white matter to measure temperature during pulse delivery.
FIG. 26B is a graph showing temperature [° C.] distribution during an N-TIRE treatment in the white matter of a canine subject.

In an experiment performed by the inventors, temperatures were measured in the brain during an N-TIRE procedure using the Luxtron® m3300 Biomedical Lab Kit Fluoroptic® Thermometer (LumaSense™ Technologies, Santa Clara, Calif. USA). STB medical fiber optic probes (LumaSense™ Technologies, Santa Clara, Calif. USA) were placed at the electrode-tissue interface and 7.5 mm along the insulation. FIG. 26A is a photograph showing the N-TIRE electrodes with attached fiber optic probes, which were used in this intracranial treatment of white matter to measure temperature during pulse delivery.

After insertion of the electrodes, four sets of twenty 50 μs pulses were delivered with a voltage-to-distance ratio of 1000 V/cm between the electrodes. The electrode exposure and separation distance were each 5 mm. The polarity of the electrodes was alternated between the sets to minimize charge build-up on the electrode surface. These parameters were determined from previous in-vivo N-TIRE procedures which showed sufficient ablation of tissue. The NanoKnife® was synchronized with the dog's heart rate in order to prevent any ventricular defibrillation or arrhythmias.

For treatment planning purposes, in order to model accurate N-TIRE treatment, it is beneficial to incorporate changes in conductivity due to permeabilization of the tissue (as described in detail in the treatment planning section of this specification), as well as incorporate information relating to temperature changes. See P. A. Garcia, J. H. Rossmeisl, R. E. Neal, II, T. L. Ellis, J. Olson, N. Henao-Guerrero, J. Robertson, and R. V. Davalos, "Intrracranial Non-Thermal Irreversible Electroporation: In vivo analysis," *Journal of Membrane Biology*, p. (in press), 2010, which is incorporated by reference herein in its entirety. Conductivity changes due to thermal effects could have important implications with a number of different treatment parameters, including electrode geometry and pulse parameters (i.e., duration, number, amplitude, and repetition rate, etc.).

FIG. 26B is a graph showing temperature [° C.] distribution during an N-TIRE treatment in the white matter of a canine subject. More particularly, what is shown is the temperature distribution measured by the probe located at the electrode-tissue interface and 7.5 mm above the insulation. It is important to note that the starting temperature was approximately 33° C. due to the anesthesia effects and this is neuro-protective during brain procedures in general and that the total pulse delivery took around 300 seconds. For the probe at the interface, four sets of mild increase in temperatures are seen. The probe in the insulation also shows some very mild increase in temperature that is probably due to heat conduction from the treatment region.

The changes in the temperature resulting from N-TIRE are less than 0.5° C. and they are not sufficient to generate thermal damage. This confirms that any cell death achieved by the procedure was a direct result of N-TIRE since at the electrode-tissue interface the highest thermal effects are expected to be achieved. It is also apparent from this data that it can be assumed in numerical modeling that electrical conductivity changes due to electroporation only and not temperature.

Figure 27A:
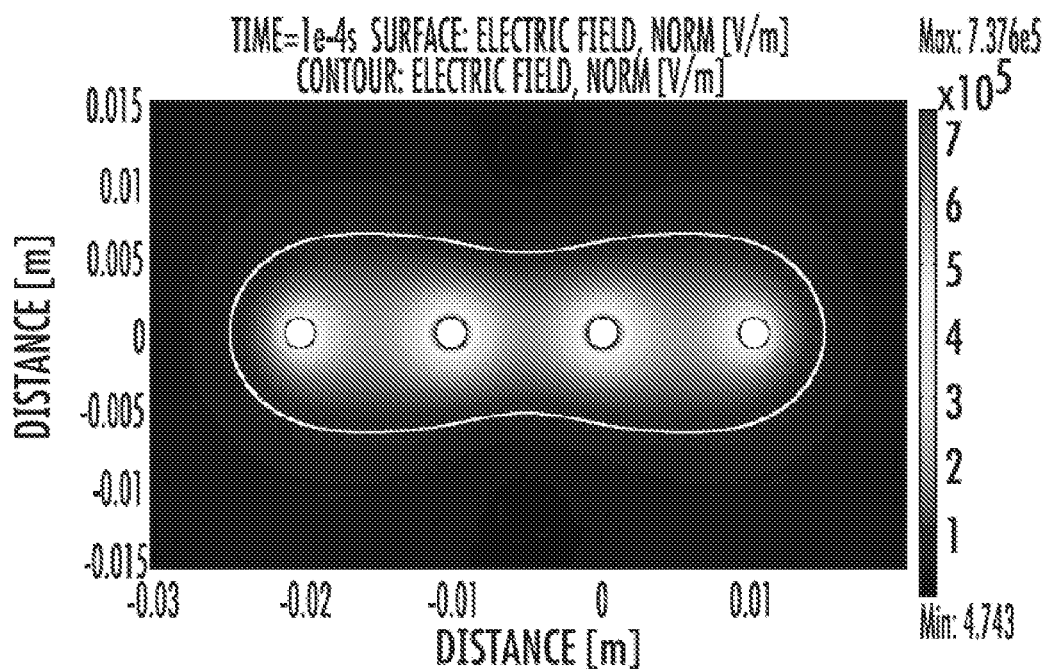
FIGS. 27A-J depict electrical field outputs for various combinations of electrodes emitting different charges.
Figure 27B:
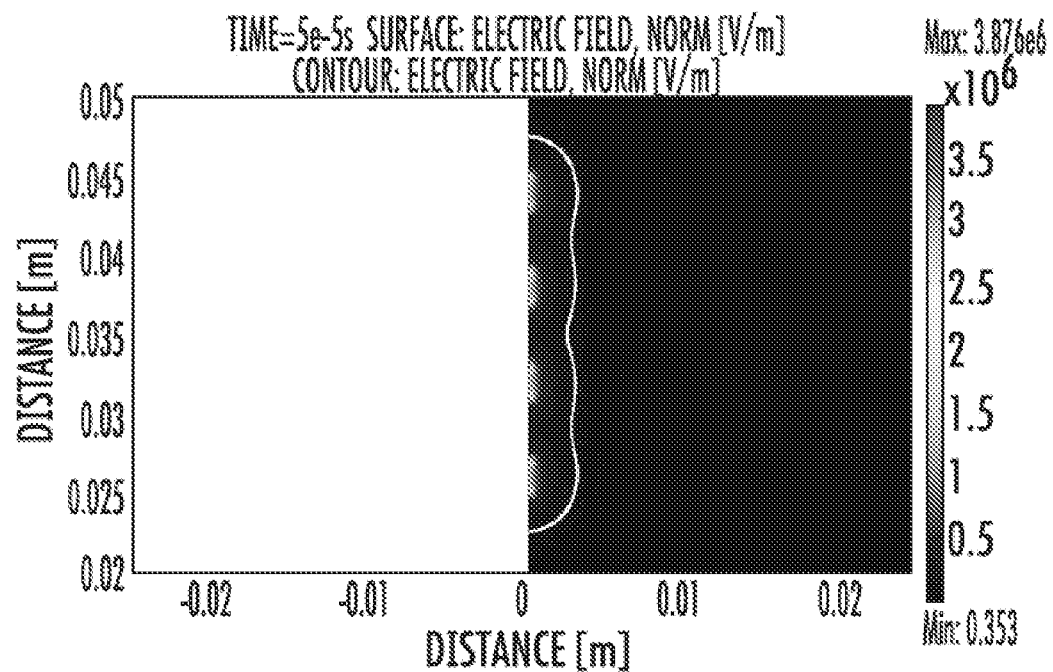
Figure 27C:
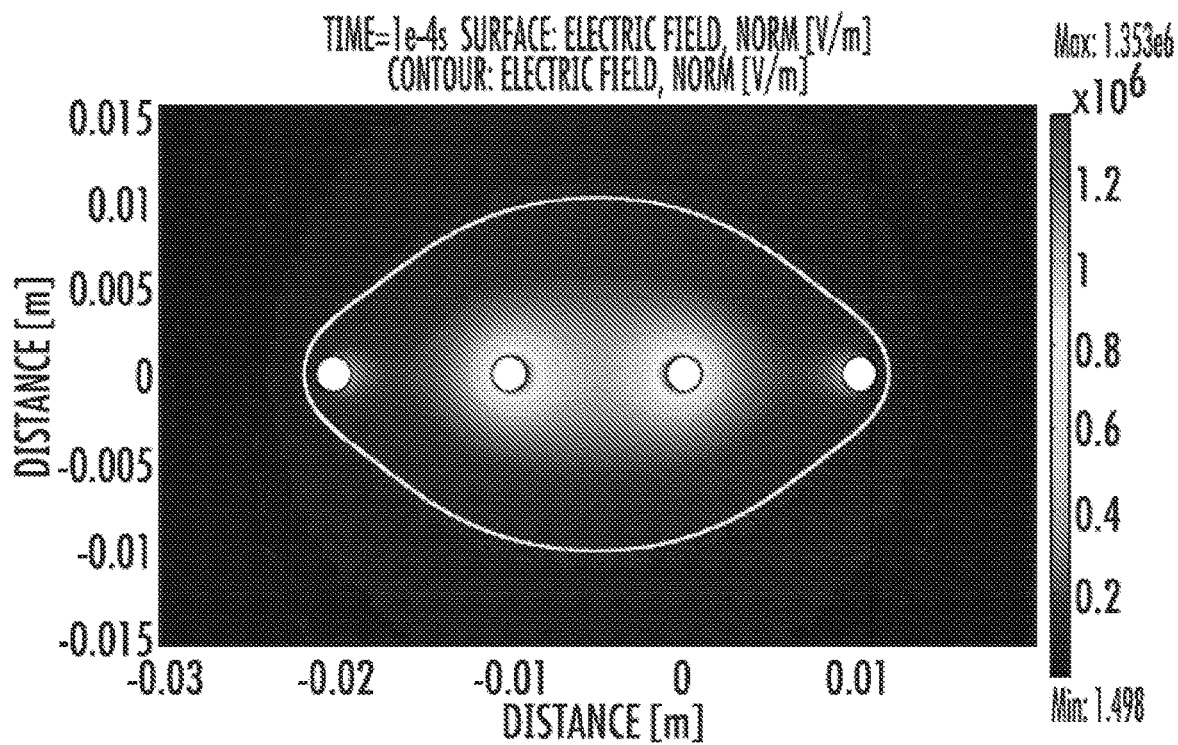
Figure 27D:
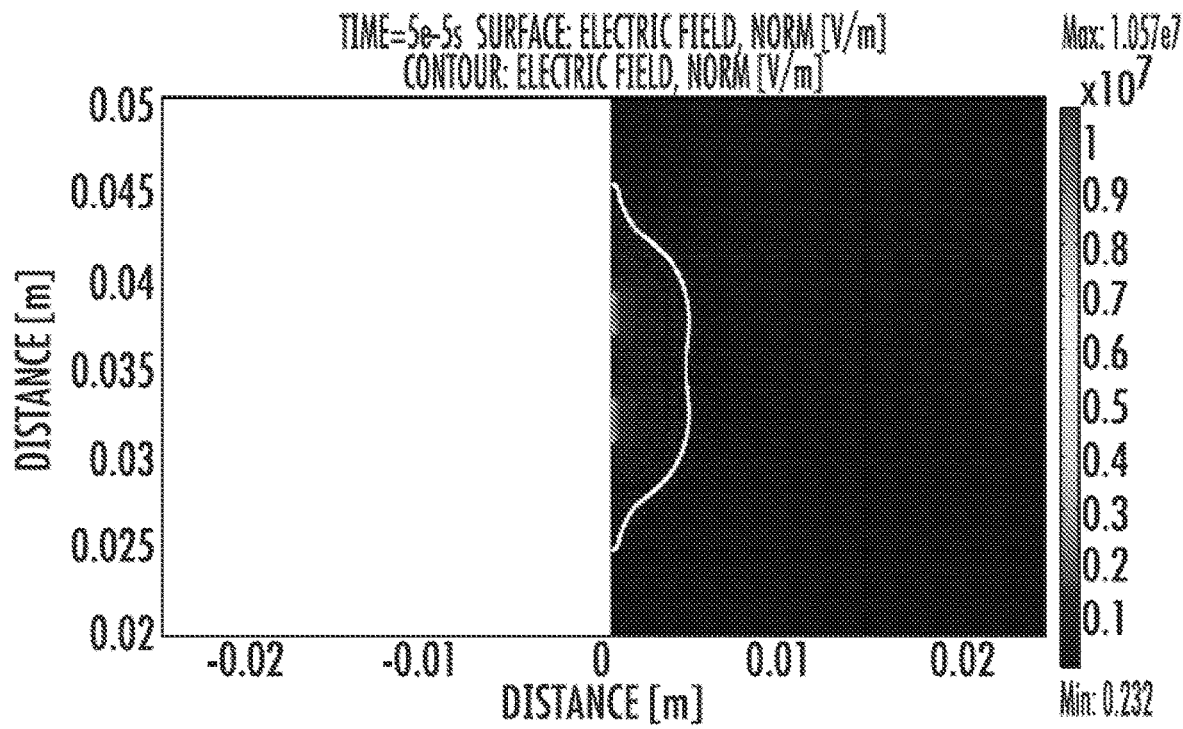
Figure 27E:
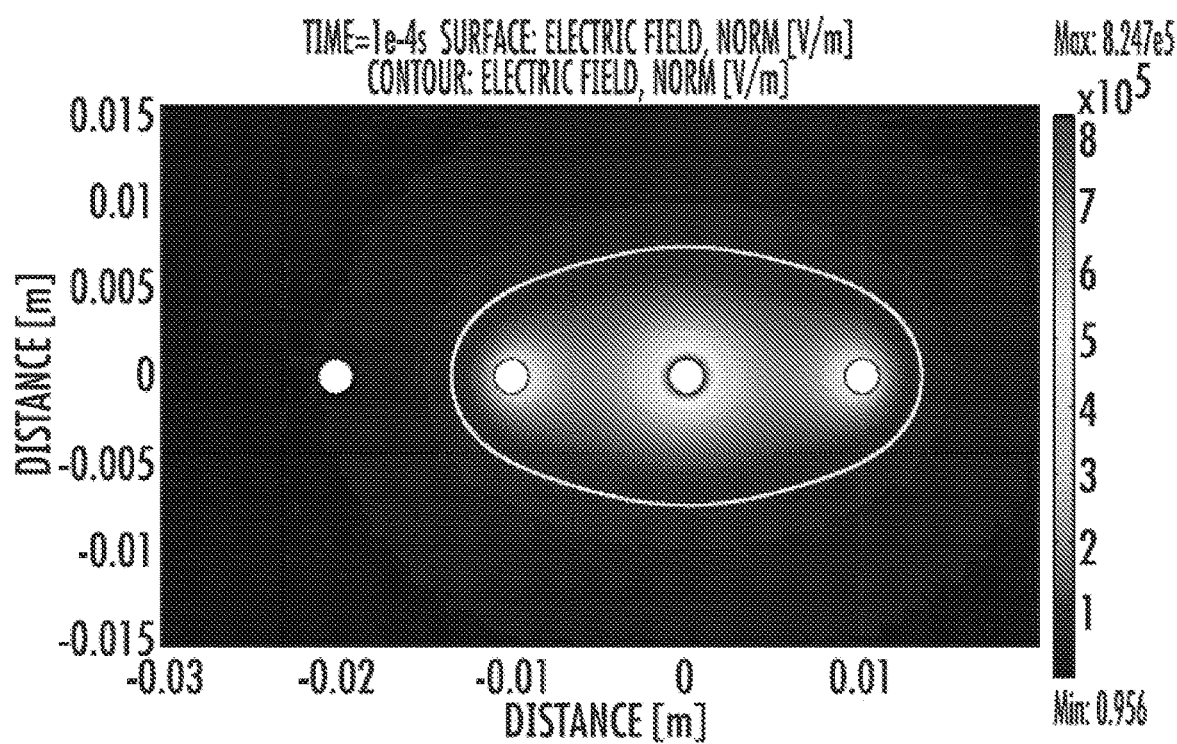
Figure 27F:
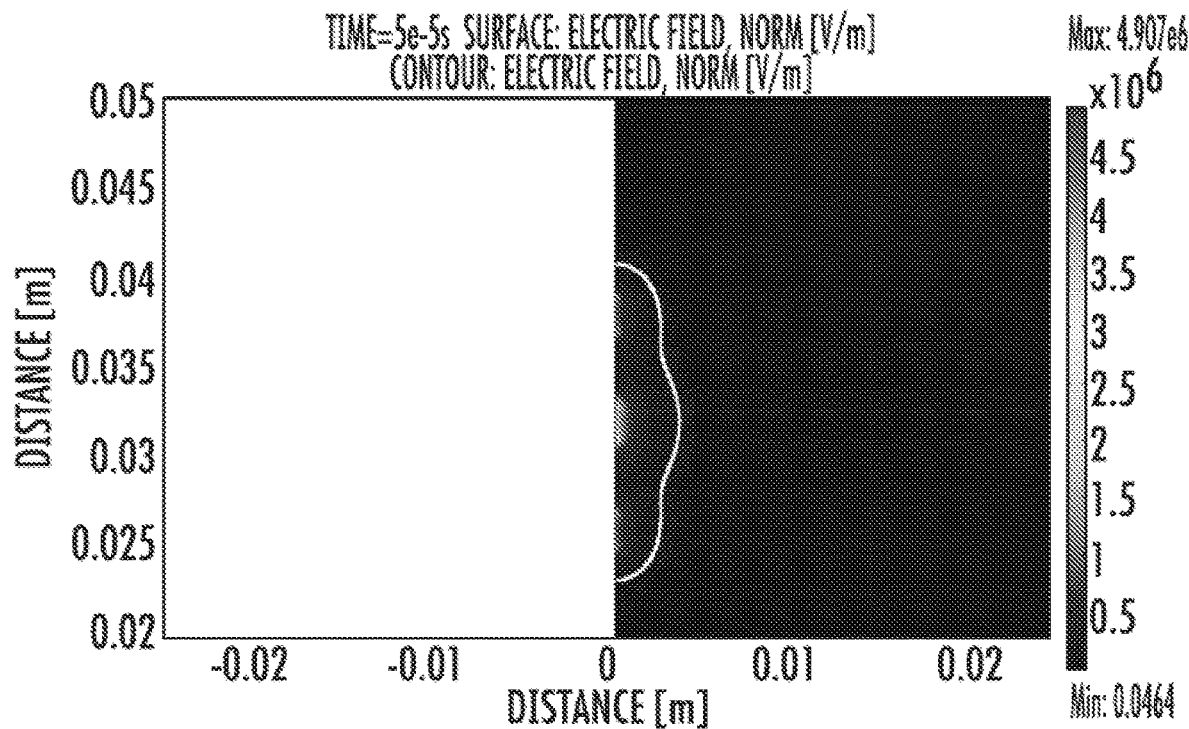
Figure 27G:
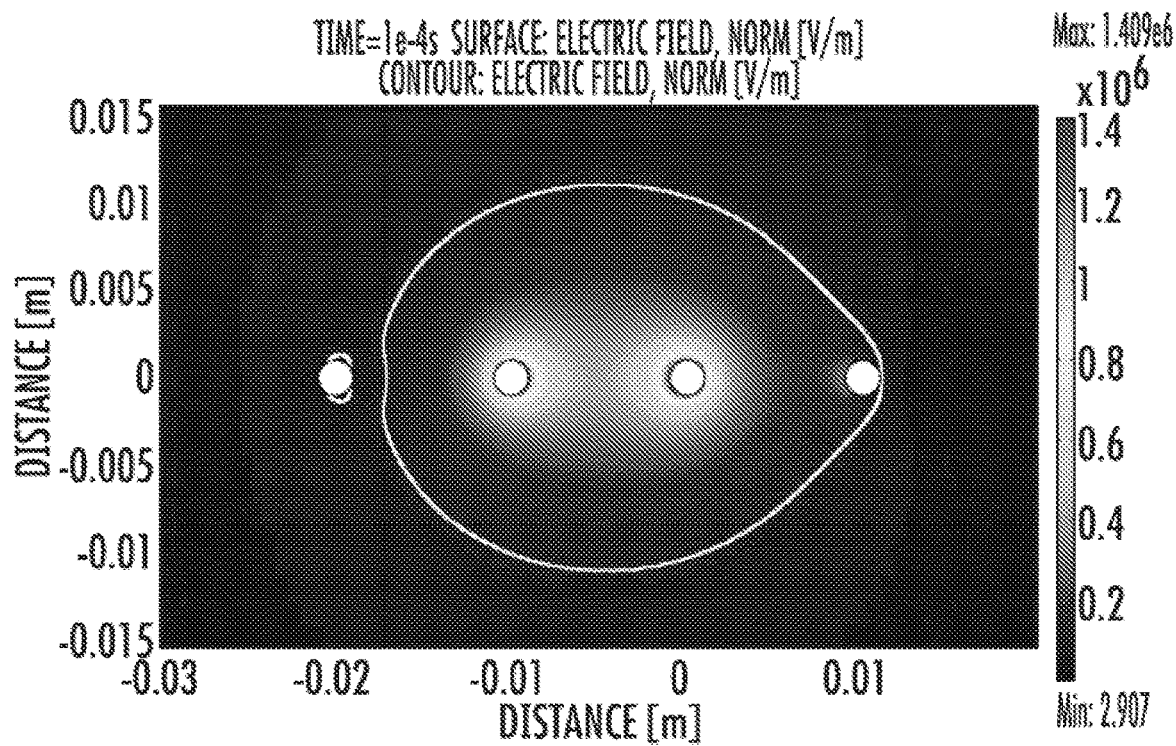
Figure 27H:
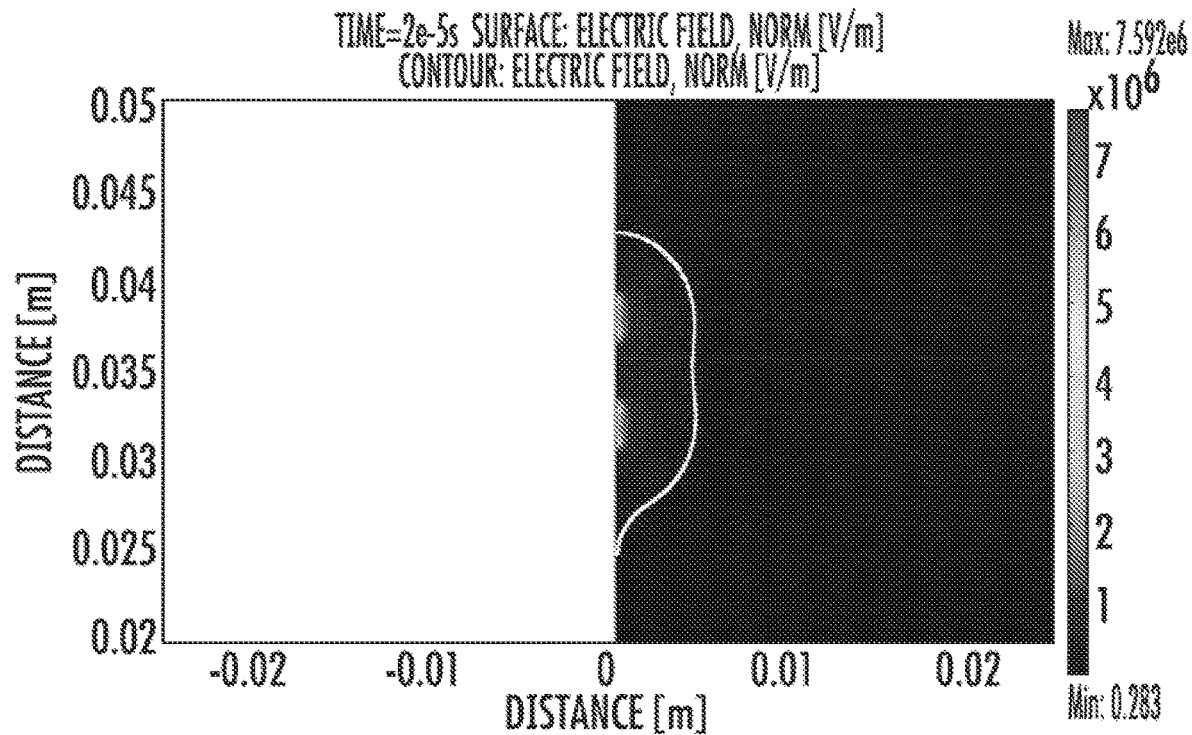
Figure 27I:
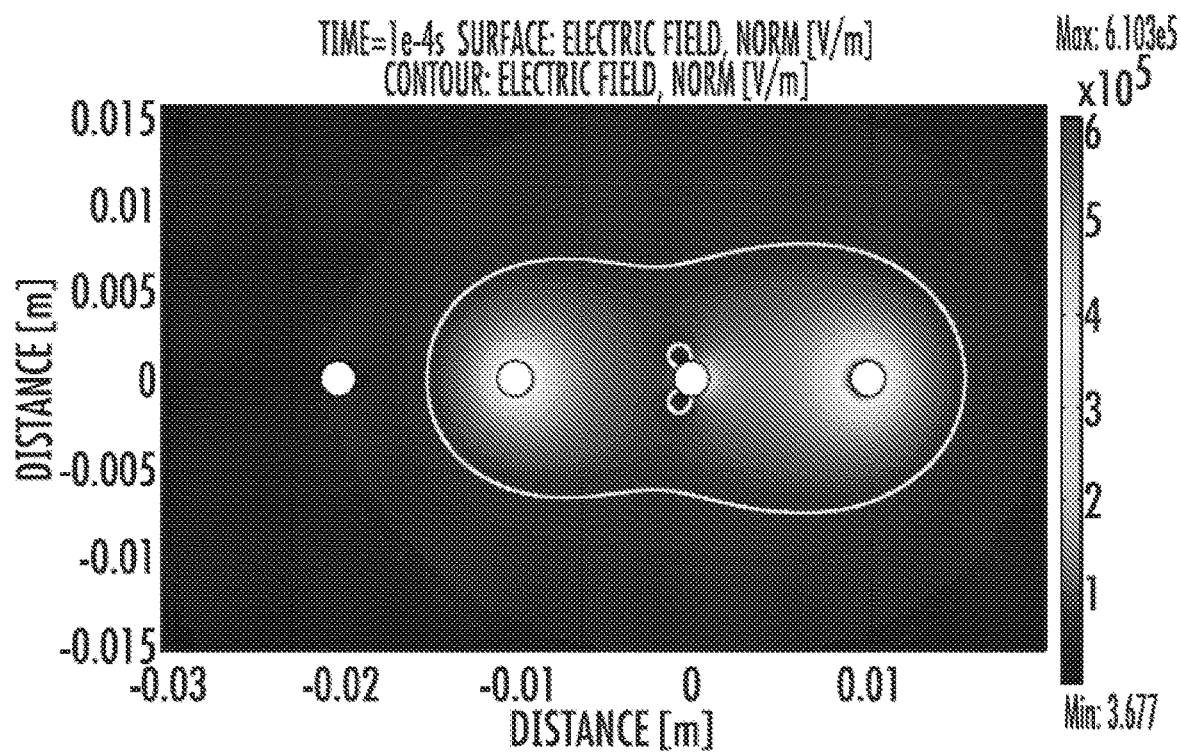
Figure 27J:
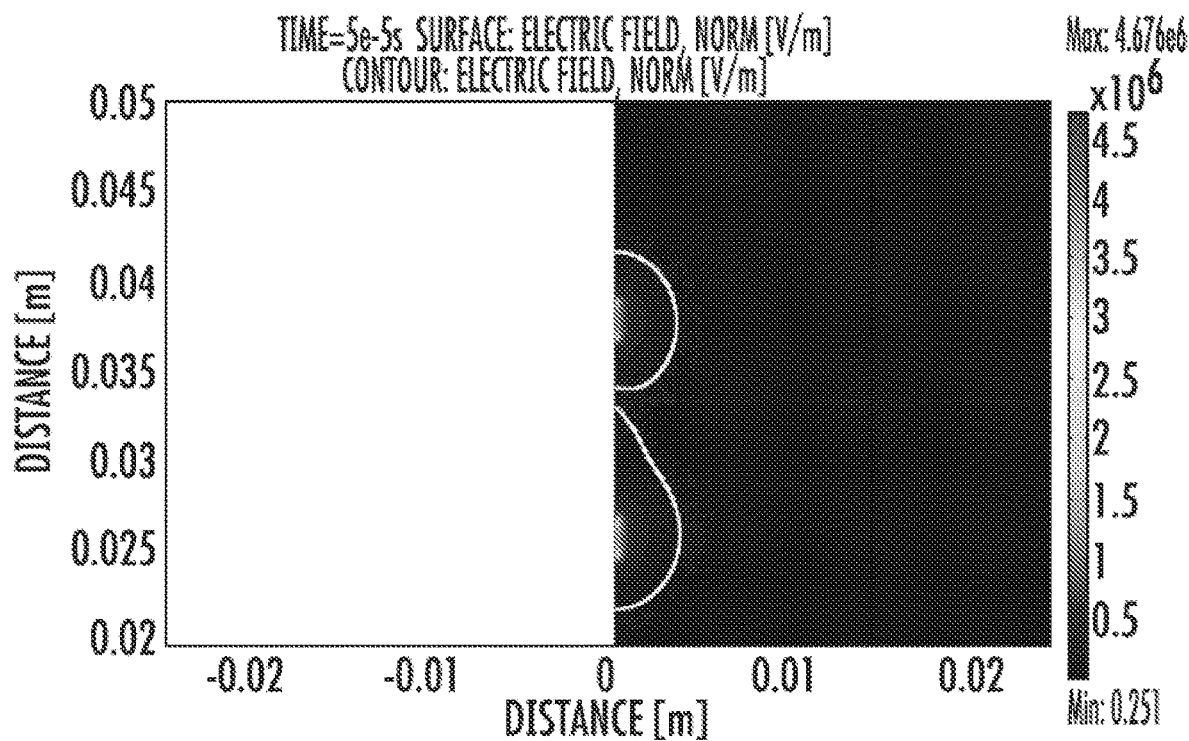

We have discovered that a highly customizable electric field distribution may be attained by combining multiple electrode charges within the same pulse. This allows a highly customized and controllable treatment protocol to match the dimensions of the target tissue. In addition, the invasiveness of the treatment may be decreased by reducing the number of electrode placements required for treatment. In order to demonstrate the great flexibility in electric field distribution shape, 2-dimensional and axis symmetric models were developed with 3 and 4 electrode arrays along a single axis. The results are depicted in FIGS. 27A-D. For development of the data, only the electric potentials of the electrodes were manipulated to achieve the great flexibility needed in IRE treatment planning. For FIGS. 27A and B, four charged electrodes of alternating polarity at 2500V and ground were used to develop a 2-D readout (FIG. 27A) and axis symmetric electrode configurations (FIG. 27B). Four charged electrodes with the center two at 5000V and 0V and the outer two electrodes at 2500V were used to develop a 2-D readout (FIG. 27C) and axis symmetric electrode configurations (FIG. 27D). Three charged electrodes with the center one at 2500V and the outer two at 0V were used for 2-D (FIG. 27E) and axis symmetric electrode (FIG. 27F) configurations. Three charged electrodes with the center at 0V, left electrode at 5000V, and right electrode at 2500V for 2-D (FIG. 27G) and axis symmetric (FIG. 27H) scenarios. Three charged electrodes with the center at 1750V, left electrode at 3000V and right electrode at 0V for 2-D (FIG. 27I) and axis symmetric electrode (FIG. 27J) configurations.

Example VI

Experimental Results of High-Frequency, Bipolar Pulses for Electroporation of Cells.

A chemical reaction technique was performed to fabricate parallel silver electrodes on glass microscope slides with 100 µm spacing. Briefly, a commercially available mirroring kit was used to deposit pure silver onto the microscope slides (Angel Gilding Stained Glass Ltd, Oak Park, Ill.). A negative thin film photoresist (#146DFR-4, MG Chemicals, Surrey, British Colombia, Canada) was laid on top of the slide and passed through an office laminator (#4, HeatSeal H212, General Binding Corporation, Lincolnshire, Ill.). A photomask printed at 20$k$ DPI on a transparent film (Output City, Cad/Art Services Inc, Bandon, Oreg.) was placed ink side down onto the photoresist, and slides were exposed to UV light for 45 seconds. After exposure, the slides were placed in a 200 mL bath containing a 10:1 DI water to negative photo developer (#4170-500 ML, MG Chemicals, Surrey, British Colombia, Canada). The slides were placed in a beaker containing DI water to stop the development process and gently dried using pressurized air. Electrode structures on the microscope slides were fabricated by removing all silver not covered by the patterned photoresist. A two part silver remover was included in the mirroring kit used to deposit the silver. The photoresist was then removed by placing the slide in a bath of acetone.

Microfluidic channels were fabricated using the patterned photoresist on a microscope slide that had not undergone the silvering process. Liquid phase polydimethylsiloxane (PDMS) in a 10:1 ratio of monomers to curing agent (Sylgrad 184, Dow Corning, USA) was degassed under vacuum prior to being poured onto the photoresist master and cured for 1 hour at 100° C. After removing the cured PDMS from the mold, fluidic connections to the channels were punched in the devices using 1.5 mm core borers (Harris Uni-Core, Ted Pella Inc., Redding, Calif.). The PDMS mold was then bonded over the glass slides containing the patterned electrodes by treating with air plasma for 2 minutes in a PDC-001 plasma cleaner (Harrick Plasma, Ithaca, N.Y.).

Figure 28A:
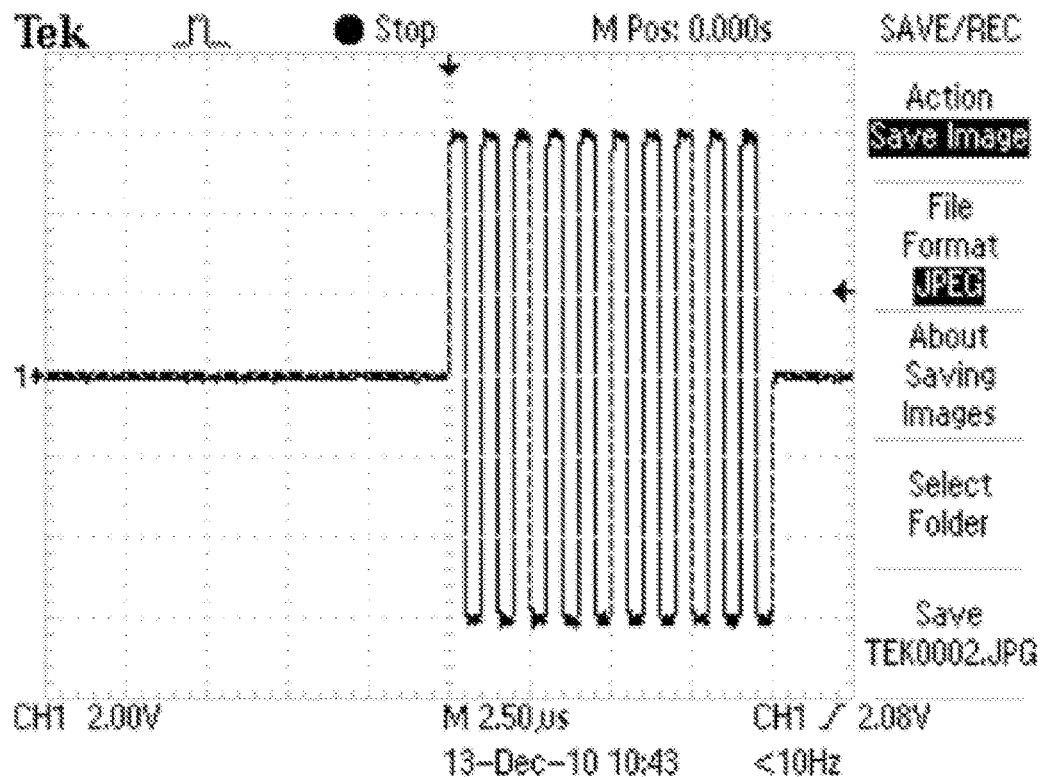
FIGS. 28A-B are graphs showing output of the arbitrary function generator prior to signal amplification by the high voltage MOSFET positive and negative polarity switches.
Figure 28B:
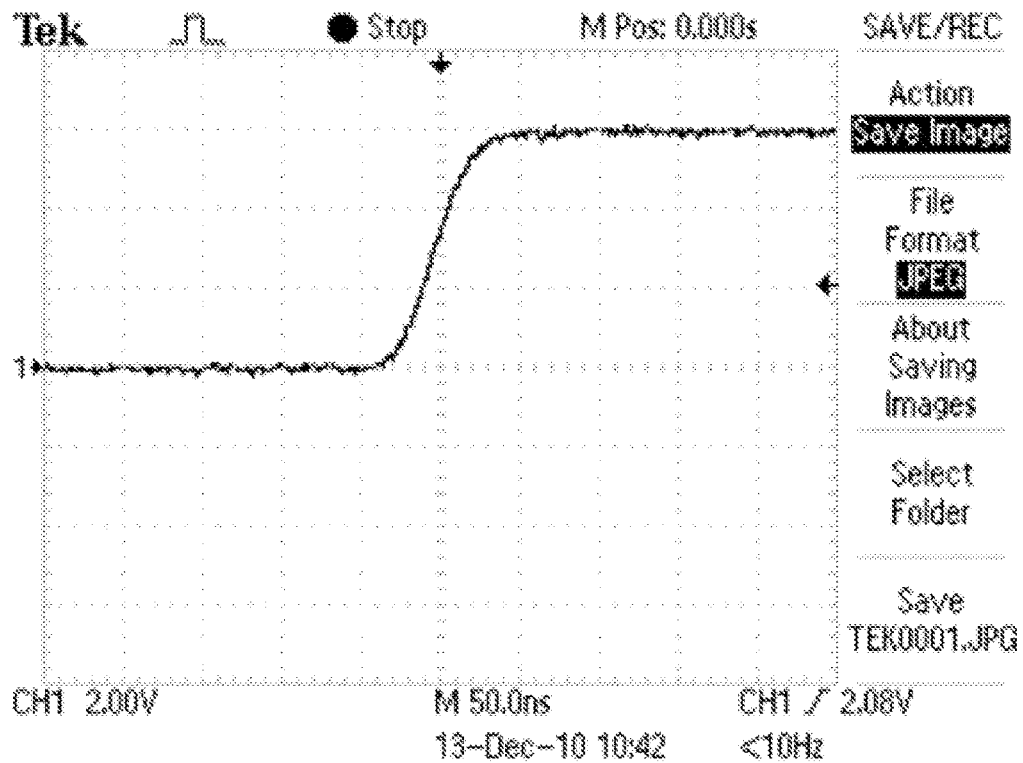

High voltage electrical wires were taped to the glass slide with exposed wire placed in direct contact with the electrical pads. A drop of high purity silver paint (Structure Probe Inc., West Chester, Pa.) was placed on the pad and allowed to dry for one hour creating a solid electrical connection. A drop of 5 minute epoxy (Devcon, Danvers, Mass.), used to secure the electrical connections, was placed on top of each electrode pad and allowed to cure for 24 hours. Pulses were delivered across the electrodes as described in EXAMPLE 4 prior to the amplification stage. No amplification was needed as the gap between the electrodes was only 100 µm. Therefore, the output signal of a function generator (GFG-3015, GW Instek, Taipei, Taiwan)+/−10 V can be used to generate an electric field capable of inducing electroporation, as shown in FIGS. 28A-B.

Figure 29B:
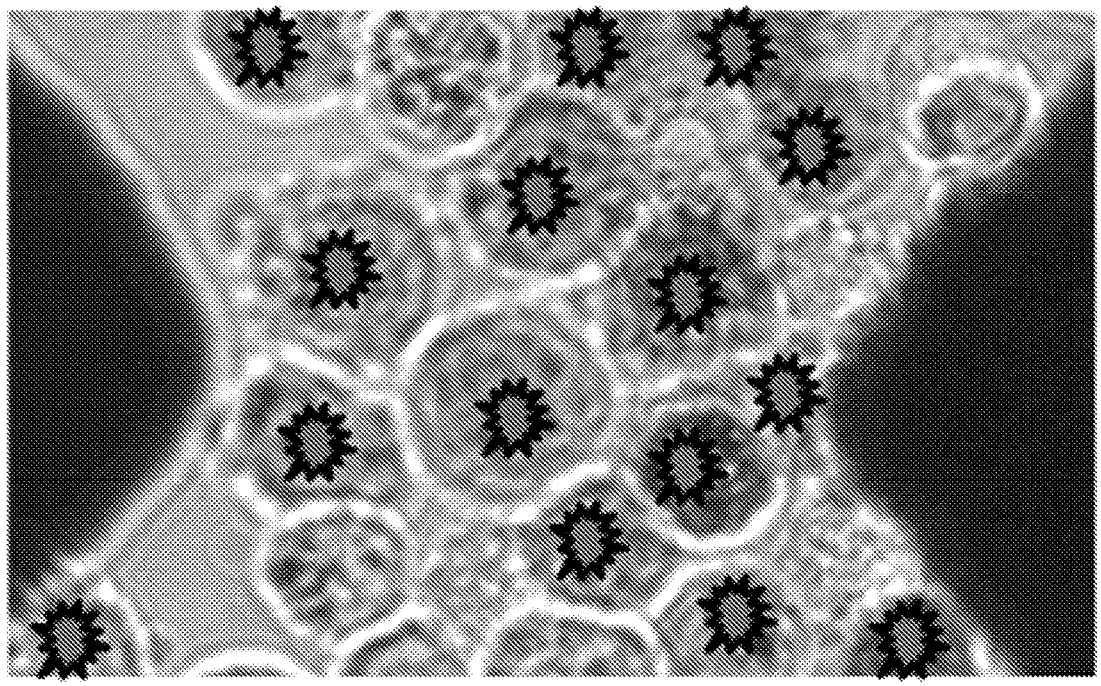
FIGS. 29A-B are micrographs showing in vitro experimental results on electroporation with high-frequency bipolar, pulses using a trypan blue dye exclusion assay.
Figure 29A:
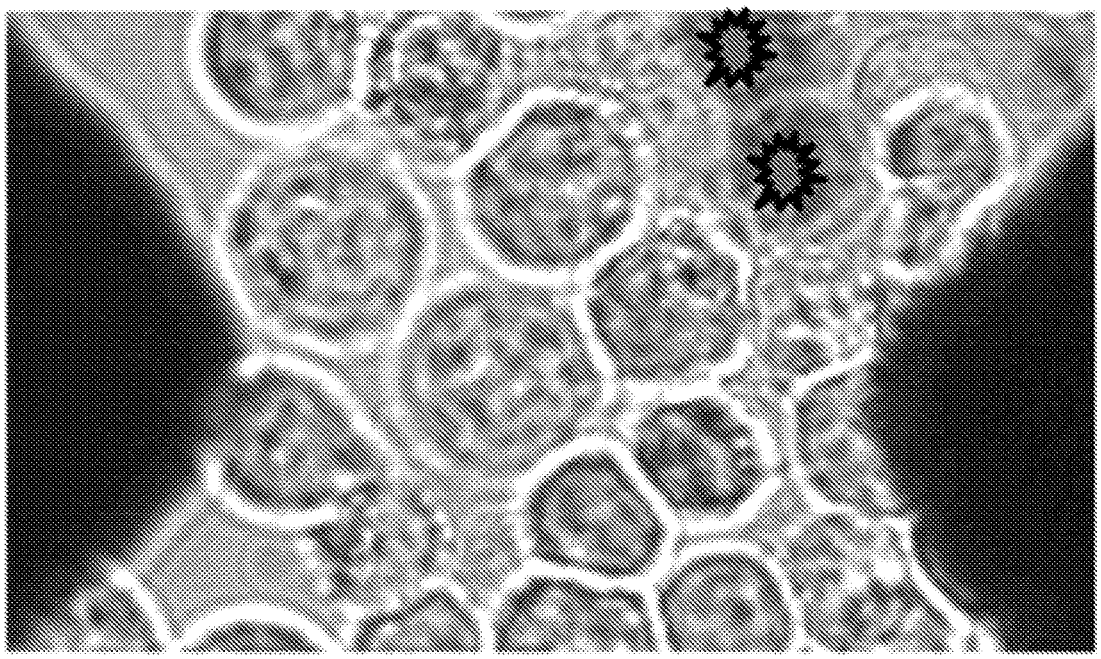

Following culture in DMEM-F12 (supplemented with 10% FBS and 1% penicillin streptomycin) MDA-MB-231 cells were resuspended in a PBS solution 1:1 with Trypan Blue (0.4%). Trypan Blue is a determinant of cell membrane integrity, and stains electroporated cells blue, whereas non-electroporated cells remain transparent. Cells at a concentration of $10^6$/ml were injected into the microfluidic channel using a syringe. The function generator was triggered by the microcontroller to deliver 80, 50 kHz bursts with a width of 1 ms and an amplitude of 500 V/cm. Results shown in FIGS. 29A-B, which shows that 60% transfection efficiency was obtained when starting with cells that are 92% viable. This efficiency of reversible electroporation could be improved by either increasing the number of pulses or the burst width. Additionally, IRE could be performed by increasing the applied voltage.

Example VII

Alternate Waveforms for Performing High-Frequency Electroporation.

Figures 30A, 30B, 30C:
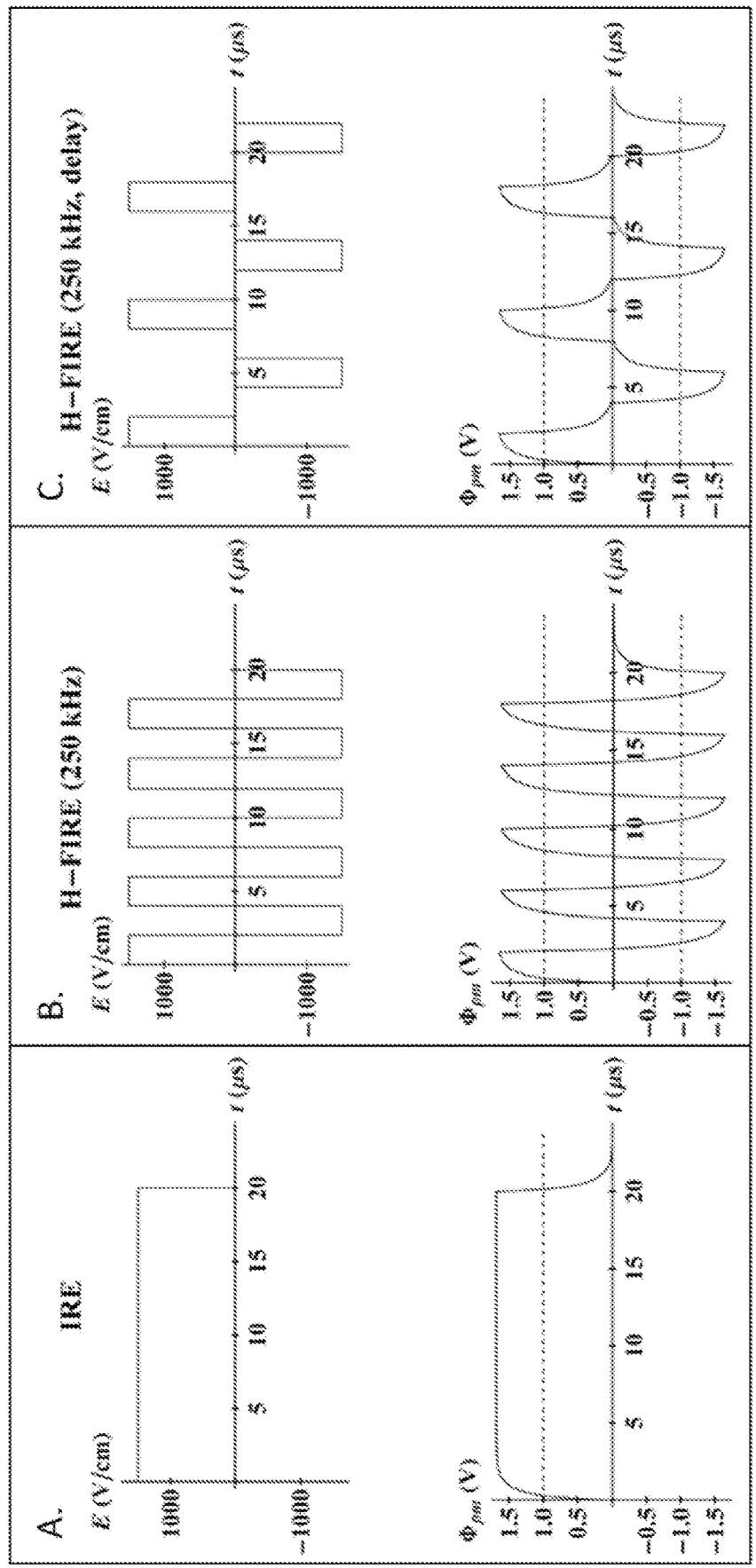
FIG. 30A-C are waveforms of IRE with unipolar pulses and high-frequency IRE with the corresponding TMP development across the plasma membrane ($\Phi_{pm}$) for a 1500 V/cm unipolar pulse (FIG. 30A) and a 1500 V/cm bipolar burst without a delay (FIG. 30B) and with a delay (FIG. 30C).
Figure 31:
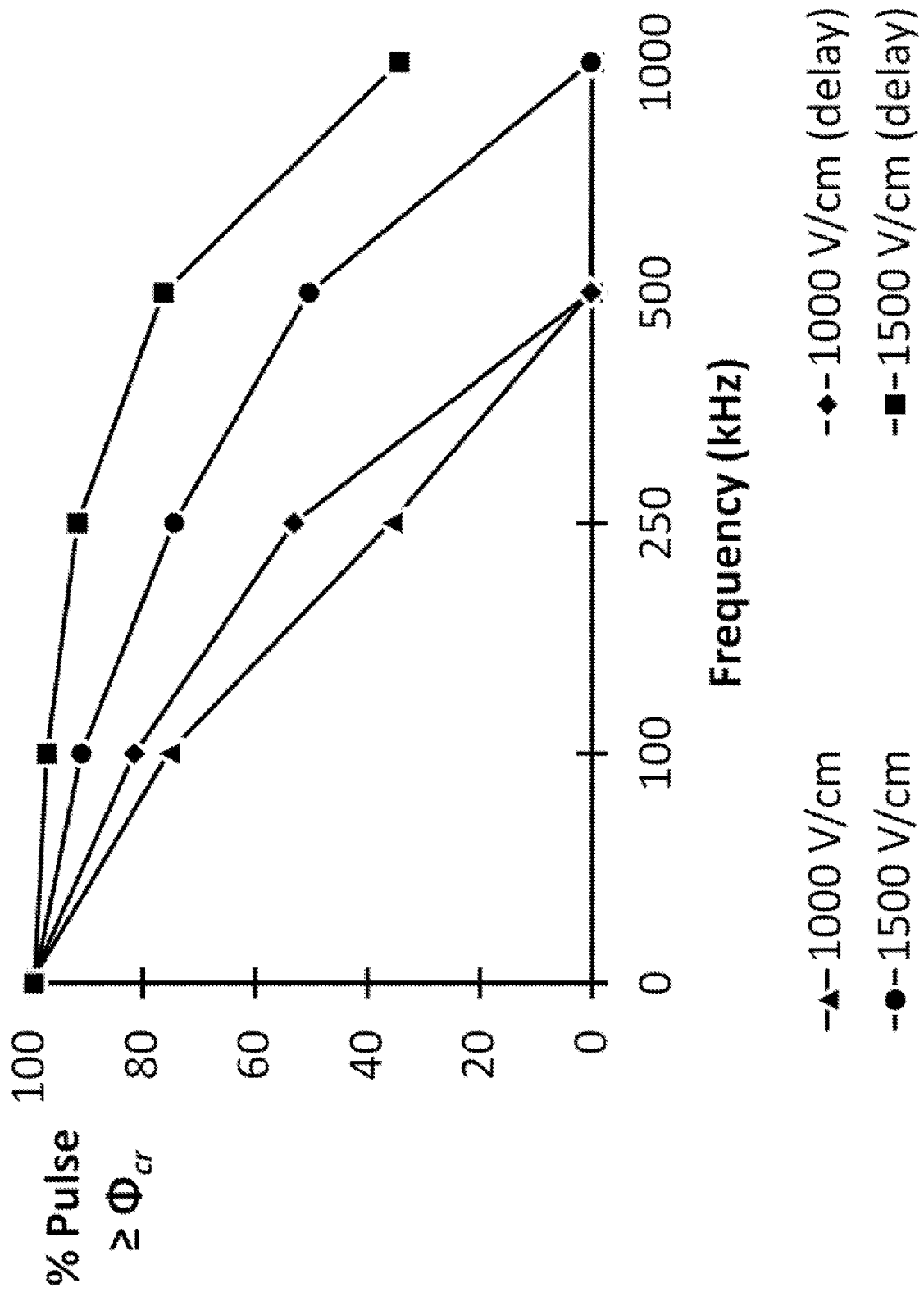
FIG. 31 is a graph comparing time above the critical threshold ($\Phi_{cr}$) for IRE at various center frequencies.

The analytical model for TMP described in the detailed description of the invention was utilized to investigate electroporation of a spherical cell subject to alternative waveforms. As mentioned, the critical TMP ($\Phi_{cr}$) across the plasma membrane required to induce IRE is approximately 1 V. Belehradek, J., S. Orlowski, L. H. Ramirez, G. Pron, B. Poddevin, and L. M. Mir, *Electropermeabilization of Cells in Tissues Assessed by the Qualitative and Quantitative Electroloading of Bleomycin*. Biochimica Et Biophysica Acta-Biomembranes, 1994. 1190(1): p. 155-163. This threshold is illustrated in FIGS. 15A-C by the dashed, horizontal line on the TMP profiles. Characteristic waveforms of IRE with unipolar pulses and high-frequency IRE with the corresponding TMP development across the plasma membrane ($\Phi_{pm}$). All results are presented at the cell pole (θ=0) to show the maximum TMP around the cell. Further, results are only shown for TMP across the plasma membrane, as the TMP across the nuclear envelope never approached the permeabilizing threshold. For an electric field of 1500 V/cm, results indicate that a unipolar pulse (FIG. 30A), a 250 kHz bipolar burst (FIG. 30B), and 250 kHz bipolar burst that includes delays between the pulses (FIG. 30C) are all capable of inducing IRE. However, the time above the threshold TMP varies between the different cases. The 1500 V/cm unipolar pulse causes the TMP to rise above the critical threshold for IRE (1 V, dashed line). The 1500 V/cm bipolar burst without a delay and with a delay causes the TMP to oscillate around the same critical threshold. This is investigated further in FIG. 30 for center frequencies of 0, 100, 250, 500, and 1000 kHz, with the 0 kHz case representing the unipolar pulse, and electric fields of 1000 V/cm and 1500 V/cm. FIG. 31 provides a comparison of time above the critical threshold ($\Phi_{cr}$) for IRE at various center frequencies. The burst width of the bipolar waveform that included delays was twice as long (40 µs) as the corresponding burst with no delays in order to generate an equivalent pulse on-time (20 µs). The amount of time that the TMP was above the critical value was normalized by the on-time and converted to a percentage. FIG. 30 illustrates that, for a given frequency, as the electric field is increased from 1000 V/cm to 1500 V/cm, the percentage of the burst above the critical TMP also increases. At 250 kHz, IRE is possible during all waveforms, but at 500 kHz, only the waveforms with amplitudes of 1500 V/cm are capable of inducing IRE. As the center frequency of the burst increases, the percentage of the burst above the critical TMP decreases. However, with the inclusion of delays between the pulses, this characteristic dispersion is shifted towards higher frequencies. At 1 MHz, only the 1500 V/cm waveform with delays can theoretically cause IRE.

Methods of the invention can have a pulse duration in the range of about 2 MHz (250 ns) to about 500 kHz (1 µs). For example, the pulse duration can be about 1 MHz (500 ns). In preferred embodiments, the duration of each pulse is in the range of about 100 to 10,000 ns. The pulses of any method of the invention can be delivered on a short enough timescale to flow through epithelial cells but are long enough to induce electroporation in underlying cells. In specific embodiments, a frequency of 500 kHz or 1 MHz or 250 kHz is used to treat underlying fat cells in a layer of fat disposed under the epidermis. As mentioned, there is a balance between employing pulses that are delivered on a short enough timescale to flow through epithelial cells but are long enough to induce electroporation in underlying cells. The time constant of 345 ns, predicted by the analytical model for TMP, falls between the 2 MHz (250 ns pulse duration) and 1 MHz (500 ns pulse duration) bursts. Further, the 500 kHz burst (1 µs pulse duration) is close to the time it takes the TMP to reach steady state. The amplitude can be chosen such that even the highest frequency burst is above the set voltage level for a certain amount of time. The results would hold if the applied field was doubled and the voltage level was set to the 1 V threshold for pore formation, due to the linear dependence of TMP on the electric field. Based on this criterion, a frequency of 500 kHz is best suited to treat cells in the fat layer, followed by 1 MHz and 250 kHz. As frequency is increased, the dielectric properties and electric field distribution in the skin and fat become more macroscopically homogeneous, but above 1 MHz, the pulse duration is not adequate for the cell to charge. Other systems are available in the literature for generating bipolar pulses, and the invention should not be limited to the system described above. For example, De Vuyst et al. built a generator around an NE555 timer configured as an astable multivibrator capable of producing up to 50 kHz bipolar pulses. De Vuyst, E., M. De Bock, E. Decrock, M. Van Moorhem, C. Naus, C. Mabilde, and L. Leybaert, *In situ bipolar Electroporation for localized cell loading with reporter dyes and investigating gap junctional coupling*. Biophysical Journal, 2008. 94(2): p. 469-479. In embodiments, the function generator can be triggered by the microcontroller to deliver 80, 50 kHz bursts with a width of 1 ms and an amplitude of 500 V/cm. For example, under such conditions, a 60% transfection efficiency can be obtained when starting with cells that are 92% viable. This efficiency of reversible electroporation could be improved by either increasing the number of pulses or the burst width. Additionally, IRE could be performed by increasing the applied voltage.

The theoretical model of TMP suggests that IRE should be possible up to 1 MHz for an electric field of 1500 V/cm. Including a delay between the positive and negative pulses comprising the bipolar burst offers a therapeutic advantage in addition to protecting the MOSFETs in the pulse generation system (see EXAMPLE 4) from ringing. By not forcing a discharge of the TMP with an immediate reversal of polarity, the cell is allowed to return to the resting TMP according to its characteristic time constant. As a result, the TMP is maintained above the critical voltage required for IRE for a longer amount of time. This metric has been recognized as a potential indicator of treatment outcomes in electroporation based therapies with bipolar waveforms. Garcia, P. A., J. H. Rossmeisl, R. E. Neal, T. L. Ellis, J. D. Olson, N. Henao-Guerrero, J. Robertson, and R. V. Davalos, *Intracranial Nonthermal Irreversible Electroporation: In Vivo Analysis*. Journal of Membrane Biology, 2010. 236(1): p. 127-136.

Figures 32A, 32B, 32C:
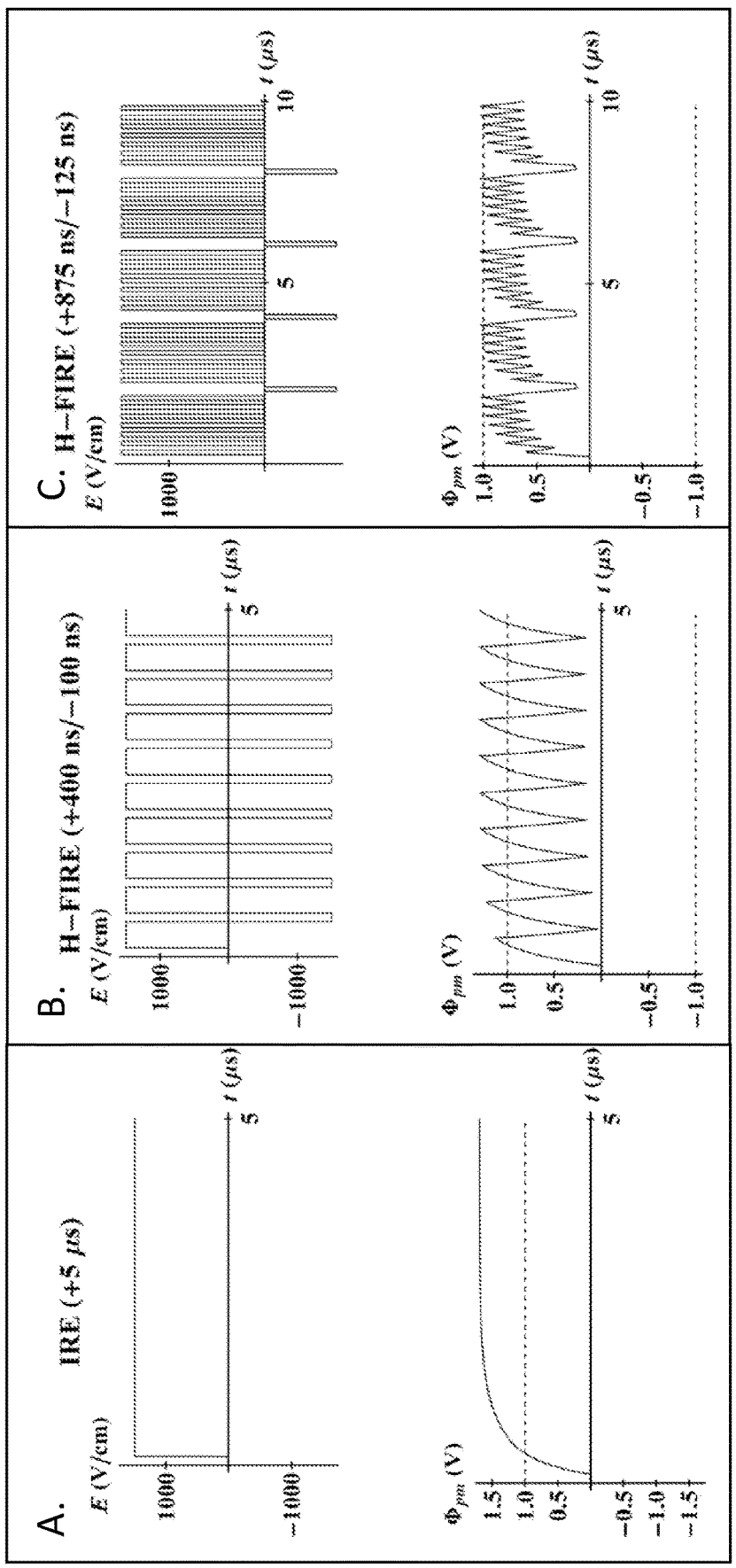
FIGS. 32A-C are waveforms of IRE with unipolar pulses and high-frequency IRE with the corresponding TMP development across the plasma membrane ($\Phi_{pm}$) for a 1500 V/cm unipolar pulse (FIG. 32A), a 1500 V/cm bipolar burst without a delay and with a shortened negative phase (FIG. 32B), and a 1500 V/cm bipolar burst with a delay and with a shortened, lower amplitude negative phase (FIG. 32C).
Figure 33:
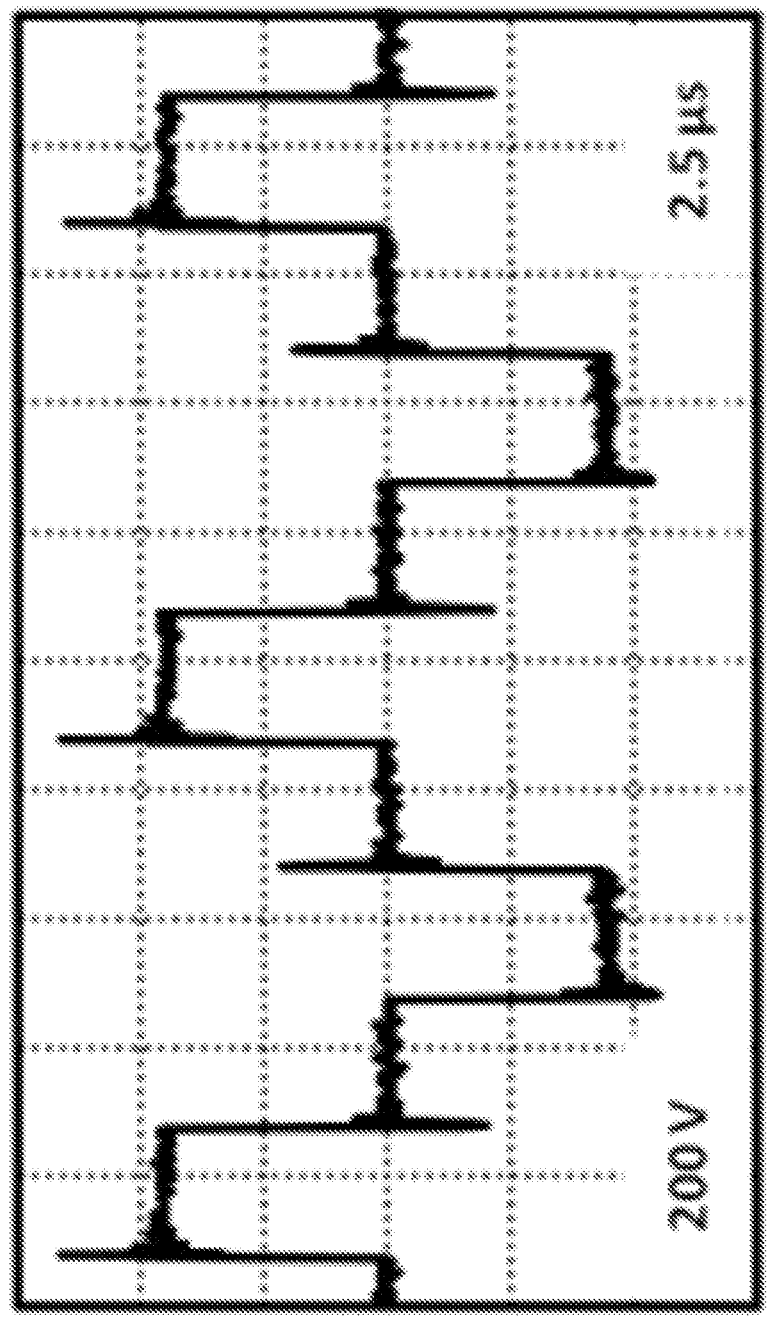
FIG. 33 is a chart showing an exemplary output from an in vivo treatment of the brain with high-frequency, bipolar pulses, where the snapshot is taken within a single burst.

Other potential waveforms for performing high-frequency electroporation are shown in FIGS. 31A-C, which provide characteristic waveforms of IRE with unipolar pulses and high-frequency IRE with the corresponding TMP development across the plasma membrane ($\Phi_{pm}$). A unipolar pulse with an amplitude of 1500 V/cm is shown for comparison (FIG. 32A). A waveform without delays between polarity reversals (FIG. 32B) can maintain a positive TMP throughout the entire treatment if the duration of positive polarity is tuned to be slightly longer than the duration of negative polarity. Similarly, for a waveform that includes delays (FIG. 32C), a train of positive ultra-short pulses could be used to gradually increase the TMP up to the critical permeabilizing threshold, and a single ultra-short pulse of negative polarity could follow the train without causing the TMP to go negative. In both examples, the ultra-short negative going pulse is designed to maintain the predicted benefits of high-frequency electroporation. Namely, it is predicted that the negative going pulse will prevent action potential generation and still permit a degree of capacitive coupling across epithelial layers. FIG. 33 is a chart showing an exemplary output from an in vivo treatment of the brain with high-frequency, bipolar pulses, where the snapshot is taken within a single burst.

Example VIII

The Electric Field Distribution During High-Frequency Electroporation can be Approximated by the Laplace Equation.

A 2D axisymmetric FEM representative of a slab of non-infiltrated fat adjacent to dry skin was simulated using COMSOL 4.2a (Burlington, Mass.). An energized and grounded electrode were modeled as infinite fins (0.5 mm diameter) separated 0.5 cm from the skin-fat interface, for a total spacing of 1 cm. The electric potential distribution within the tissue was obtained by transiently solving $$-\nabla \cdot (\sigma \nabla \Phi) - \varepsilon_0 \varepsilon_r \nabla \cdot \left(\frac{\partial \nabla \Phi}{\partial t}\right) = 0.$$

Additionally, the homogeneous solution was solved according to the Laplace equation:

$$-\nabla \cdot (\nabla \varphi) = 0$$

For the heterogeneous case, the dielectric properties of various tissues were chosen from data generated by Gabriel et al. available at (http://niremf.ifac.cnr.it/docs/dielectric/home.html). Gabriel, S., R. W. Lau, and C. Gabriel, *The dielectric properties of biological tissues 0.2. Measurements in the frequency range* 10 *Hz to* 20 *GHz*. Physics in Medicine and Biology, 1996. 41(11): p. 2251-2269. The data was interpolated in Mathematica 7 (Wolfram Research, Inc.) in order to estimate the dielectric properties at 1 kHz and 1 MHz. For the homogeneous case, the electric field distribution is independent of the dielectric properties. The energized and grounded electrodes were subtracted from the skin and fat subdomains, and treated purely as boundary conditions at 1000 V and 0V, respectively.

FIGS. 34A and 34B show the electric field distribution during a bipolar burst with the frequencies given in TABLE IV.

TABLE IV

Dielectric properties of skin and fat tissue at various frequencies.

| | | Tissue | |
|---|---|---|---|
| Frequency | Property | Skin | Fat |
| 1 kHz | σ [S/m] | 0.000180 | 0.0246 |
| | $\varepsilon_r$ | 1170 | 20800 |
| 1 MHz | σ [S/m] | 0.0119 | 0.0267 |
| | $\varepsilon_r$ | 792 | 25 |

From the surface contour map, at 1 kHz, which is representative of a 500 μs traditional electroporation pulse, the electric field is highly non-uniform. A majority of the voltage drop occurs within the skin layer, and the fat layer remains untreated. However, at 1 MHz, which is representative of a 500 ns high-frequency electroporation pulse, the voltage drop is distributed more uniformly throughout the entire domain. As a result, both the skin and fat layers can be treated. Additionally, the electric field distribution at 1 MHz closely resembles that of the homogenous solution. Therefore, knowledge of dielectric properties and intricate geometrical arrangements of heterogeneous tissues can be neglected during treatment planning for high-frequency electroporation. This greatly reduces treatment planning protocols and produces more predictable outcomes.

Example IX

Modeling of Separation Distances Between Electrodes and Heat Generation.

Figure 35A:
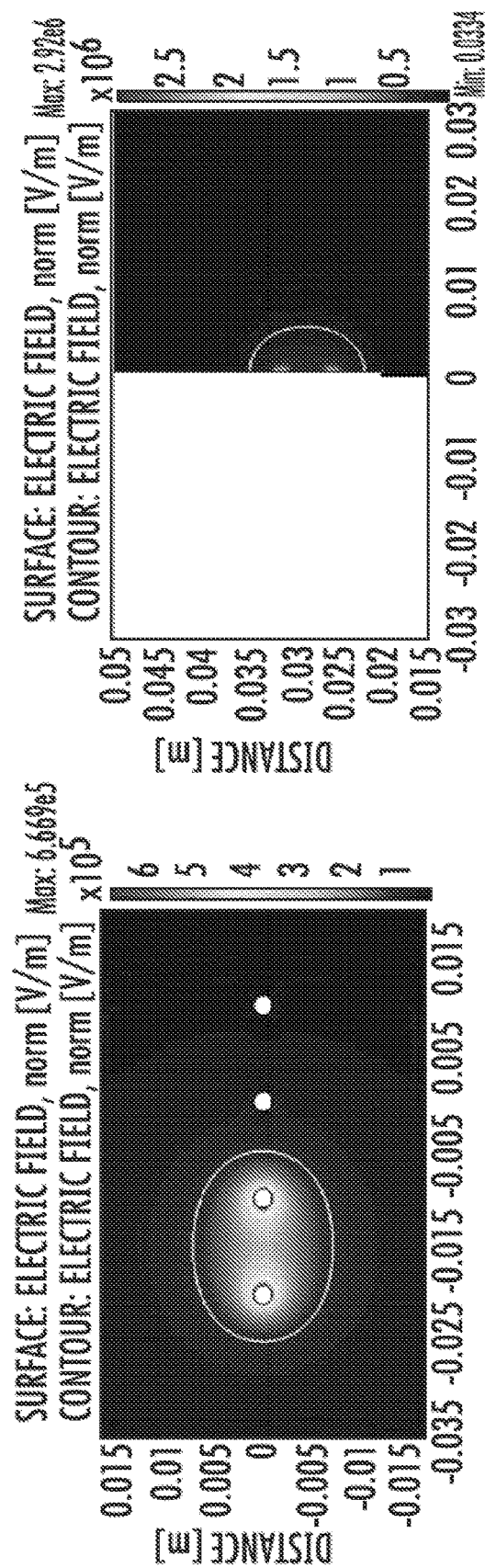
FIG. 35A depicts the use of two electrodes spaced 0.5 cm apart.
Figure 35B:
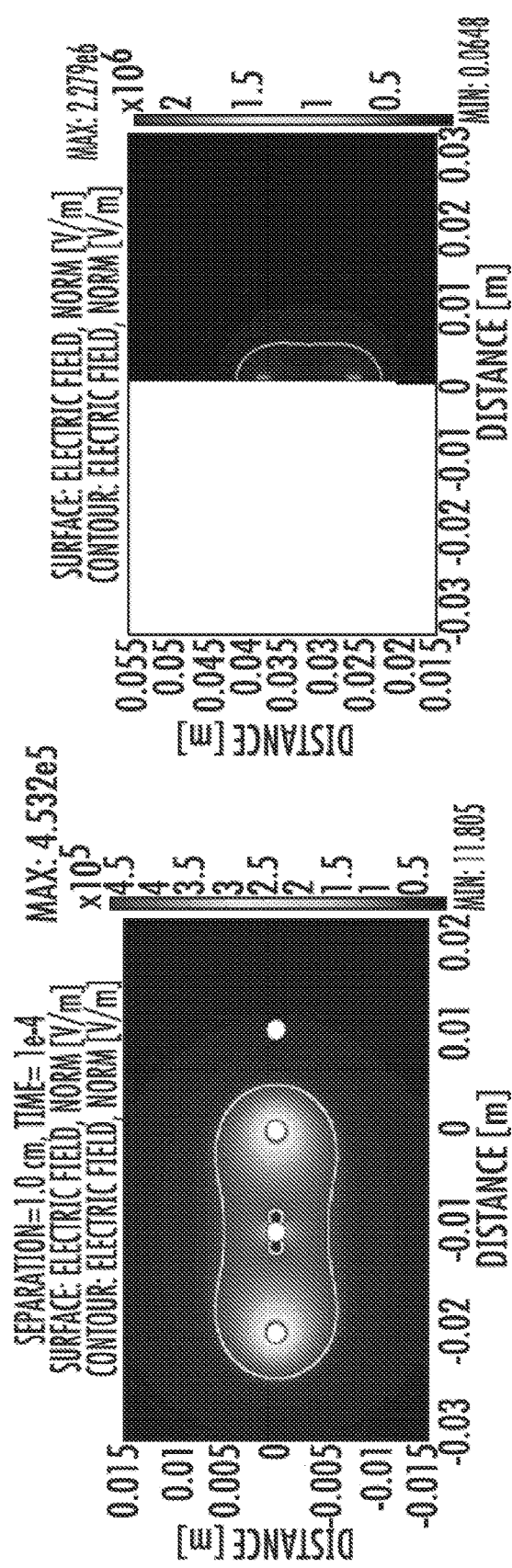
FIG. 35B depicts the use of two electrodes spaced 1.0 cm apart.
Figure 35C:
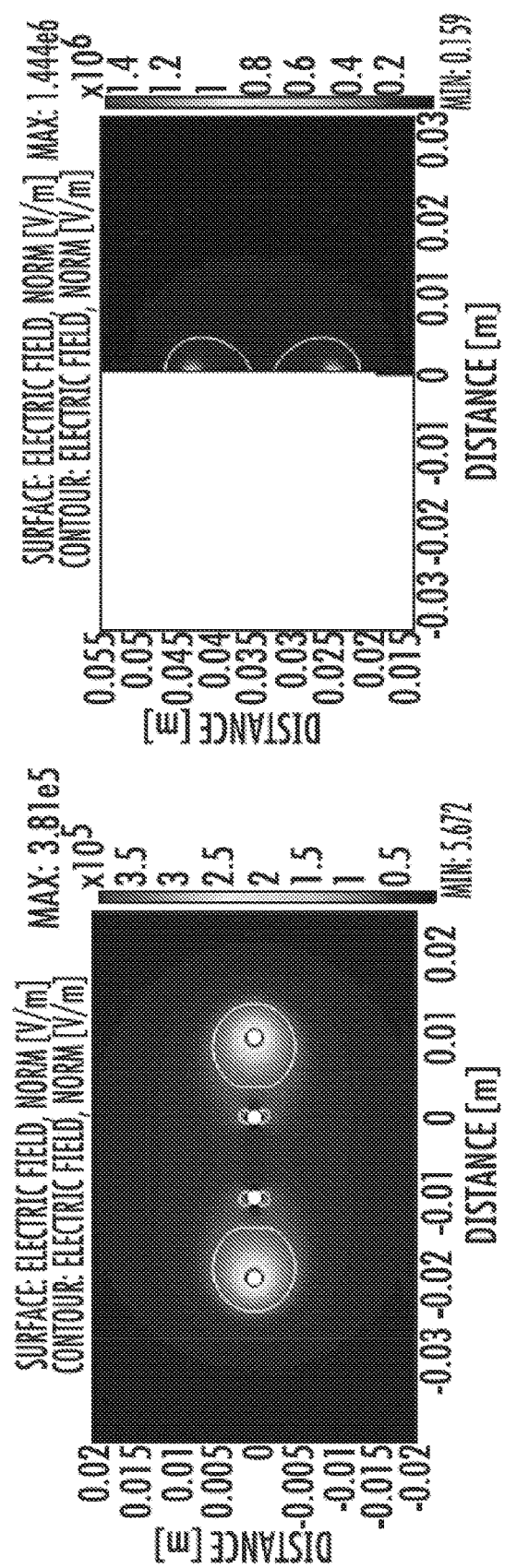
FIG. 35C depicts the use of two electrodes spaced 1.5 cm apart.

The system and method of the invention can include the use of multiple devices for treatment of tumors. The devices can be implanted in the tumor at varying distances from each other to achieve desired cell killing. Alternatively, the system and method can include the use of a single device having multiple electrodes along its tip. Modeling of placement of multiple devices or a single device with multiple electrodes in tissue was performed, and exemplary electrical fields generated are depicted in FIG. 35. The outputs depicted in the figure demonstrate the variability in IRE treatment region that results from altering the separation distance of the conducting electrode surfaces. More specifically, FIG. 35A-C, show three model outputs for 2-dimensional needles (left panels) and an axis symmetric electrode (right panels). For all images, there were two charged surfaces, one of 2500V and one of 0V. The distances between the electrodes were 0.5 cm (FIG. 35A), 1.0 cm (FIG. 35B), and 1.5 cm (FIG. 35C). From this data, it is clear that altering the distance leads to significantly different electric field distributions, and thus makes the distance an important parameter to consider when developing IRE protocols for various tumor ablation.

Figure 35D:
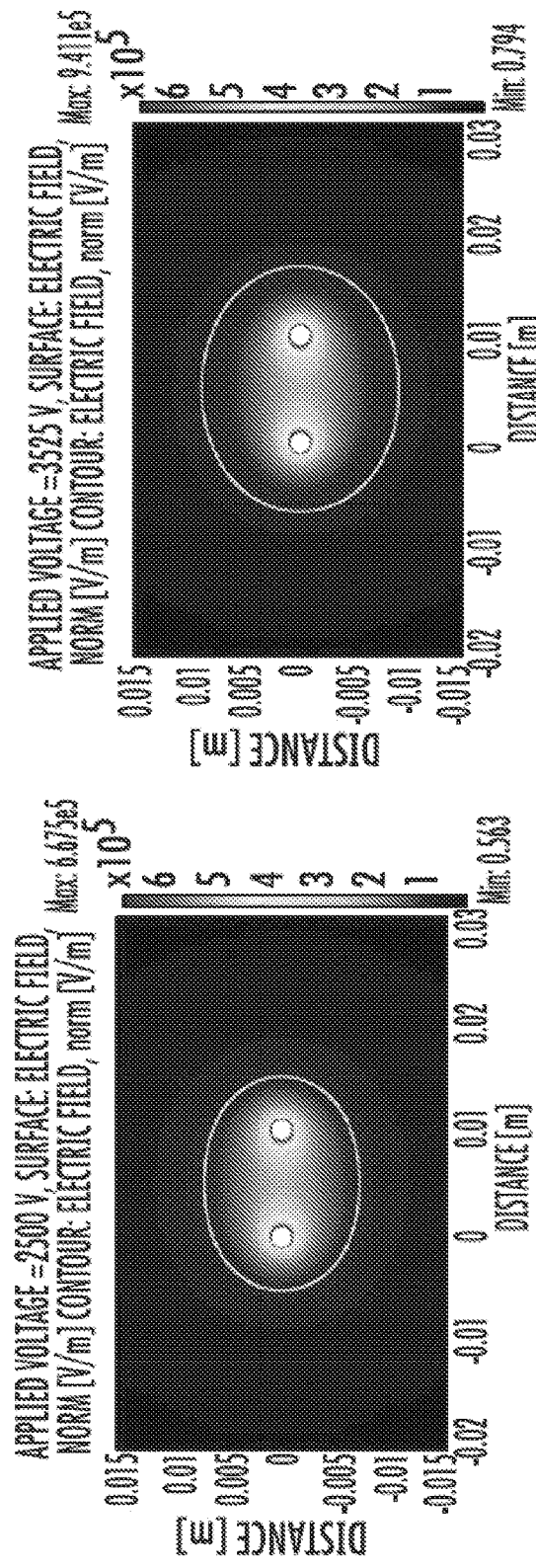
FIG. 35D depicts the use of two electrodes spaced 1.0 cm apart.

Numerical models representing two needles and an axis symmetric needle electrode configuration have been developed to compare the increase in treatment area shown by the electric field distribution for the same thermal effects between 100 and 50 μs pulse lengths. The area/volume of tissue that increased by at least 1 degree Kelvin was determined for a 100 μs pulse. This area/volume was then used for the 50 μs pulse to determine the electric field magnitude that would cause the same increase in temperature. A contour line has been created within these models to represent the region treated with the IRE threshold of 700V/cm. The results are shown in FIG. 35D. More specifically, 2-D needle electrodes with 3.13 mm2 area of tissue increased by one degree Kelvin for 100 is pulse at 2500V/cm with 226.2 mm2 area treated by IRE (FIG. 35D, left side) and 50 μs pulse at 3525V/cm with 325.6 mm2 area affected by IRE (FIG. 35D, right side). Axis symmetric needle electrode with 3.95 mm3 volume of tissue increased by 1 degree Kelvin for 100 μs at 1500V with 81.1 mm3 volume affected by IRE (FIG. 35E, left side) and 50 μs pulse at 2120V with a 133 mm3 volume within IRE range (FIG. 35E, right side).

According to the method of the invention, cycle times for pulses are set generally about 1 Hz. Furthermore, it has been found that alternating polarity of adjacent electrodes minimizes charge build up and provides a more uniform treatment zone. More specifically, in experiments performed by the inventors, a superficial focal ablative IRE lesion was created in the cranial aspect of the temporal lobe (ectosylvian gyrus) using the NanoKnifeB (Angiodynamics, Queensbury, N.Y.) generator, blunt tip bipolar electrode (Angiodynamics, No. 204002XX) by delivering 9 sets of ten 50 µs pulses (voltage-to-distance ratio 2000 V/cm) with alternating polarity between the sets to prevent charge build-up on the stainless steel electrode surfaces. These parameters were determined from ex-vivo experiments on canine brain and they ensured that the charge delivered during the procedure was lower than the charge delivered to the human brain during electroconvulsive therapy (an FDA approved treatment for major depression). Excessive charge delivery to the brain can induce memory loss, and thus is preferably avoided.

Surprisingly, it has been found that pulse durations for ablation of neoplasias, and in particular solid tumors, can be relatively short, thus reducing the probability of generation of thermal conditions and excessive charges that cause collateral damage to healthy tissues. More specifically, the present invention recognizes for the first time that, in contrast to prior disclosures relating to IRE, the pulse length for highly efficient tissue ablation can be lower than 100 microseconds (100 µs). Indeed, it has surprisingly been determined that a pulse length of 25 µs or lower can successfully cause non-thermal cell death. Thus, in embodiments, the method of treatment uses pulse lengths of 10 us, 15 us, 20 us, 25 us, 30 us, 35 us, 40 us, 45 us, 50 us, 55 us, 60 us, 65 us, 70 us, 75 us, 80 us, 85 us, or 90 us. Preferably, to most effectively minimize peripheral damage due to heat, pulse lengths are limited to 90 µs or less, for example 50 µs or less, such as 25 us. By reducing the pulse length, as compared to prior art techniques for IRE, larger electric fields can be applied to the treatment area while avoiding thermal damage to non-target tissue (as well as to target tissue). As a result of the decreased pulse length and concomitant reduction in heat production, the methods of the invention allow for treatment of tissues having higher volumes (e.g., larger tumors, non-solid tumors) than possible if prior art methods were to be employed for in vivo treatment of tumors.

According to the method, a tissue is exposed to an electrical field that is adequate in time and power to cause killing of cells of the tissue, but not adequate to significantly destroy the scaffolding upon and within which the cells exist. Furthermore, the electrical field does not cause irreversible tissue damage as a result of heating of the tissue. Various ways of providing such an electrical field are possible. General parameters follow; however, those of skill in the art are fully capable of devising alternative combinations to achieve the same end result without undue experimentation. In typical embodiments, one or more electrical pulses are applied to the tissue to cause cell membrane disruption as a result of the electricity and not substantially as a result of heat. Where two or more pulses are used, the pulses are separated by a period of time that allows, among other things, the tissue to cool so that thermal damage does not occur to a significant extent. For example, one or more electrical pulses can be applied to the tissue of interest for a duration in a range of from about 5 microseconds (µs) to about 62 seconds, such as 50 us. For convenience, a short period of treatment might be desired. As such, in preferred embodiments, electrical pulses are applied for a period of about 1-10000 µs. Further, although there is no limit on the number of pulses to be delivered to the tissues, in preferred embodiments, from about 1 to about 100 pulses are applied to the tissue. For example, in an exemplary embodiment, about 10-1000 pulses of about 100 µs each in duration are applied to the tissue to cause cellular ablation.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. It is intended that the specification and examples be considered as exemplary in nature and that variations that do not depart from the essence of the invention are intended to be within the scope of the invention.

The invention claimed is:

1. A device comprising:
    a generator configured to deliver 1 to 10,000 electrical pulses of 1 mV to 5,000 volts to at least one electrode;
    wherein a frequency rate of the electrical pulse delivery is 1 Hz to 100 MHz;
    wherein at least one of the electrical pulses is configured to have:
       a first polarity portion and a second polarity portion, each portion having a square waveform,
       a pulse width of at least 10 ns to 1 millisecond, and
       an intra-pulse instant charge reversal; and
    wherein the electrical pulses are configured to irreversibly electroporate cells of a target area.

2. The device of claim 1, wherein the generator is configured to deliver electrical pulses having a pulse width of 75 to 100 microseconds.

3. The device of claim 1, wherein the generator is configured to deliver 500 to 3,000 volts.

4. The device of claim 1, wherein the at least one electrical pulse is configured to be a neutral electrode charge.

5. The device of claim 1, wherein the electrical pulses are configured to provide for non-thermal ablation.

6. The device of claim 1, wherein the electrical pulses are delivered at a frequency rate of 25 kHz to 100 kHz.

7. The device of claim 1, wherein the generator is configured to deliver 80 to 110 electrical pulses.

8. A method comprising:
    delivering 1 to 10,000 electrical pulses of 1 mV to 5,000 volts to at least one electrode;
    wherein the electrical pulses are delivered at a frequency rate of 1 Hz to 100 MHz;
    alternating polarity of at least one of the electrical pulses during the pulse delivery; wherein the electrical pulse is configured to:
       instantly reverse charge intra-pulse between a first polarity portion and a second polarity portion, each portion having a square waveform, and
       have a pulse width of 10 ns to 1 millisecond; and
    irreversibly electroporating cells of a target area.

9. The method of claim 8, further comprising the step of: monitoring the temperature of the target area.

10. The method of claim 8, wherein the irreversibly electroporating provides non-thermal ablation.

11. The method of claim 8, wherein 1 to 110 electrical pulses are delivered.

12. The method of claim 11, wherein 80 to 110 electrical pulses are delivered.

13. The method of claim 8, wherein the electrical pulses are delivered at a voltage of 500 to 3,000 volts.

14. The method of claim 13, wherein the electrical pulses are delivered at a voltage of 1,500 to 2,500 volts.

15. The method of claim 8, wherein the electrical pulses are delivered at a frequency rate of 10 kHz to 100 kHz.

16. The method of claim 15, wherein the electrical pulses are delivered at a frequency rate of 25 kHz to 50 kHz.

17. The method of claim 8, wherein the electrical pulses have a pulse width of 50 to 100 microseconds.

18. The method of claim 17, wherein the electrical pulses have a pulse width of 75 to 100 microseconds.

19. A method comprising:
   delivering up to 110 electrical pulses of up to 3,000 volts to at least one electrode; wherein the electrical pulses are delivered at a frequency rate of 25 kHz to 100 MHz;
   alternating polarity of at least one of the electrical pulses during the pulse delivery, wherein the electrical pulse is configured to:
      have an intra-pulse time delay between alternating polarity; wherein the electrical pulse is configured to have a first polarity portion and a second polarity portion, each portion having a square waveform, and
      have a pulse width of 10 ns to 10 microseconds; and
   irreversibly electroporating cells of a target area.

20. The method of claim 19, wherein the electrical pulses are delivered at a frequency rate of 25 kHz to 50 kHz.

\* \* \* \* \*